United States Patent [19]

Audonnet et al.

[11] Patent Number: 5,733,554
[45] Date of Patent: Mar. 31, 1998

[54] AVIAN HERPESVIRUS-BASED LIVE RECOMBINANT AVIAN VACCINE, IN PARTICULAR AGAINST GUMBORO DISEASE

[75] Inventors: Jean-Christophe François Audonnet, Lyons; Michel Joseph Marie Bublot, Saint-Genis-Les-Ollieres; Raphaël Jean Darteil; Carole Véronique Duinat, both of Lyons; Eliane Louise Françoise Laplace, Oullins; Michel Albert Emile Riviere, Ecully, all of France

[73] Assignee: Rhone Merieux, Lyons, France

[21] Appl. No.: 368,803

[22] Filed: Jan. 5, 1995

[30] Foreign Application Priority Data

Dec. 30, 1994 [FR] France .................... 94 16015

[51] Int. Cl.$^6$ .................... A61K 39/295; A61K 39/255; A61K 39/12; C12N 7/01
[52] U.S. Cl. .................... 424/199.1; 435/235.1; 435/320.1; 424/229.1; 424/204.1
[58] Field of Search .................... 424/199.1, 202.1, 424/229.1, 204.1; 435/235.1, 236; 935/65

[56] References Cited

FOREIGN PATENT DOCUMENTS

| | | |
|---|---|---|
| WO90/02802 | 3/1990 | European Pat. Off. . |
| WO90/02803 | 3/1990 | European Pat. Off. . |
| 477056 | 3/1992 | European Pat. Off. . |
| 0 513 921 | 11/1992 | European Pat. Off. . |
| 2666589 | 3/1992 | France . |
| 2697534 | 5/1994 | France . |
| WO87/04463 | 7/1987 | WIPO . |
| WO89/01040 | 2/1989 | WIPO . |
| 93/25665 | 12/1993 | WIPO ........... C12N 7/00 |
| 9410321 | 5/1994 | WIPO . |

OTHER PUBLICATIONS

Bradley, G. et al. 1989. Journal of Virology, vol. 63, pp. 2534–2542.

"Herpesviruses As Vectors", Janis K. McMillen, Ph.D., SyntroVet Incorporated pp. 355–363. (1994).

"Protection of Chickens from Newcastle and Marek's Diseases with a Recombinant Herpesvirus of Turkeys . . . ", Morgan et al., Avian Diseases 36:858–870, 1992.

"Efficacy in Chickens of a Herpesvirus of Turkeys Recombinant Vaccine Containing the Fusion Gene . . . ", Morgan et al., Avian Diseases, 37:1032–1040, 1993.

"Influence of Dose and Route of Inoculation on Responses of Chickens to Recombinant Fowlpox Virus Vaccines", Boyle et al., Veterinary Micro–Biology 41 (1994) 173–181.

"Infection Bursal Disease Virus Structural Protein VP2 Expressed by a Fowlpox Virus Recombinant Confers Protection Against Disease in Chickens", Heine et al Arch Virol (1993) 131:277–292.

"A Recombinant Fowlpox Virus that Expresses the VP2 Antigen of Infectious Bursal Disease Virus Induces Protection Against Mortality Caused by the Virus", Bayliss et al, Arch Virol (1991) 120:193–205.

"Plasmid–Associated Effects on Test Gene Expression and Marek's Disease Virus Plaque Formation during Recombination Trials", Marshall et al, Journal of Virological Methods, 40 (1992) 195–204.

"Selection of Marek's Disease Virus Recombinants Expressing the *Escherichia coli* gpt Gene", Marshall et al., Virology 195, 638–648 (1993).

Primary Examiner—Mary E. Mosher
Attorney, Agent, or Firm—Larson and Taylor

[57] ABSTRACT

The present invention relates to vaccines for avian use which are based on live recombinant avian herpesviruses, in particular the Marek's disease viruses including HVT virus (herpesvirus of turkey), in which has been inserted, by genetic recombination, at least one nucleotide sequence which encodes and expresses an antigenic polypeptide of an avian pathogen under conditions which ensure immunization leading to efficient protection of the vaccinated animal against the pathogen. In one embodiment, the antigenic polypeptide is inserted in the UL43 gene under the control of the CMV immediate early promoter. The vaccines of the present invention are advantageous over previously used vaccines in that they can be used to ensure total protection of animals against Gumboro disease and to immunize chicks as young as one-day old without secondary effects, and only require low doses.

13 Claims, 38 Drawing Sheets

```
        SacI
   1 GAGCTCTCCTGGATGGTGGGACAGGCGCTACGTCTCAACCAGTTTCATTTCTCGCGACGA
  61 ATTACAGCTGGTTTTTGCAGCGCCGTCCCGAGAATTAGATGGTTTATATACGCGCGTAGT
 121 AGTTGTCAACGGGGACTTTACTACGGCCGATATAATGTTTAATGTTAAAGTGGCATGTGC
 181 CTTTTCAAAGACTGGAATAGAAGATGATACATTATGCAAACCCTTTCATTTCTTTGCCAA
 241 TGCAACATTGCACAATTTAACCATGATTAGATCGGTAACTCTTCGAGCGCACGAAAGCCA
                                                       PstI
 301 TTTAAAGGAATGGGTGGCACGGAGAGGTGGTAACGTCCCTGCAGTGCTACTTGAGTCTAC
 361 CATGTATCATGCATCCAATCTGCCTAGAAATTTCAGGGATTTCTACATAAAGTCTCCAGA
 421 TGATTATAAGTATAATCACCTAGATGGGCCATCTGTAATGCTCATCACTGACAGACCTAG
 481 TGAAGATTTGGATGGGAGGCTCGTTCACCAAAGTGACATTTTTACTACTACAAGTCCTAT
 541 AAAACAGGTCCGGTATGAAGAGCATCAGTCACATACAAAGCAGTATCCTGTAAACAAAAT
 601 ACAAGCTATAATTTTTTGATAGGGTTAGGCTCGTTCATTGGAAGCATATTCGTAGTTTT
 661 GGTAGTATGGATTATACGCAGATATTGCAATGGAGCGCGGAGTGGGGGAACGCCCCCCAG
 721 TCCTCGCCGGTATGTGTATACCAGGCTATGATCACGTGTGAAACTTGGGCGGACCTGTAT
 781 CATATGTACACCGTCCCTATTCGTTTATAGCCAGTACGTGTTATCTGCACATAGAGGAAC
 841 ATGTGTCATACTGGGATCGCATGCATGGTATGTGTGACTCTAATATTATTCTGTATCATA
   1▸MetCysHisThrGlyIleAlaCysMetValCysValThrLeuIleLeuPheCysIleIle
 901 ATAAAAACACAGTGCATGGTATATAGAGGATCGCTGGTAAGCACTACGGTAGACCAATCG
  21▸IleLysThrGlnCysMetValTyrArgGlySerLeuValSerThrThrValAspGlnSer
 961 GCTCAGATTGCATTCTTTGGCATCGATACCGTTGTTAATTTATATGGCAAAGTCTTGTTC
  41▸AlaGlnIleAlaPhePheGlyIleAspThrValValAsnLeuTyrGlyLysValLeuPhe
1021 ATGGGAGATCAGTATTTGGAGGAAATATACTCTGGAACGATGGAAATACTCAAATGGAAT
  61▸MetGlyAspGlnTyrLeuGluGluIleTyrSerGlyThrMetGluIleLeuLysTrpAsn
1081 CAAGCTAACCGCTGCTATTCTATTGCGCATGCAACATATTACGCCGACTGTCCTATAATC
  81▸GlnAlaAsnArgCysTyrSerIleAlaHisAlaThrTyrTyrAlaAspCysProIleIle
1141 AGTTCTACGGTATTCAGAGGATGCCGGGACGCCGTTGTTTATACTAGGCCCCACAGCAGA
 101▸SerSerThrValPheArgGlyCysArgAspAlaValValTyrThrArgProHisSerArg
1201 ATTCATCCCCAATATCGAAACGGGCTGCTTTTGACTATTATCGAGCCACGGATGGAGGAT
 121▸IleHisProGlnTyrArgAsnGlyLeuLeuLeuThrIleIleGluProArgMetGluAsp
1261 TCTGGTATCTATTATATACGCACTTCAATAGATGGTTTTAACAAGAGCGATTATGCGAGA
 141▸SerGlyIleTyrTyrIleArgThrSerIleAspGlyPheAsnLysSerAspTyrAlaArg
1321 ACATCTATTTTTGTATGTAATGGGTCGTCTGGATCGTGTTCTAACCCCGCCAAAAAGTT
 161▸ThrSerIlePheValCysAsnGlySerSerGlySerCysSerAsnProArgGlnLysVal
1381 TCAGATGAAATGTGCATCCCCCACGTAAATCGTATTGCATTTGAGCGATATTTAACCCTA
 181▸SerAspGluMetCysIleProHisValAsnArgIleAlaPheGluArgTyrLeuThrLeu
1441 CATGTTGGACGGTTGCCCTACGGAGACTTGACATTACAGCAGATACGTAAGGACATGACG
 201▸HisValGlyArgLeuProTyrGlyAspLeuThrLeuGlnGlnIleArgLysAspMetThr
1501 ACCACCGCTCCTACATATCGTACCATTCGCAGAACTACAGTTAATGAGGGTTTGTTGACA
 221▸ThrThrAlaProThrTyrArgThrIleArgArgThrThrValAsnGluGlyLeuLeuThr
1561 GCCAAGACATCCCCTGATATCGATTTAAATGCAACAAATTTGCCCCTACCCATTAGTAAC
 241▸AlaLysThrSerProAspIleAspLeuAsnAlaThrAsnLeuProLeuProIleSerAsn
1621 TACACAGATTATATGAGTGTTATTTGGAGACGTGTTGCCTTAAGACGAATTTATGCTTAT
 261▸TyrThrAspTyrMetSerValIleTrpArgArgValAlaLeuArgArgIleTyrAlaTyr
1681 TTGGTGATCGCTATTATAGCATTGTTGATAGTAACAGTCTGCTCCGCACATAAAAGAGGC
 281▸LeuValIleAlaIleIleAlaLeuLeuIleValThrValCysSerAlaHisLysArgGly
```

FIG. 1-1

```
                  SalI
1741 AGTTGTAGTCGTCGACGTAGAATCTACATAGGCAATGAACCTACTACATTGACTTCGATC
 301▶SerCysSerArgArgArgArgIleTyrIleGlyAsnGluProThrThrLeuThrSerIle
1801 ACTAACGGAAATTTCCAAGAAAAGGAGACCAAGAATGTACCGTCCGACATCTCAGACGCT
 321▶ThrAsnGlyAsnPheGlnGluLysGluThrLysAsnValProSerAspIleSerAspAla
              XhoI
1861 GAGCTTTTGGAGAGACTCGAGAAGAAGATAGAAATGTTACGGACTGAATAATTTCCAAAT
 341▶GluLeuLeuGluArgLeuGluLysLysIleGluMetLeuArgThrGlu•••
1921 GGCAGTTAGGTACCCAGGAATGTTGGGATATGTAGATGTATTAGCTATAAGTCCGTATTT
1981 AAGGGGAGTGGCCCACCAATAATAAACTCTGGTATTTTTGTCTGGGAATTCAGTTGTGCT

2041 TTAAGGCGACCTGCTGTTTCGATATGCGCGCGTGTCGATTATCCATCCTCATATTATTAT
2101 TGCAGACGATCTCGGCGAGTATGATACAACATTTAGATTTATTAGAGGGGCAATCTGTTG
2161 CAGTCGATATTCCAAGATATCCGCCGCTAACAAACGGTACTATTTATACTGAAACATGGA
2221 CGTGGATTTCAAGTATTTGCAACGATACATCGATGGGTTATATATGTTTGGATCGCGCAA
2281 CGTGTTTTCAGGATTTGCTTTTGGGGACATCTTGCGTAAGGTATGGTGAAGAAAAGATCT
2341 TGAGGGTGGATAGATTTGTTGTGAATAGTGGGTCTCTTGACAGGATAGCGTCTTCTCAGT
2401 TTCATTATATACCGAATGTAATAATAGGCACTGGACGGGGAAAGGAACTTACTATCTTCA
2461 ATGCTACATCGCAAATCGCTGGTGTATATACGCGATATACCAGGAACGATAGTAGGCCCG
2521 CTGTAATGGATGTCCTTTTAGTGTGGGTTTCGGTGCATGGGCAAGCTCCAGATCGTACTA
2581 TGAACATATATATCACCCCCCCGTCGAC
```

FIG. 1-2

```
                BamHI
   1 GGATCCGAGCTTCTACTATACAACGCGGACGATAATTTTGTCCACCCCATCGGTGTTCGA
  61 GAAAGGGTTTTTATGATGGCAGGAATAACTGTCGCATGTGACCACACTGCAGGAGAGGCT
 121 CATACACCCGAGGATATGCAAAAGAAATGGAGGATTATATTGGCAGGGGAAAAATTCATG
 181 ACTATATCGGCATCGTTGAAATCGATCGTCAGTTGTGTGAAAAACCCCCTTCTCACGTTT
 241 GGCGCAGATGGGCTCATTGTACAAGGTACTGTCTGCGGACAGCGCATTTTGTTCCAATC
 301 GACCGTGATTCCTTCAGCGAATATGAATGGCATGGGCCAACTGCGATGTTTCTAGCATTA
 361 ACTGATTCCAGACGCACTCTTTTAGATGCATTCAAATGTGAAAAGAGAAGGGCAATTGAC
 421 GTCTCCTTTACCTTCGCGGGAGAGCCTCCATGTAGGCATTTAATCCAAGCCGTCACATAC
                                                     SacI
 481 ATGACCGACGGTGGTTCAGTATCGAATACAATCATTAAATATGAGCTCTGGAATGCGTCT
 541 ACAATTTTCCCCCAAAAAACTCCCGATGTTACCTTTTCTCTAAACAAACAACAATTGAAC
 601 AAAATATTGGCCGTCGCTTCAAAACTGCAACACGAAGAACTTGTATTCTCTTTAAAACCT
 661 GAAGGAGGGTTCTACGTAGGAACGGTTTGTACTGTTATAAGTTTCGAAGTAGATGGGACT
 721 GCCATGACTCAGTATCCTTACAACCCTCCAACCTCGGCTACCCTAGCTCTCGTAGTAGCA
 781 TGCAGAAGAAGAAGGCGAATAAAAACACTATTTTAACGGCCTATGGAAGTGGTAAACCC
 841 TTTTGTGTTGCATTGGAAGATACTAGTGCATTTAGAAATATCGTCAATAAAATCAAGGCG
 901 GGTACGTCGGGAGTTGATCTGGGGTTTTATACAACTTGCGATCCGCCGATGCTATGTATT
 961 CGCCCACACGCATTTGGAAGTCCTACCGCATTCCTGTTTTGTAACACAGACTGTATGACA
1021 ATATATGAACTGGAAGAAGTAAGCGCCGTTGATGGTGCAATCCGAGCAAAACGCATCAAC
1081 GAATATTTCCCAACAGTATCGCAGGCTACTTCCAAGAAGAGAAAACAGTCGCCGCCCCCT
1141 ATCGAAAGAGAAAGGAAAACCACCAGAGCGGATACCCAATAAAATGCCAGACAAACCCGG
1201 CATCCTGGTTAGAGGGCAGGTGGGCTGGGCCAACCTTCACGGGCGTCCGACAGATCGGTG
1261 ACACTCATACGTTAACTAAACGCCGGCAGCTTTGCAGAAGAAAATATGCCTTCCGGAGCC
                                                   1▸MetProSerGlyAla
         XhoI
1321 AGCTCGAGTCCTCCACCAGCTTATACATCTGCAGCTCCGCTTGAGACTTATAACAGCTGG
    6▸SerSerSerProProProAlaTyrThrSerAlaAlaProLeuGluThrTyrAsnSerTrp
1381 CTAAGTGCCTTTTCATGCGCATATCCCCAATGCACTGCGGGAAGAGGACATCGACAAAAT
   26▸LeuSerAlaPheSerCysAlaTyrProGlnCysThrAlaGlyArgGlyHisArgGlnAsn
1441 GGCAAGAAGTGTATACGGTGTATAGTGATCAGTGTATGTTCCTTAGTGTGCATCGCTGCA
   46▸GlyLysLysCysIleArgCysIleValIleSerValCysSerLeuValCysIleAlaAla
1501 CATTTAGCTGTTACCGTGTCGGGAGTGGCATTAATTCCGCTTATCGATCAAAACAGAGCT
   66▸HisLeuAlaValThrValSerGlyValAlaLeuIleProLeuIleAspGlnAsnArgAla
1561 TACGGAAACTGTACGGTATGTGTAATTGCCGGATTCATCGCTACGTTTGCTGCACGACTT
   86▸TyrGlyAsnCysThrValCysValIleAlaGlyPheIleAlaThrPheAlaAlaArgLeu
1621 ACGATAAGACTTTCGGAAACGCTTATGCTAGTGGGCAAGCCGGCGCAGTTTATATTTGCT
  106▸ThrIleArgLeuSerGluThrLeuMetLeuValGlyLysProAlaGlnPheIlePheAla
1681 ATAATCGCTTCCGTTGCGGAAACACTGATCAATAACGAGGCGCTTGCCATCAGTAATACT
  126▸IleIleAlaSerValAlaGluThrLeuIleAsnAsnGluAlaLeuAlaIleSerAsnThr
1741 ACTTACAAAACTGCATTGCGAATAATCGAAGTAACATCTTTGGCGTGTTTTGTTATGCTC
  146▸ThrTyrLysThrAlaLeuArgIleIleGluValThrSerLeuAlaCysPheValMetLeu
1801 GGGGCAATAATTACATCCCACAACTATGTCTGCATTTCAACGGCAGGGGACTTGACTTGG
  166▸GlyAlaIleIleThrSerHisAsnTyrValCysIleSerThrAlaGlyAspLeuThrTrp
1861 AAGGCGGGATTTTTCATGCTTACCACCGGAACATTACTCGGTATAACAATACCAAACATA
  186▸LysAlaGlyPhePheMetLeuThrThrGlyThrLeuLeuGlyIleThrIleProAsnIle
1921 CACCCAATCCCTCTCGCGGGGTTCTTGCAGTCTATACAATATTGGCTATAAATATCGCT
  206▸HisProIleProLeuAlaGlyPheLeuAlaValTyrThrIleLeuAlaIleAsnIleAla
1981 AGAGATGCAAGCGCTACATTATTATCCACTTGCTATTATCGCAATTGCCGCGAGAGGACT
  226▸ArgAspAlaSerAlaThrLeuLeuSerThrCysTyrTyrArgAsnCysArgGluArgThr
2041 ATACTTCGCCCTTCTCGTCTCGGACATGGTTACACAATCCCTTCTCCCGGTGCCGATATG
  246▸IleLeuArgProSerArgLeuGlyHisGlyTyrThrIleProSerProGlyAlaAspMet
2101 CTTTATGAAGAAGACGTATATAGTTTTGACGCAGCTAAAGGCCATTATTCGTCAATATTT
  266▸LeuTyrGluGluAspValTyrSerPheAspAlaAlaLysGlyHisTyrSerSerIlePhe
```

FIG. 9-1

```
                            NcoI
2161 CTATGTTATGCCATGGGCTTACAACACCGCTGATTATTGCGCTCCATAAATATATGGCG
 286►LeuCysTyrAlaMetGlyLeuThrThrProLeuIleIleAlaLeuHisLysTyrMetAla
2221 GGCATTAAAAAATTCGTCAGATTGGACTGCTACATTACAAGGCATGTACGGGCTTGTCTTG
 306►GlyIleLysAsnSerSerAspTrpThrAlaThrLeuGlnGlyMetTyrGlyLeuValLeu
2281 GGATCGCTATCGTCACTATGTATTCCATCCAGCAACAACGATGCCCTAATTCGTCCCATT
 326►GlySerLeuSerSerLeuCysIleProSerSerAsnAsnAspAlaLeuIleArgProIle
2341 CAAATTTTGATATTGATAATCGGTGCACTGGCCATTGCATTGGCTGGATGTGGTCAAATT
 346►GlnIleLeuIleLeuIleIleGlyAlaLeuAlaIleAlaLeuAlaGlyCysGlyGlnIle

2401 ATAGGGCCTACATTATTTGCCGCGAGTTCGGCTGCGATGTCATGTTTTACATGTATCAAT
 366►IleGlyProThrLeuPheAlaAlaSerSerAlaAlaMetSerCysPheThrCysIleAsn
2461 ATTCGCGCTACTAATAAGGGTGTCAACAAATTGGCAGCAGCAGTGTCGTGAAATCTGTAC
 386►IleArgAlaThrAsnLysGlyValAsnLysLeuAlaAlaAlaValSer•••
2521 TGGGCTTCATTATTTCCGGGATGCTTACTTGCGTGCTATTACCACTATCGTGATAGATCG
2581 TCGGTCTGCGCATCGCCCATGCTGGCGGAACGCTCTTTCGAACCGTGAATAAAACTTTGT
2641 ATCTACTAAACAATAACTTTGTGTTTTATTGAGCGGTCGAAAACAATGAGGAGCTGCAAT
2701 TTAAAGCTAACCGCATACGCCGGCGGGTAAAGACCATTTTATACCATATTACGCATCTA
2761 TCGAAACTTGTTCGAGAACCGCAAGTATATGGTTTCCAACATGCGTTCTACGCGTACTGC
2821 GCTGACGGGATGGGTGGGCATATTTCTAGTTCTGTCTTTACAGCAAACCTCTTGTGCCGG
2881 ATTGCCCCATAACGTCGATACCCATCATATCCTAACTTTCAACCCTTCTCCCATTTCGGC
2941 CGATGGCGTTCCTTTGTCAGAGGTGCCCAATTCGCCTACGACCGAATTATCTACAACTGT
3001 CGCCACCAAGACAGCTGTACCGACGACTGAAAGCACTAGTTCCTCCGAAGCGCACCGCAA
3061 CTCTTCTCACAAAATACCTGATATAATCTGCGACCGAGAAGAAGTATTCGTATTCCTTAA
                                                         SalI
3121 CAATACAGGAAGAATTTTGTGTGACCTTATAGTCGACCCCCCTTCAGACGATGAATGGTC
3181 CAACTTCGCTCTTGACGTCACGTTCAATCCAATCGAATACCACGCCAACGAAAAGAATGT
3241 AGAGGTTGCCCGAGTGGCCGGTCTATACGGAGTACCGGGGTCGGATTATGCATACCCTAG
                                                    BamHI
3301 GAAATCGGAATTAATATCCTCCATTCGACGGGATCC
```

FIG. 9-2

```
   1 TGCTACCTGATGTACAAGCAAAAGGCACAACAAAAGACCTTGTTATGGCTTGGGAATAAT
  61 ACCCTTGATCAGATGAGAGCCACTACAAAAATATGAATACAAACGAGAGGCGGAGGTATC
 121 CCCAATAGCAATTTGCGTGTAAATTCTGGCAACCTGTTAATTAGAAGAATTAAGAAAAAA
 181 CCACTGGATGTAAGTGACAAACAAGCAATACACGGGTAGAACGGTCGGAGAAGCCACCCC
 241 TCAATCGGGAATCAGGCCTCACAACGTCCTTTCTACCGCATCATCAATAGCAGACTTCGG
 301 TCATGGACCGTGCAGTTAGCAGAGTTGCGCTAGAGAATGAAGAAAGAGAAGCAAAGAATA
     1▶MetAspArgAlaValSerArgValAlaLeuGluAsnGluGluArgGluAlaLysAsnT
 361 CATGGCGCTTTGTATTCCGGATTGCAATCTTACTTTTAATAGTAACAACCTTAGCCATCT
    20▶hrTrpArgPheValPheArgIleAlaIleLeuLeuLeuIleValThrThrLeuAlaIleS
 421 CTGCAACCGCCCTGGTATATAGCATGGAGGCTAGCACGCCTGGCGACCTTGTTGGCATAC
    40▶erAlaThrAlaLeuValTyrSerMetGluAlaSerThrProGlyAspLeuValGlyIleP
 481 CGACTATGATCTCTAAGGCAGAAGAAAAGATTACATCTGCACTCAGTTCTAATCAAGATG
    60▶roThrMetIleSerLysAlaGluGluLysIleThrSerAlaLeuSerSerAsnGlnAspV
 541 TAGTAGATAGGATATATAAGCAGGTGGCCCTTGAGTCTCCATTGGCGTTGCTAAACACTG
    80▶alValAspArgIleTyrLysGlnValAlaLeuGluSerProLeuAlaLeuLeuAsnThrG
 601 AATCTGTAATTATGAATGCAATAACGTCTCTCTCTTATCAAATCAATGGAGCTGCAAATA
   100▶luSerValIleMetAsnAlaIleThrSerLeuSerTyrGlnIleAsnGlyAlaAlaAsnA
                                    BspHI
 661 ATAGCGGGTGTGGGGCACCTGTTCATGACCCAGATTATATCGGGGGGATAGGCAAAGAAC
   120▶snSerGlyCysGlyAlaProValHisAspProAspTyrIleGlyGlyIleGlyLysGluL
 721 TTATTGTGGATGACGCTAGTGATGTCACATCATTCTATCCCTCTGCGTTCCAAGAACACC
   140▶euIleValAspAspAlaSerAspValThrSerPheTyrProSerAlaPheGlnGluHisL
 781 TGAACTTTATCCCGGCACCTACTACAGGATCAGGTTGCACTCGGATACCCTCATTCGACA
   160▶euAsnPheIleProAlaProThrThrGlySerGlyCysThrArgIleProSerPheAspI
 841 TAAGCGCTACCCACTACTGTTACACTCACAATGTGATATTATCTGGTTGCAGAGATCACT
   180▶leSerAlaThrHisTyrCysTyrThrHisAsnValIleLeuSerGlyCysArgAspHisS
 901 CACACTCATATCAGTACTTAGCACTTGGCGTGCTTCGGACATCTGCAACAGGGAGGGTAT
   200▶erHisSerTyrGlnTyrLeuAlaLeuGlyValLeuArgThrSerAlaThrGlyArgValP
 961 TCTTTTCTACTCTGCGTTCCATCAATTTGGATGACAGCCAAAATCGGAAGTCTTGCAGTG
   220▶hePheSerThrLeuArgSerIleAsnLeuAspAspSerGlnAsnArgLysSerCysSerV
1021 TGAGTGCAACTCCCTTAGGTTGTGATATGCTGTGCTCTAAAATCACAGAGACTGAGGAAG
   240▶alSerAlaThrProLeuGlyCysAspMetLeuCysSerLysIleThrGluThrGluGluG
                                    ClaI
1081 AGGATTATAGTTCAATTACGCCTACATCGATGGTGCACGGAAGGTTAGGGTTTGACGGTC
   260▶luAspTyrSerSerIleThrProThrSerMetValHisGlyArgLeuGlyPheAspGlyG
1141 AATACCATGAGAAGGACTTAGACGTCATAACTTTATTTAAGGATTGGGTGGCAAATTACC
   280▶lnTyrHisGluLysAspLeuAspValIleThrLeuPheLysAspTrpValAlaAsnTyrP
1201 CAGGAGTGGGGGGTGGGTCTTTTATTAACAACCGCGTATGGTTCCCAGTCTACGGAGGGC
   300▶roGlyValGlyGlyGlySerPheIleAsnAsnArgValTrpPheProValTyrGlyGlyL
1261 TAAAACCCAATTCGCCTAGTGACACCGCACAAGAAGGGAGATATGTAATATACAAGCGCT
   320▶euLysProAsnSerProSerAspThrAlaGlnGluGlyArgTyrValIleTyrLysArgT
1321 ACAATGACACATGCCCAGATGAACAAGATTACCAGATTCGGATGGCTAAGTCTTCATATA
   340▶yrAsnAspThrCysProAspGluGlnAspTyrGlnIleArgMetAlaLysSerSerTyrL
1381 AGCCTGGCGGTTTGGTGGAAAACGCGTACAGCAGGCCATCTTATCTATCAAGGTGTCAA
   360▶ysProGlyArgPheGlyGlyLysArgValGlnGlnAlaIleLeuSerIleLysValSerT
1441 CATCTTTGGGCGAGGACCCGGTGCTGACTGTACCGCCTAATACAATCACACTCATGGGGG
   380▶hrSerLeuGlyGluAspProValLeuThrValProProAsnThrIleThrLeuMetGlyA
1501 CCGAACGGAGAGTTCTCACAGTAGGGACATCTCATTTCTTGTACCAGCGAGGGTCTTCAT
   400▶laGluArgArgValLeuThrValGlyThrSerHisPheLeuTyrGlnArgGlySerSerT
```

FIG. 21-1

```
1561 ACTTCTCTCCTGCTTTATTATACCCTATGACAGTCAACAACAAAACGGCTACTCTTCATA
 420▶yrPheSerProAlaLeuLeuTyrProMetThrValAsnAsnLysThrAlaThrLeuHisS
1621 GTCCTTACACATTCAATGCTTTCACTAGGCCAGGTAGTGTCCCTTGTCAGGCATCAGCAA
 440▶erProTyrThrPheAsnAlaPheThrArgProGlySerValProCysGlnAlaSerAlaA
1681 GATGCCCCAACTCATGTGTCACTGGAGTTTATACTGATCCGTATCCCTTAGTCTTCCATA
 460▶rgCysProAsnSerCysValThrGlyValTyrThrAspProTyrProLeuValPheHisA
1741 GGAACCATACCTTGCGGGGGGTATTCGGGACAATGCTTGATGATGAACAAGCAAGACTTA
 480▶rgAsnHisThrLeuArgGlyValPheGlyThrMetLeuAspAspGluGlnAlaArgLeuA
              PstI
1801 ACCCTGTATCTGCAGTATTTGATAACATATCCCGCAGTCGCATAACCCGGGTAAGTTCAA
 500▶snProValSerAlaValPheAspAsnIleSerArgSerArgIleThrArgValSerSerS
1861 GCCGTACTAAGGCAGCATACACGACATCGACATGTTTTAAAGTTGTCAAGACCAATAAAA
 520▶erArgThrLysAlaAlaTyrThrThrSerThrCysPheLysValValLysThrAsnLysT
1921 CATATTGCCTCAGCATTGCAGAAATATCCAATACCCTCTTCGGGGAATTCAGGATCGTTC
 540▶hrTyrCysLeuSerIleAlaGluIleSerAsnThrLeuPheGlyGluPheArgIleValP
1981 CTTTACTAGTTGAGATTCTCAAGGATGATGGGATTTAAGAAGCCAGGTCTGGCCAGTTGA
 560▶roLeuLeuValGluIleLeuLysAsp
2041 GTCAACTGCGAGAGGGTCGGAAAGATGACATTGTGTCACCTTTTTTTTGTAATGCCAAGG
2101 ATCAAACTGGATACCGGCGCGAGCCCGAATCCTATGCTGCCAGTCAGCCATAATCAGATA
2161 GTACTAATATGATTAGTCTTAATCTTGTCGATAGTAACTTGGTTAAGAAAAAATATGAGT
2221 GGTAGTGAGATACACAGCTAAACAACTCACGAGAGATAGCACGGGTAGGACATGGCGAGC
2281 TCCGGTCCCGAAAGGGCAGAGCATCAGATTATCCTACCAGAGTCACATCTGTCCTCACCA
2341 TTGGTCAAGCACAAACTGCTCTATTACTGGAAATTAACTGGCGTACCGCTTCCTGACGAA
2401 TGTGACTTCGACCACCTCATTATCAGCCGACAATGGAAGAAAATACTTGAATCGGCCACT
2461 CCTGACACTGAGAGGATGATAAAGCTCGGCGGGCAGTACACCAGACTCTCGACCACCGC
2521 C
```

FIG. 21-2

```
            10         20         30         40         50         60
             |          |          |          |          |          |
  1 GAATTCCATCACCCCCTGCCGATCTTGCACGCGGGGACGAGCAAAGCGTGCGGTGCGGGC
 61 AGAAAGACAAGGATGGCTGTGGGTTGAAAGATGAAAAACAAATCGCGGTTGTGGGTCATG
121 AGTGGAGGGAGGGTGCCATCTGTGATGCCGAGAGGTCAAACTATGTTATAAAGAAAAACG
181 ATGGGTGGGAAATATAATAAAGCAACCGAAATGGTACATAAAAACTAAAAATACCTACAC
241 GGTTACACCACCGATCAGGCGAAGAAGTTCCAAACGATTAACAACCGGGACGAGACGTTG
301 CCGTTCGATCCAGGTCTCTGCTTTTTTGTATCTCTTATCCTATACCGCCGCCTCCCGTCC
361 GACGAGAGCAAGTCGCACCGCCACTCGAGGCCACAAGAAATTACGATTCTTATACGGGTG
421 GGCGTACCGCCTACTCGAACTATCACGTGATGTGTATGCAAATGAGCAGTGCGAACGCGT
481 CAGCGTTCGCACTGCGAACCAATAATATATTATATTATATTATATTATTGGACTCTGGTG
541 CGAACGCCGAGGTGAGCCAATCGGATATGGCGATATGTTATCACGTGACATGTACCGCCC
601 CAAATTCGCACTTGAGTGTTGGGGGTACATGTGGGGCGGCTCGGCTCTTGTGTATAAAA
661 GAGCGGCGGTTGCGAGGTTCCTTCTCTCTTCGCGATGCTCTCTCAGAATGGCACGGCCGA
721 TCCCCCATATATTTCCTGAAGGAACGCATAGCTAGGCGACGAACGAGCTGAATTTCTCCC
781 TTCATCAAATAAGTAATAAA
```

AVIAN HERPESVIRUS-BASED LIVE RECOMBINANT AVIAN VACCINE, IN PARTICULAR AGAINST GUMBORO DISEASE

BACKGROUND OF THE INVENTION

1. Field of the Invention

The present invention relates to vaccines for avian use which are based on live recombinant avian herpesviruses namely, and in particular, Marek's disease virus (MDV) and, more especially, HVT virus (herpesvirus of turkey), in which has been inserted, by genetic recombination, at least one nucleotide sequence which encodes, and expresses, an antigenic polypeptide of an avian pathogen under conditions which ensure an immunization leading to efficient protection of the vaccinated animal against the said pathogen. It also applies to infectious laryngotracheitis virus (ILTV) and to duck herpesvirus.

2. Prior Art

A certain number of recombinant avian viral vectors have already been proposed for the purpose of vaccinating birds against avian pathogens, especially viral pathogens, including the viruses of Marek's disease (MDV), of Newcastle disease (NDV), of infectious laryngotracheitis (ILTV), of Gumboro disease (infectious bursal disease, IBDV), of infectious bronchitis (IBV) and of avian anemia (CAV).

The viral vectors employed include avipox viruses, in particular fowlpox (EP-A-0 517 292; H.-G. Heine et al., Arch. Virol. 1993, 131: 277–292; D. B. Boyle et al., Veterinary Microbiology 41, 1994, 173–181; C. D. Bayliss et al., Arch. Virol. 1991, 120: 193–205), Marek's viruses, especially serotypes 2 and 3 (HVT) (WO-A-87 04463; WO-A-89 01040; WO-A-93 25665; EP-A-0 513 921; J. McMillen, Poultry Condemnation Meeting, October 1994, 359–363; P. J. A. Sondermeijer et al., Vaccine 1993, 11, 349–357; R. W. Morgan et al., Avian Diseases 36: 858–870, 1992 and 37: 1032–1040, 1993) and also ILTV virus and avian adenovirus.

When used for vaccination, these recombinant viruses induce varying, in general weak or partial, levels of protection, even if a substantial degree of protection can be demonstrated in rare specific instances.

Gumboro disease virus, or IBDV virus, is one of the most difficult to protect against using live recombinant avian vaccines. Thus, although effective conventional live attenuated or inactivated vaccines against this disease are available, no live recombinant vaccine has yet been demonstrated to have suitable efficacy.

The genome of Gumboro disease virus consists of a double-stranded RNA. The largest segment (segment A) encodes a polyprotein of 115 kDa, which is secondarily cleaved into three proteins, VP2 (41 kDa), VP4 (28 kDa) and VP3 (32 kDa). VP4 would appear to be a protease which is involved in the maturation of the 115 kDa polyprotein. The position of the cleavage site between VP2 and VP4 has only been determined approximately (M. Jagadish, J. Virol. 1988, 62, 1084–1087). The VP2 protein is an immunogen which induces neutralizing antibodies and protection against Gumboro disease.

It has already been proposed to insert genes encoding immunogenic IBDV proteins into various live vectors: EP-A-0 517 292 (insertion of sequences encoding VP2 or the polyprotein into an avipox); C. D. Bayliss 1991, H.-G. Heine 1993 and D. B. Boyle 1994 above (VP2 in fowlpox); WO-A-90 02802 (MDV vector); WO-A-90 02803 (HVT and ILTV vectors); French patent applications Nos. 90 03105, 90 11146 and 92 13109 (HVT vector).

Patent applications WO-A-89 01040 and WO-A-93 25655 describe the construction of an HVT avian viral vector in which a sequence permitting expression of the native VP2 protein of the IBDV virus, known as the prime polypeptide candidate for vaccinating against Gumboro disease, has been inserted into the XhoI insertion site which is present in the HVT UL43 gene, identified in the first of these two applications under the designation BamHI fragment #16, under the control of an exogenous promoter. However, despite obtaining a native VP2 protein, it was not possible to obtain any induction of neutralizing antibodies or protection when the vaccinated animals were challenged with virulent IBDV virus.

This is why the idea of using this site has not been pursued, and it has instead been proposed, in WO-A-93 25655, to insert sequences which permit expression of the IBDV VP2 protein, still under the control of an exogenous promoter, into the unique StuI site of the HVT US2 gene. The expression of the VP2 protein was characterized in vitro, without demonstrating any activity or protection in vivo. It may also be noted that insertions of other genes in this US2 StuI site, namely the MDV gB gene, accompanied or not accompanied by the gC gene (termed gA in this earlier document), and linked to its own promoter, or the gB and gC genes together with the F gene of NDV linked to the immediate early (IE) HCMV promoter, or the gB and gC genes together with the NDV HN gene linked to the PRY promoter gX, have made it possible to obtain protection against challenges with the corresponding virulent viruses. Similarly, protection is reported for constructs in which the gB and gD genes of the ILTV virus are inserted into this same site. These results contrast with the total absence of protection, and the naive assumptions, in application WO-A-89 01040.

Various promoters, including those which are generally available commercially, have been used in the different constructs of the prior art, including the PRV gX promoter, the HCMV IE (human CMV immediate early) promoter, the herpes simplex alpha-4 promoter, the FPV P.E/L promoter (fowlpox promoter) (H. Heine et al., 1993, Arch. Virol. 131, 277–292), P7.5 (C. Bayliss et al., 1991, Arch. Virol. 120, 193–205) and P11 (D. Boyle et al., 1994, Vet. Microb. 41, 173–181) promoters of vaccinia virus, originating from the LTR sequence of RSV (Rous sarcoma virus) and the early SV40 promoter, as well as the MDV or HVT promoters, such as the promoters of the genes gB, gC, TK, RR2, etc., without any consistent pattern emerging, especially as regards constructs in HVT. The sequences of certain promoters can inhibit the replication of the HVT or MDV recombinant vectors (D. R. Marshall et al., J. Meth. 1992, 40, 195–204 and Virology 1993, 195, 638–648). Among the cited promoters, a certain number, such as, for example, SV40, LTR RSV and PRV gX, have displayed a certain degree of efficacy, as have certain native promoters of certain genes of the Marek's viruses, especially serotype 3.

There still exists, therefore, due to the technical and economic constraints imposed by inactivated vaccines and the safety problems associated with the use of live attenuated vaccines, the need for a live recombinant vaccine which is effective against Gumboro disease virus (IBDV). Such a vaccine, which is based on a recombinant HVT vector and which would be truly effective against Gumboro disease, could, moreover, open the way to vaccines which were very effective against other avian diseases, in view of the fact that it is particularly difficult to achieve protection against Gumboro disease.

SUMMARY OF THE INVENTION

The invention has now, surprisingly, made it possible to develop an HVT vector-based live recombinant vaccine in which at least one sequence encoding the IBDV VP2 protein is inserted and which ensures total protection of animals against Gumboro disease, namely protection against death and against lesions of the bursa of Fabricius. Furthermore, the efficacy of this vaccine proves to be such that it has become possible even to vaccinate one-day-old chicks effectively and without any secondary effects (especially the absence of local lesions at the point of injection and the absence of any lesion in the bursa of Fabricius), something which was not even possible using inactivated vaccines. In addition, the doses which are required are astonishingly low.

The subject of the present invention is a live recombinant avian vaccine which comprises, as vector, an avian herpesvirus which includes at least one nucleotide sequence which encodes, and expresses, an antigenic polypeptide of an avian pathogen and which is inserted in the UL43 gene under the control of the CMV immediate early promoter.

The avian herpesviruses according to the invention are preferably the Marek's disease viruses, especially HVT, infectious laryngotracheitis virus ILTV and duck herpesvirus. The Marek's disease viruses and, more particularly, HVT virus are preferred.

Insertion into the UL43 gene is understood to mean both simple insertion into this site without deleting it and insertion following total or partial deletion. Insertion after partial deletion is preferred.

CMV immediate early (IE) promoter is understood to mean the fragment given in the examples as well as its subfragments which retain the same promoter activity.

The CMV IE promoter can be the human promoter (HCMV IE) or the murine promoter (MCMV IE), or else a CMV IE promoter of different origin, for example from the rat or from the guinea-pig.

The nucleotide sequence which is inserted into the Marek vector in order to be expressed can be any sequence encoding an antigenic polypeptide of an avian pathogen, which polypeptide is capable, once expressed under the favorable conditions procured by the invention, of ensuring an immunization which leads to effective protection of the vaccinated animal against the pathogen. It will be possible, therefore, under the conditions of the invention, to insert nucleotide sequences which encode antigens of interest for a given disease. In particular, the characteristics of the recombinant according to the invention permit vaccination in ovo and vaccination of 1-day old-chicks, as well as vaccination of older chicks and adults.

The typical case of the invention is the insertion of a nucleotide sequence which expediently encodes the VP2 polypeptide of the IBDV virus. In this way, a live recombinant vaccine is obtained which ensures, in addition to protection against Marek's disease, total protection against Gumboro disease. If desired, a sequence encoding another IBDV antigen, such as VP3 or even the polyprotein VP2+VP4+VP3, can also be inserted, with these other possibilities not being preferred.

The recombinant vaccine against Gumboro disease will preferably be administered within the range of from 10 to $10^4$ PFU/dose, more especially of from $10^2$ to $10^3$ PFU/dose, and even between 10 and $10^2$ PFU/dose, approximately.

Other preferred cases of the invention are the insertion of nucleotide sequences which encode antigens of Marek's disease virus, in particular genes gB, gC, and gH+gL (WO-A-90 02803), of Newcastle disease virus, in particular genes F and HN, of infectious bronchitis virus (IBV), in particular genes S and M (M. Binns et al., J. Gen. Virol. 1985, 66, 719–726; M. Boursnell et al., Virus Research 1984, 1, 303–313), of avian anemia virus (CAV), in particular VP1 (52 kDa)+VP2(24 kDa) (N. H. M. Noteborn et al., J. Virol. 1991, 65, 3131–3139) and of infectious laryngotracheitis virus (ILTV), in particular genes (WO-A-90 02802), gC, gD and gH+gL.

The doses will preferably be the same as those which are indicated for the Gumboro vaccine.

According to an advantageous development of the invention, the CMV IE promoter is linked to another promoter in a head-to-foot orientation, making it possible to insert two nucleotide sequences into the insertion site, one under the control of the CMV IE promoter and the other under the control of the linked promoter. This construct is remarkable for the fact that the presence of the CMV IE promoter, and especially of its enhancer part, activates the transcription which is induced by the linked promoter. A preferred linked promoter is the Marek 1.8 RNA promoter, whose transcriptional activity is found to be increased 4.4 fold under these conditions.

The typical case of the invention is a vaccine comprising a nucleotide sequence which encodes IBDV VP2 under the control of CMV IE and a nucleotide sequence which encodes an antigen of another avian disease, especially those cited above, under the control of another promoter.

Two CMV IE promoters of different origins can also be arranged in a head-to-foot orientation.

It will also be possible to use the 1.8 RNA promoter on its own in place of the CMV IE promoter, especially for vaccines against Marek's disease, Newcastle disease, infectious laryngotracheitis, infectious bronchitis and avian anemia.

The present invention also relates to a multivalent vaccine formulation which comprises, in a mixture or to be mixed, at least two live recombinant avian vaccines such as defined above, with these vaccines containing different inserted sequences, especially from different pathogens.

The present invention also relates to a method of avian vaccination which comprises administering a live recombinant vaccine or a multivalent vaccine formulation such as defined above. It particularly relates to such a method for vaccinating in ovo, for vaccinating chicks of 1 day of age or older, and for vaccinating adults.

BRIEF DESCRIPTION OF THE DRAWING FIGURES

The invention will now be described in more detail with the aid of non-limiting exemplary embodiments and by reference to the drawings in which: List of the drawings and of the sequences of the constructs in the UL43 site FIG. 1: Sequence of the HVT $U_s$ gI region FIG. 2: Construction of the plasmids pRD022 and pRD027

FIG. 3: Construction of the plasmids pRD023 and pRD029

FIG. 4: plasmid pCMVβ

FIG. 5: plasmid pEL022

FIG. 6: plasmid pEL023

FIG. 7: plasmid pEL024

FIG. 8: plasmid pEL025

FIG. 9: Sequence of the HVT BamHI M fragment and ORF UL43

FIG. 10: Construction of the plasmids pMB010 and pMB016

FIG. 11: plasmid pEL026

FIG. 12: plasmid pEL027

FIG. 13: plasmid pEL042

FIG. 14: plasmid pCD002

FIG. 15: plasmid pCD009

FIG. 16: plasmid pEL068

FIG. 17: plasmid pEL070

FIG. 18: plasmid pEL072

FIG. 19: plasmid pCD011

FIG. 20: plasmid pCD012

FIG. 21: Sequence of the NDV HN gene

FIG. 22: plasmid pEL028

FIG. 23: plasmid pEL029bis

FIG. 24: plasmid pEL030

FIG. 25: plasmid pEL032

FIG. 26: plasmid pEL043

FIG. 27: plasmid pEL033

FIG. 28: plasmid pEL034

FIG. 29: plasmid pEL044

FIG. 30: 1.8 kbp RNA promoter sequence

FIG. 31: plasmid pBS002

FIG. 32: plasmid pEL069

FIG. 33: plasmid pEL080

FIG. 34: plasmid pEL081

FIG. 35: plasmid pEL082

FIG. 36: plasmid pEL096

List of the SEQ ID sequences of the constructs in the UL43 site

SEQ ID NO. 1 Oligonucleotide RD045

SEQ ID NO. 2 Oligonucleotide pBRPst−

SEQ ID NO. 3 Sequence of the HVT $U_s$ gI region

SEQ ID NO. 4 Oligonucleotide RD048

SEQ ID NO. 5 Oligonucleotide RD049

SEQ ID NO. 6 Sequence of the HVT BamHI M fragment

SEQ ID NO. 7 Oligonucleotide MB014

SEQ ID NO. 8 Oligonucleotide MB015

SEQ ID NO. 9 Oligonucleotide MB070

SEQ ID NO. 10 Oligonucleotide MB071

SEQ ID NO. 11 Oligonucleotide CD001

SEQ ID NO. 12 Oligonucleotide CD002

SEQ ID NO. 13 Oligonucleotide CD003

SEQ ID NO. 14 Oligonucleotide CD004

SEQ ID NO. 15 Sequence of the NDV EN gene

SEQ ID NO. 16 Oligonucleotide EL071

SEQ ID NO. 17 Oligonucleotide EL073

SEQ ID NO. 18 Oligonucleotide EL074

SEQ ID NO. 19 Oligonucleotide EL075

SEQ ID NO. 20 Oligonucleotide EL076

SEQ ID NO. 21 Oligonucleotide EL077

SEQ ID NO. 22 Sequence of the 1.8 kbp RNA promoter

SEQ ID NO. 23 Oligonucleotide MB047

SEQ ID NO. 24 Oligonucleotide MB048

SEQ ID NO. 25 Oligonucleotide MB072

DESCRIPTION OF THE PREFERRED EMBODIMENTS

Figure 2:
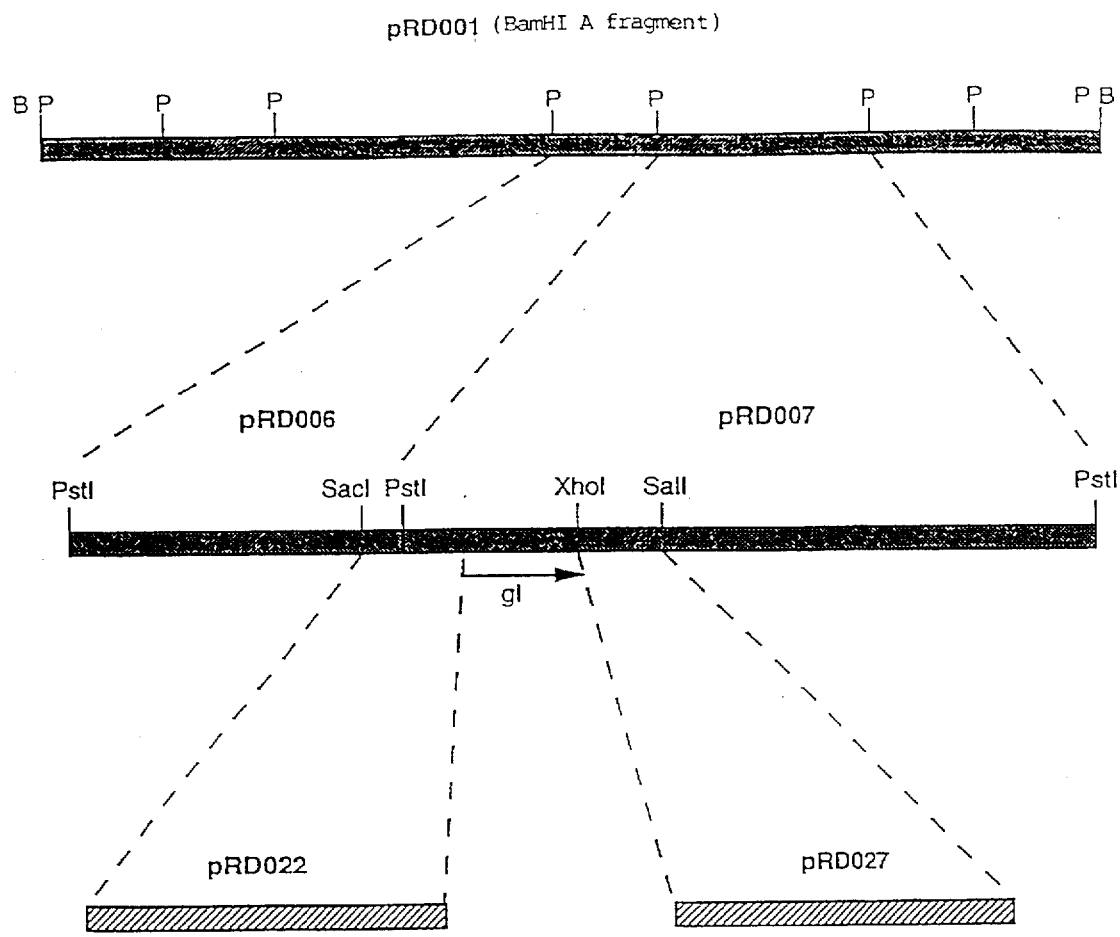

All the plasmid constructions were carried out using standard molecular biological techniques described by Sambrook J. et al. (*Molecular Cloning: A Laboratory Manual*. 2nd Edition. Cold Spring Harbor Laboratory. Cold Spring Harbor. N.Y. 1989). All the restriction fragments which were employed for the present invention were isolated using the "Geneclean" kit (BIO101 Inc. La Jolla, Calif.).

The virus which was used as parent virus is the turkey herpesvirus (HVT) strain FC126, which was isolated by Dr. Witter of the Regional Poultry Research Laboratory (USDA, East Lansing, Mich.) in a 23-week old flock of turkeys (Witter R. L. et al. Am. J. Vet. Res. 1970. 31. 525–538). The conditions for culturing this virus are those described elsewhere (French patent application 90 03105).

EXAMPLE 1

Extraction of the DNA of Marek's disease Virus

The whole blood of a chicken which was challenged at 7 days with the strain MDV RB1B is collected with a syringe on to anticoagulant (100 IU/ml heparin solution) at 14 days after infection. The blood is then centrifuged at 30 g for 15 minutes and at ambient temperature. The plasma as well as the buffy coat are removed and diluted in sterile PBS up to a final volume of 10 ml. After centrifuging at 150 g for 15 minutes, the cell pellet is resuspended in 2 ml of 199 culture medium (Gibco-BRL Cat#042-01183M) containing 2% fetal calf serum (FCS). The total DNA of the infected lymphocytes is then extracted using the technique described by R. Morgan et al. (Avian Diseases. 1990. 34. 345–351) and can be used directly as a template for PCR experiments. In order to clone genomic fragments of the MDV virus, the RB1B strain was cultured on CEC and the viral DNA was prepared from viral particles which were purified as described by Lee Y. et al. (J. Gen. Virol. 1980. 51. 245–253).

EXAMPLE 2

Preparation of the Genomic DNA of the MCMV (Mouse Cytomegalovirus) Virus

The Smith MCMV virus strain was obtained from the American Type Culture Collection, Rockville, Md., USA (ATCC No. VR-194). This virus was cultured on Balb/C mouse embryo cells, and the viral DNA of this virus was prepared as described by Ebeling A. et al. (J. Virol. 1983. 47. 421–433).

EXAMPLE 3

Preparation of the Genomic DNA of the HVT Virus for the Transfection Experiments The viral DNA which was used for the transfection experiments was prepared, in accordance with the technique described by R. Morgan et al. (Avian Diseases. 1990. 34. 345–351), using a culture of secondary CEC (CEC II) which was infected with the HVT virus FC126 strain.

Construction of the recombinant viruses

EXAMPLE 4

Construction and Isolation of vHVT1

The construction of the donor plasmid pGH010, and the isolation and purification of the recombinant virus vHVT1 were described in French patent application 92.13109. This recombinant HVT virus contains the gene encoding the VP2 capsid protein of Gumboro disease virus (IBDV virus) placed under the control of the promoter of the RR2 gene of the HVT virus. In this recombinant virus, the VP2 gene was inserted in place of the HVT RR2 gene.

EXAMPLE 5

Construction of the Donor Plasmid pEL025 and Isolation of vHVT2

5.1. Construction of the donor plasmid pEL025

The 29 kbp BamHI A fragment of the HVT virus strain FC126 (Igarashi T. et al. Virology. 1989. 70. 1789–1804) was cloned into the BamHI site of the vector pBR322 to give the plasmid pRD001. Plasmid pRD001 was digested with PstI and the 2.8 kbp and 5.7 kbp PstI—PstI fragment were cloned into the PstI site of vector pBR322 to give the plasmids pRD006 and pRD007, respectively. Plasmid pRD006 was digested with PstI and SacI in order to isolate the PstI/SacI fragment of 340 bp (fragment A).

A PCR was carried out using the oligonucleotides:

RD045 (SEQ ID NO. 1) 5' TGCTGGTACCGTCGA-CAAGCTTGGATCCGTGCAGATAACACG-TACTGGC 3' pBRPst– (SEQ ID NO. 2) 5' CATG-TAACTCGCCTTGATC 3' and the pRD007 template, in order to obtain a fragment of 550 bp (positions 339 to 831 in FIG. 1 (SEQ ID NO. 3) (positions 6491 to 6980 in the HVT $U_s$ sequence (Zelnik V. et al. J. Gen. Virol. 1993. 74. 2151–2162). The PCR fragment of 520 bp was then digested with KpnI and PstI in order to isolate a PstI/KpnI fragment of 520 bp (fragment B). Fragments A and B were ligated both at once to the vector pBS-SK+ (Stratagene), which had previously been digested with KpnI and SacI, to give the plasmid pRD022 (FIG. 2). Plasmid pRD007 was digested with SalI and XhoI in order to isolate the SalI/XhoI fragment of 730 bp (positions 1876 to 2608 in SEQ ID NO. 1) (positions 6491 to 6980 in the HVT $U_s$ sequence (Zelnik V. et al. J. Gen. Virol. 1993. 74. 2151–2162). This fragment was cloned into the SalI site of vector pBS-SK+ to give the plasmid pRD027 (FIG. 2).

A synthetic double-stranded oligonucleotide was obtained by hybridizing the two following oligonucleotides:

RD048 (SEQ ID NO. 4) 5' GATCCAGCTGAAT-TCAGCTA 3'

RD049 (SEQ ID NO. 5) 5' AGCTTAAGCTGAAT-TCAGCTG 3'

Figure 3:
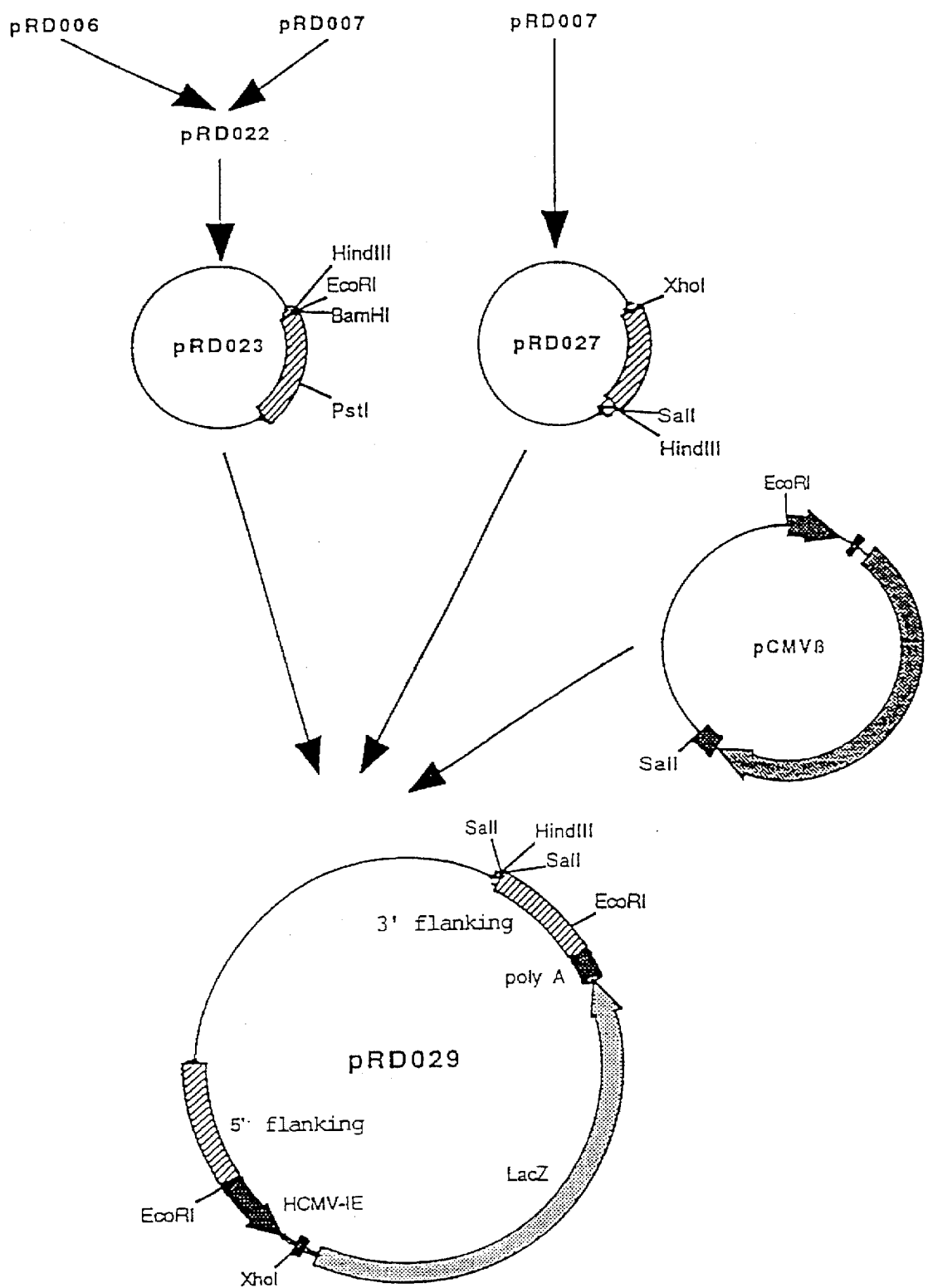
Figure 4:
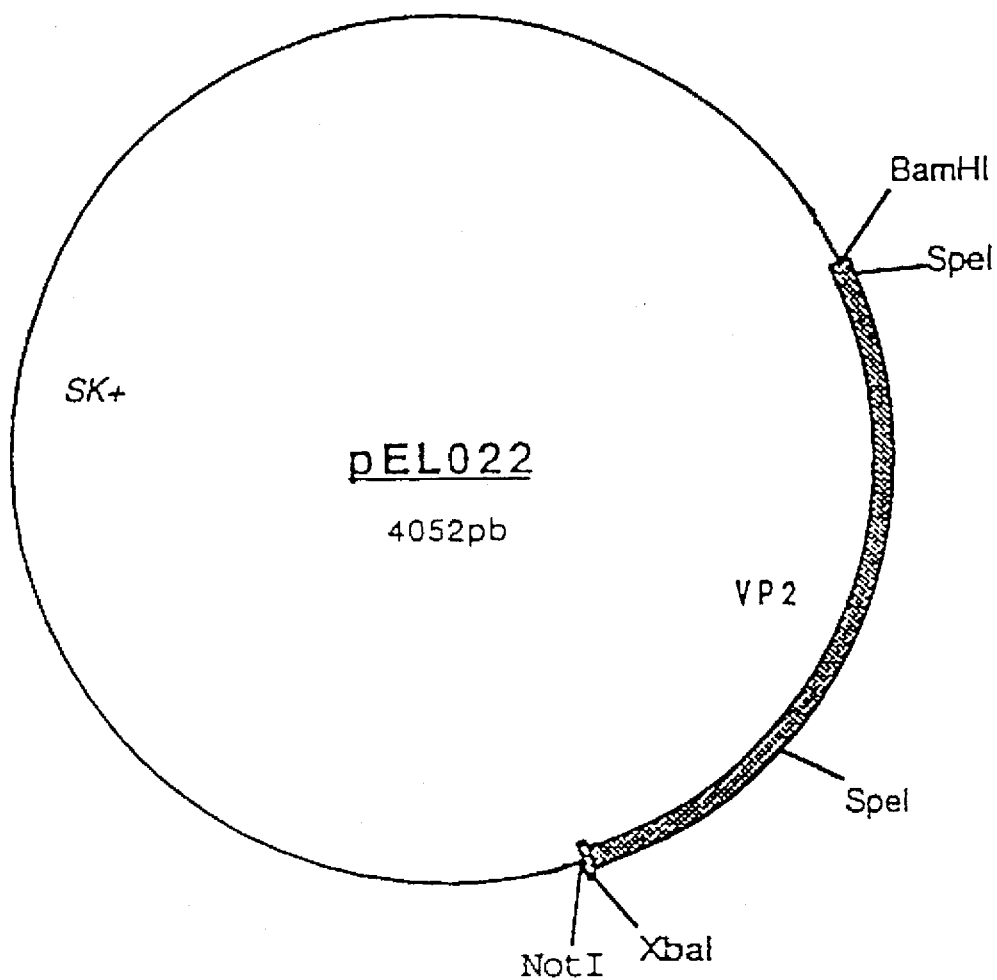

This oligonucleotide was cloned between the BamHI and HindIII sites of plasmid pRD022 to give the plasmid pRD023 (FIG. 3). The plasmid pCMVβ (Clontech Cat#6177-1) (FIG. 4) was digested with EcoRI and SalI in order to isolate the EcoRI/SalI fragment of 4500 bp which contains the HCMV-IE=lacZ expression cassette (fragment C). Plasmid pRD027 was digested with HindIII and XhoI in order to isolate the HindIII/XhoI fragment of 730 bp (fragment D). Fragments C and D were ligated both at once to plasmid pRD023, which had previously been digested with EcoRI and HindIII. Give the plasmid pRD029 of 8973 bp (FIG. 3). This plasmid contains the HCMV-IE=lacZ expression cassette in the gI site (complete deletion) of the HVT virus.

Figure 5:
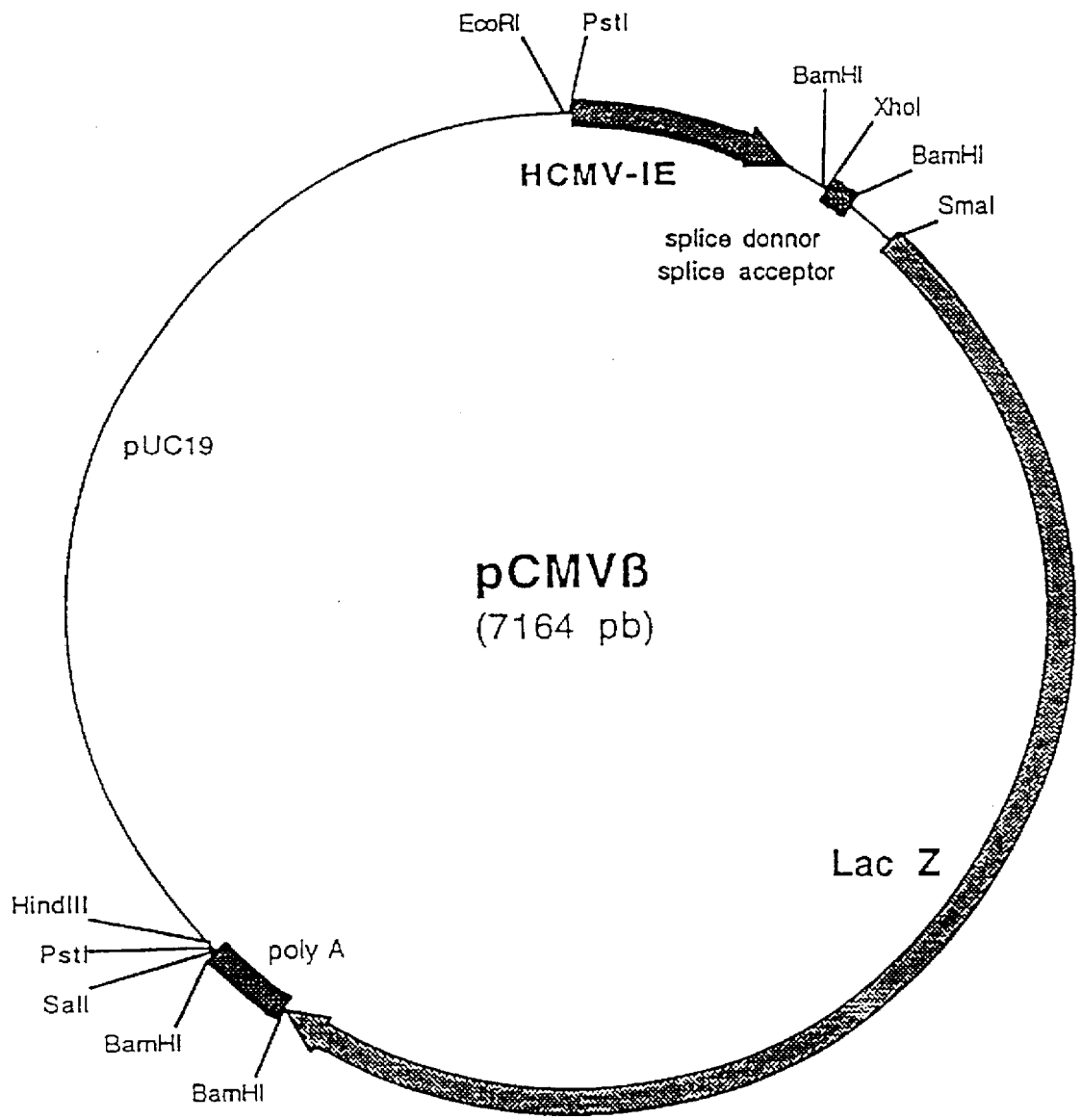
Figure 6:
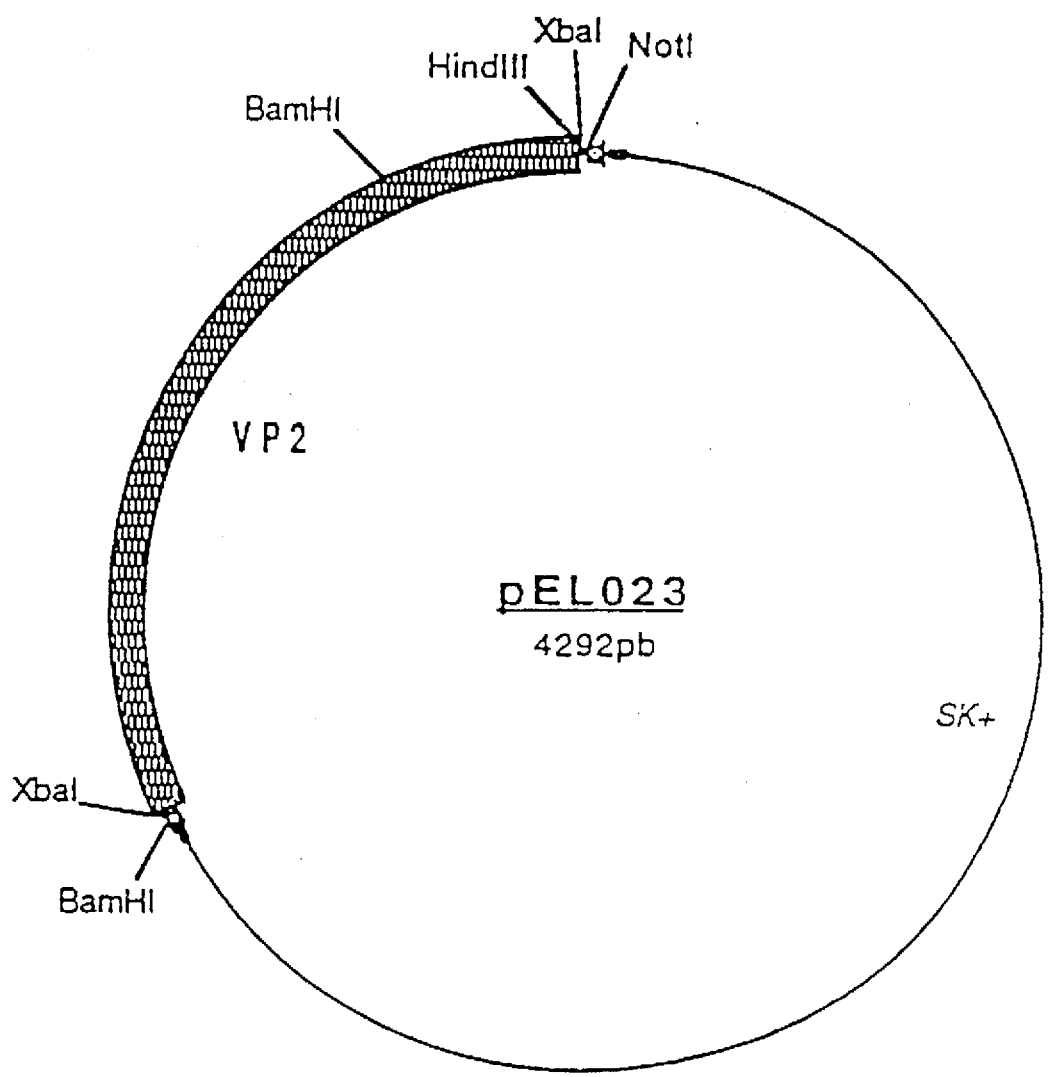
Figure 7:
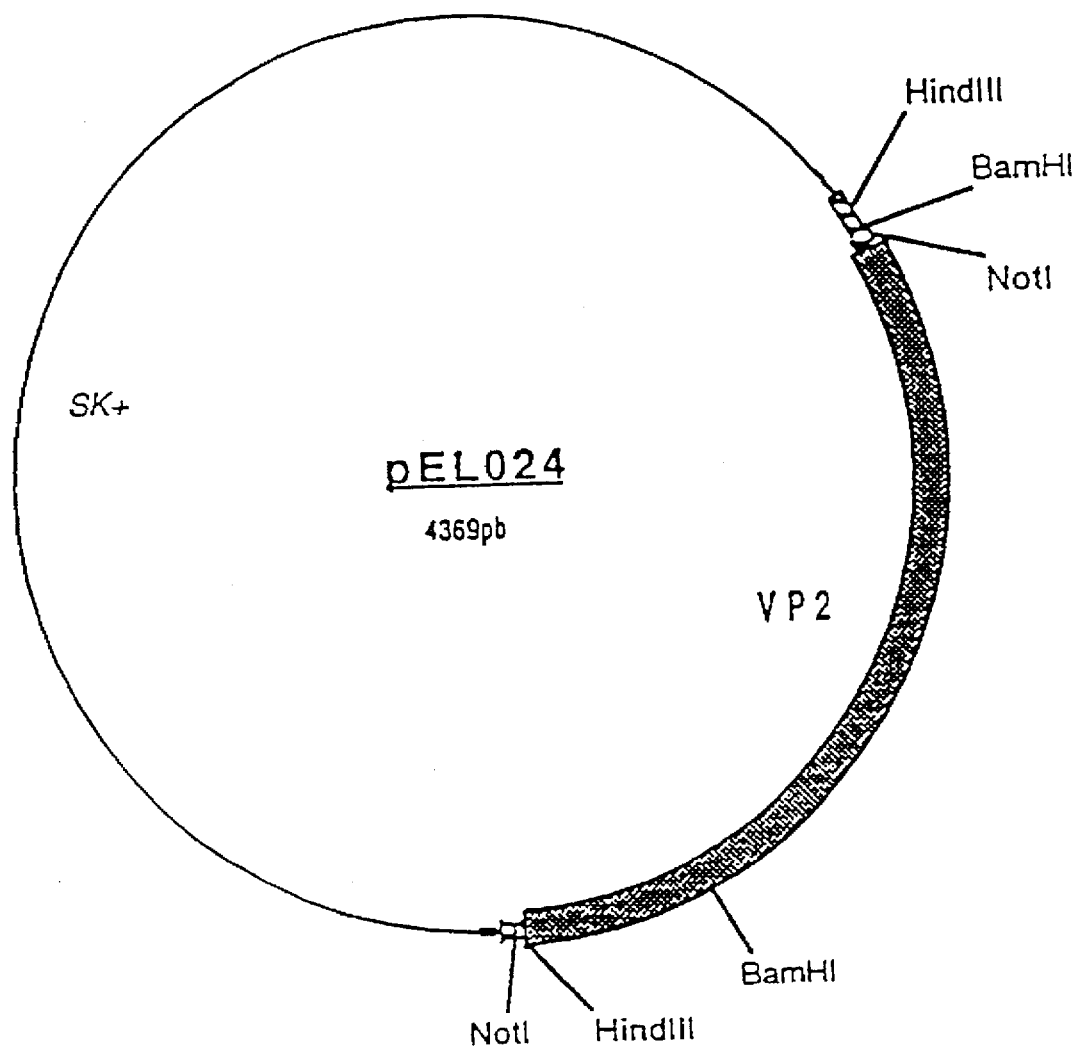
Figure 8:
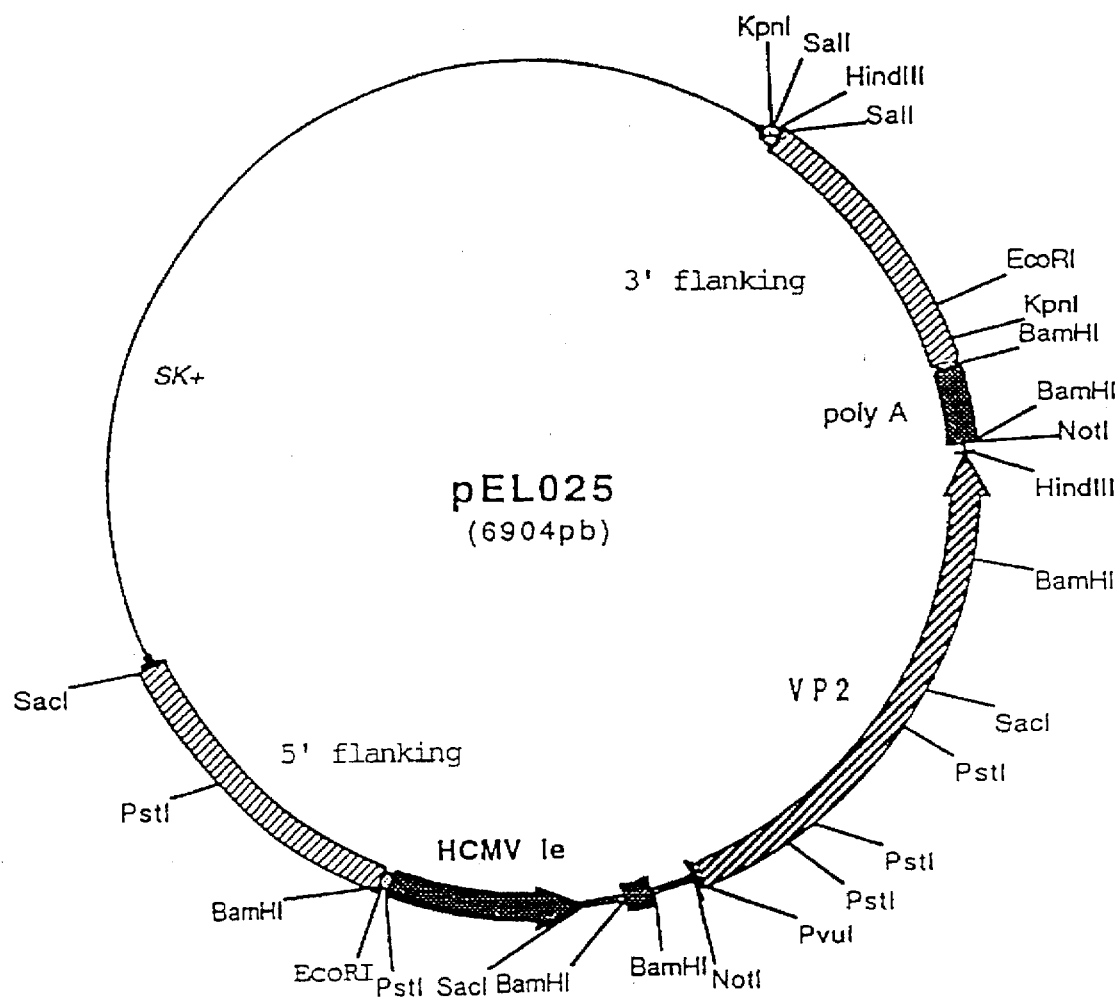

The plasmid pEL004 (=plasmid pGH004 described in French patent application 92.13109), which contains the IBDV VP2 gene in the form of a BamHI/HindIII cassette, was digested with BamHI and XbaI in order to isolate the BamHI/XbaI fragment (truncated VP2 gene) of 1104 bp. This fragment was cloned into vector pBS-SK+ (Stratagene), which had previously been digested with XbaI and BamHI, to give the plasmid pEL022 of 4052 bp (FIG. 5). Vector pBS-SK+ was digested with EcoRV and XbaI and then ligated to itself in order to give pBS-SK* (modified). Plasmid pEL004 was digested with KpnI and HindIII in order to isolate the KpnI/HindIII fragment of 1387 bp, which contains the complete IBDV VP2 gene. This fragment was cloned into vector pBS-SK*, which had previously been digested with KpnI and HindIII, to give the plasmid pEL023 of 4292 bp (FIG. 6). Plasmid pEL022 was digested with BamHI and NotI in order to isolate the BamHI/NotI fragment of 1122 bp (fragment A). Plasmid pEL023 was digested with BamHI and NotI in order to isolate the BamHI/NotI fragment of 333 bp (fragment B). Fragments A and B were ligated both at once to vector pBS-SK+, which had previously been digested with NotI and treated with alkaline phosphatase, to give the plasmid pEL024 of 4369 bp (FIG. 7). Plasmid pEL024 was then digested with NotI in order to isolate the NotI/NotI fragment of 1445 bp. This fragment was cloned in plasmid pRD029, which had previously been digested with NotI and treated with alkaline phosphatase, to give the plasmid pEL025 of 6904 bp (FIG. 8).

5.2. Isolation and purification of the recombinant vHVT2

Plasmid pEL025 was digested with SalI to linearize it, then extracted with a phenol/chloroform (19:1) mixture, precipitated with absolute ethanol and taken up once again in sterile water. 24-hour primary CEC cells were then transfected with the following mixture: 1 µg of linearized plasmid pEL025+5 µg of HVT viral DNA in 300 µl of OptiMEM medium (Gibco BRL Cat#041-01985H) and 100 µg of LipofectAMINE diluted in 300 µl of medium (final volume of the medium=600 µl). These 600 µl were then diluted in 3 ml (final volume) of medium and plated out on $3.10^6$ CEC I. The mixture was left in contact with the cells for 5 hours and then removed and replaced with 5 ml of culture medium. The cells were then cultured at 37° C. for 3 days and, after that, they were pronased, mixed with fresh CEC II (3:1 mixture) and replated out 1 96-well plate. This plate was cultured for 3 days and, after that, the cells were pronased, mixed with fresh CEC II and respread on 2 96-well plates, with one initial well giving 2 sister wells. The 96-well plates were cultured until a cytopathic effect appeared. After 72 hours of culture, one of the two 96-well plates was fixed with 95% acetone for 30 minutes and an indirect immunofluorescence (IIF) reaction was carried out using a monoclonal anti-VP2 antibody to screen for plaques expressing the VP2 protein. The "sister" wells of the wells displaying positive plaques in IIF were pronased, mixed with fresh CEC II, and deposited, in limiting dilution, on 96-well plates. After 3 days of culture, the wells displaying a cytopathic effect were pronased, mixed with CEC II, and replated out on 96-well plates, with one initial well giving 2 sister wells. 3 days later, screening took place once again, using IIF as before, for the plaques expressing the VP2 protein on one of the 2 sister plates. In general, 4 consecutive cycles of isolation (harvesting a well, replating out, checking with IIF, subculturing a sister well, etc.) are sufficient to obtain recombinant viruses all of whose progeny display a specific fluorescence. One viral plaque which gave plaques all of which were positive by IIF using a monoclonal anti-VP2 antibody was designated vHVT2. The genomic DNA of this recombinant virus was characterized at the molecular level by conventional PCR and Southern blot techniques using the appropriate oligonucleotides and DNA probes. This recombinant contains a HCMV-IE/IBDV VP2 cassette in place of the gI gene of the HVT virus.

EXAMPLE 6

Construction of the Donor Plasmid pEL042 and Isolation of the vHVT4

6.1. Construction of the donor plasmid pEL042

The BamHI M fragment of 3.3 kbp from the genome of the HVT virus strain FC126 (Igarashi T. et al. Virology.

Figure 10:
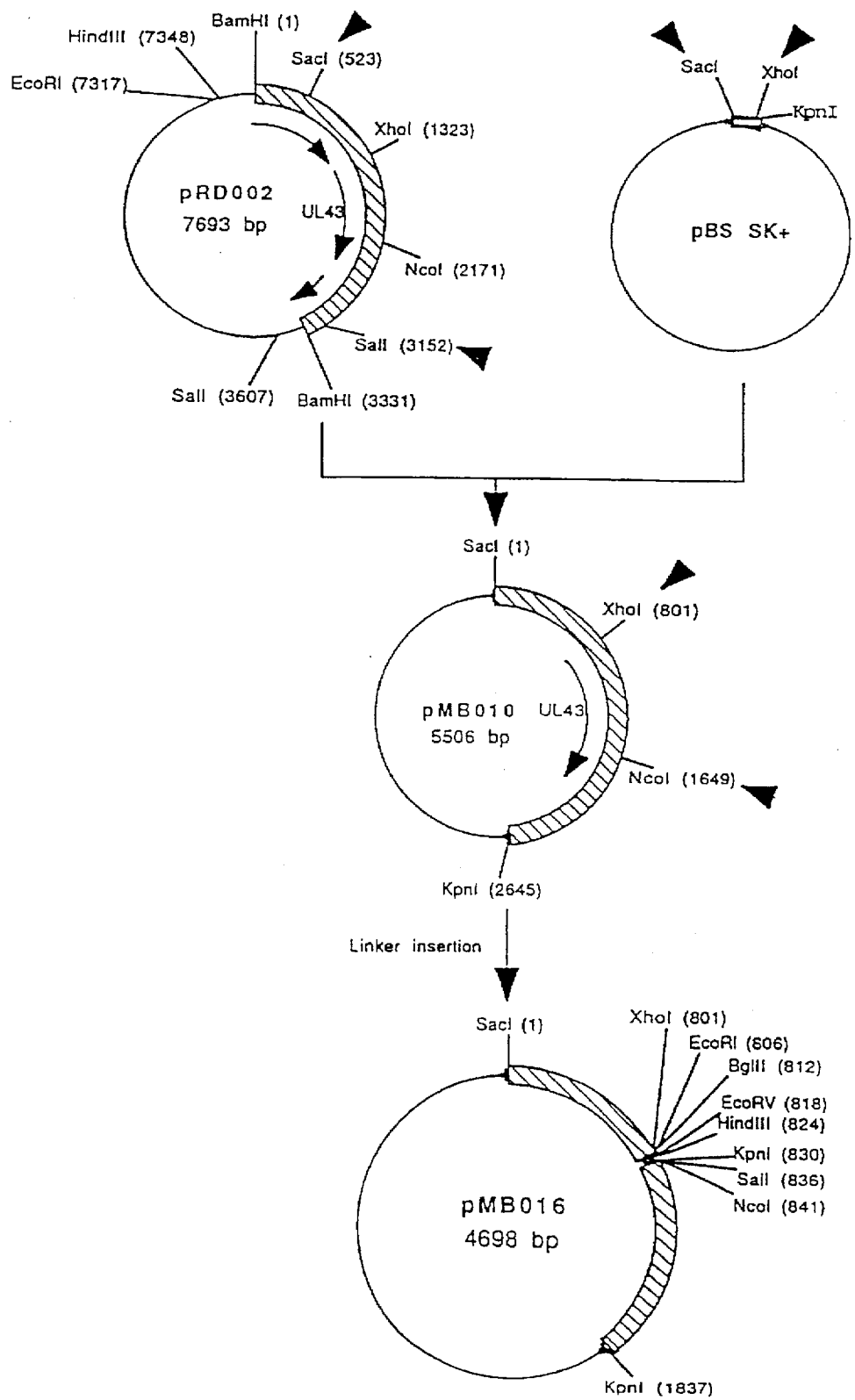

1989. 70. 1789–1804) was cloned into the BamHI site of the vector pBR322 to give the plasmid pRD002. The sequence of the BamHI M fragment was established in its entirety (3336 bp) (SEQ ID NO. 6 and FIG. 9). This sequence contains an ORF encodes a protein which is homologous to the product of the HSV-1 UL43 gene (positions 1306 to 2511) (end of the stop codon) in the sequence SEQ ID NO. 6, FIG. 9). The protein which is theoretically encoded by this ORF is 401 amino acids (aa) in size. Plasmid pRD002 was digested with SacI and SalI in order to isolate the SacI/SalI fragment of 2620 bp. This fragment was ligated into vector pBS-SK+, which had previously been digested with SacI and XhoI, to give the plasmid pMB010 of 5506 bp (FIG. 10). Plasmid pMB010 was then digested with NcoI and XhoI in order to isolate the NcoI/XhoI fragment of 4650 bp. This fragment was ligated to a double-stranded synthetic oligonucleotide which was obtained by hybridizing the 2 following oligonucleotides:

MB014 (SEQ ID NO. 7) 5' TCGAGAATTCAGATCT-GATATCAAGCTTGGTACCGTCGAC 3'

Figure 11:
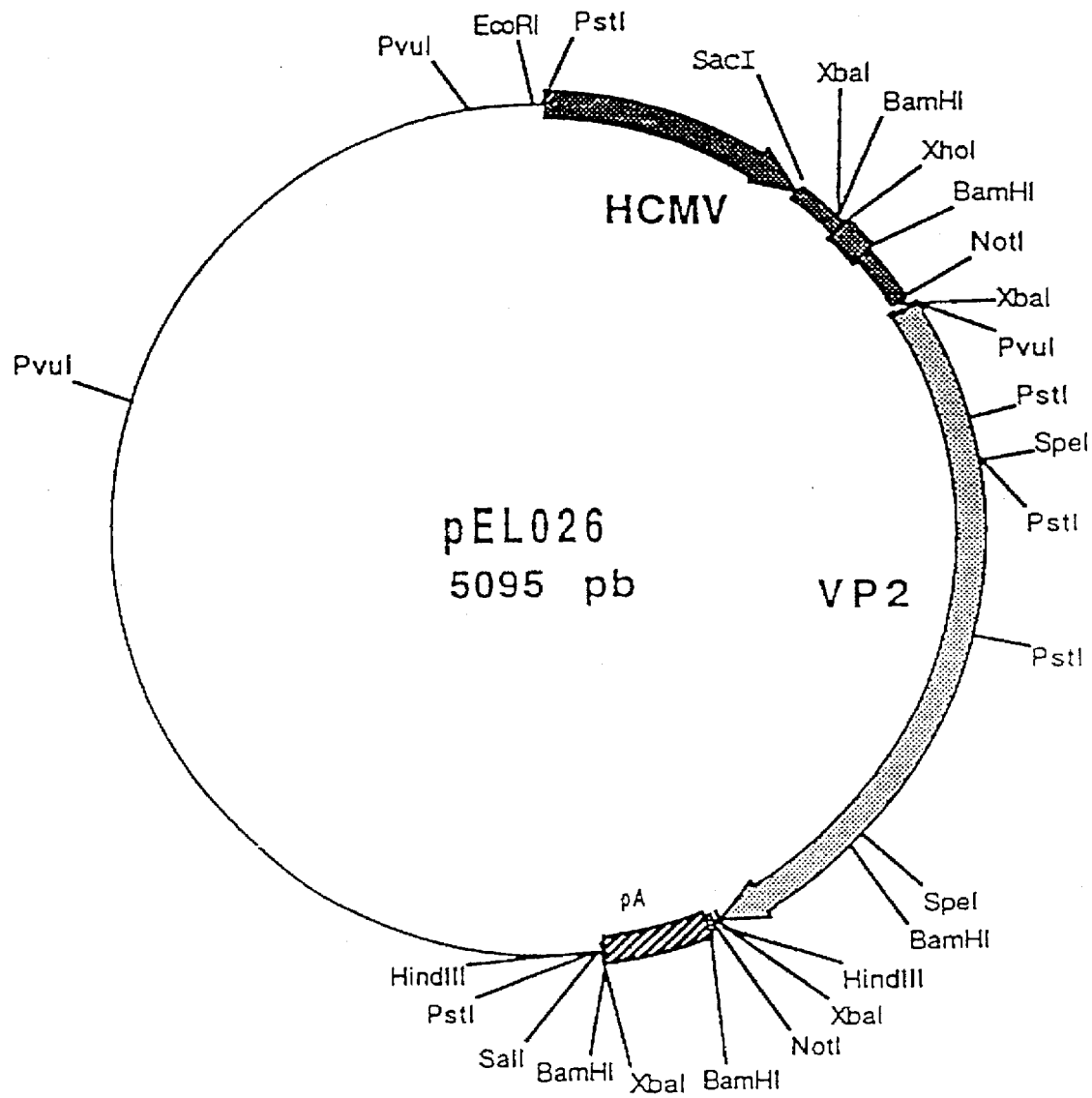
Figure 12:
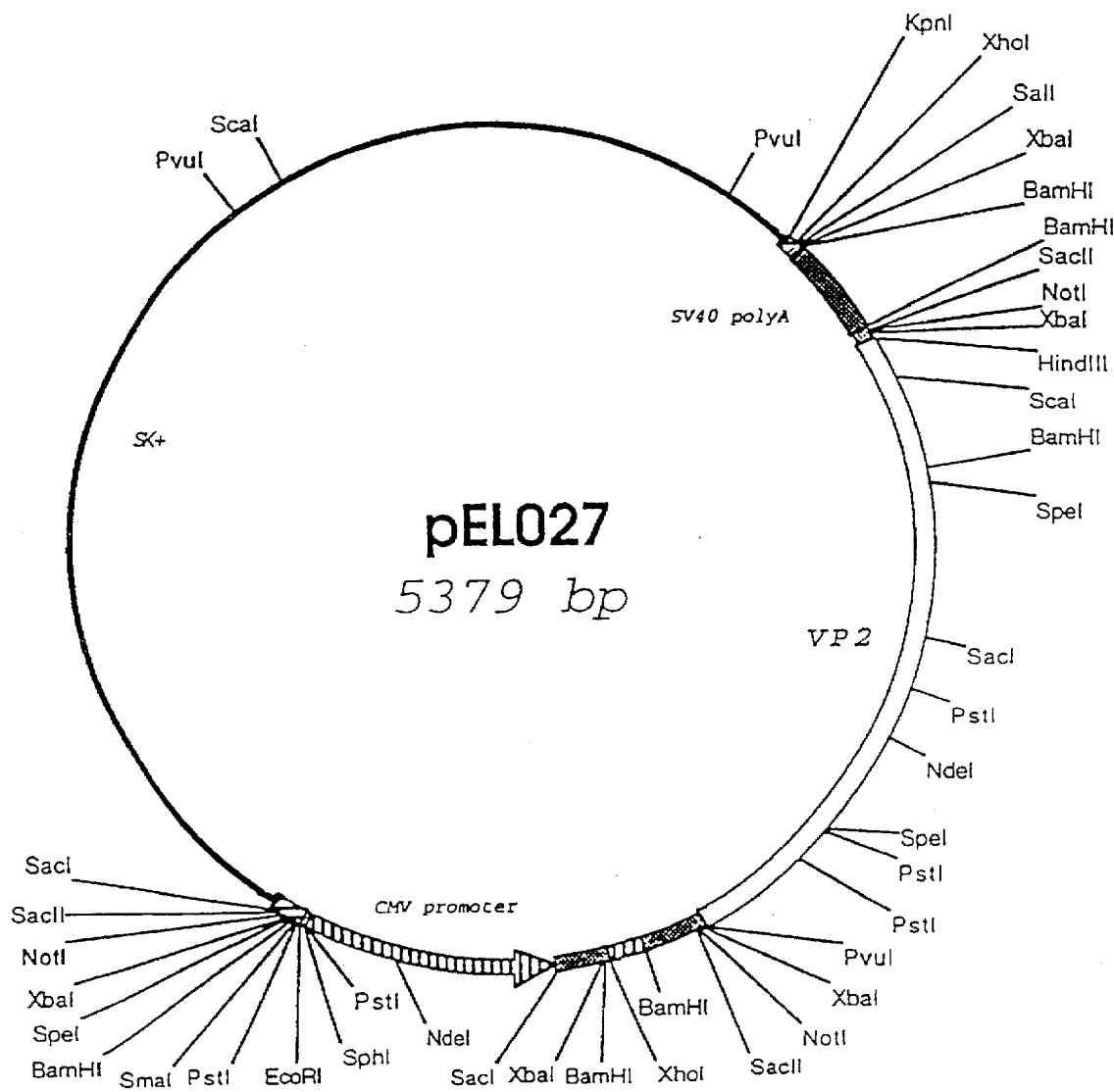
Figure 13:
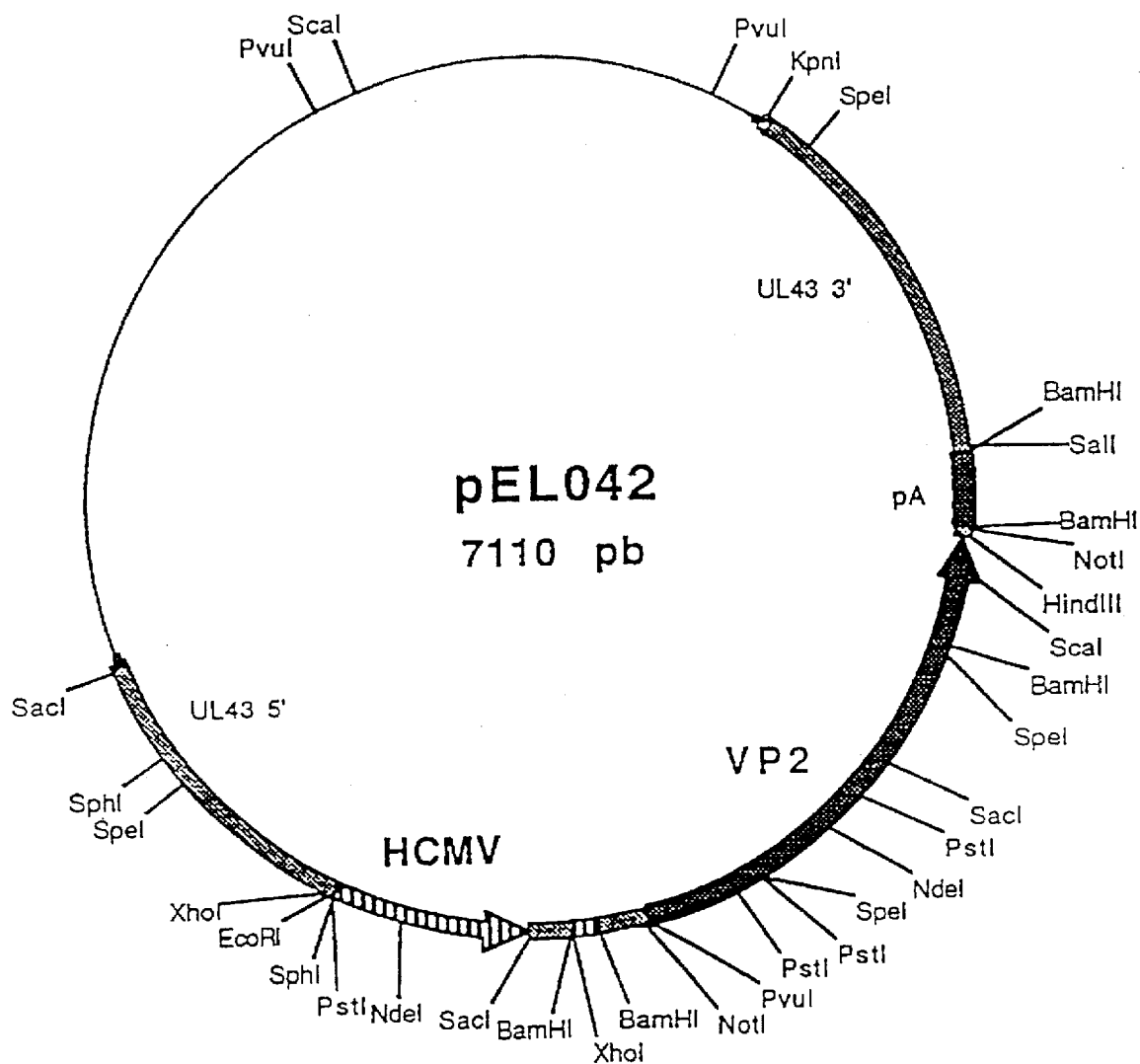

MB015 (SEQ ID NO. 8) 5' CATGGTCGACGGTAC-CAAGCTTGATATCAGATCTGAATTC 3' to give the plasmid pMB016 of 4698 bp (FIG. 10). The inserted oligonucleotide contains restriction sites which allow the insertion of an expression cassette between the two flanking arms of the UL43 locus. The 5' flanking arm has a size of 800 bp (position 523 to position 1323 in the sequence of the BamHI M fragment (SEQ ID NO. 6). The 3' arm has a size of 981 bp (positions 2171 to 3152 in SEQ ID NO. 6). The deletion which is thus obtained in the HVT UL43 gene extends from position 1324 to position 2170 (deletion of 847 nucleotides, that is 282 aa out of a total of 401 aa). Plasmid pEL024 (see Example 5) was digested with NotI in order to isolate the NotI/NotI fragment of 1445 bp. This fragment was ligated to plasmid pCMVβ, which had previously been digested with NotI, to give the plasmid pEL026 of 5095 bp (FIG. 11). Plasmid pEL026 was digested with EcoRI, SalI and XmnI in order to isolate the EcoRI/SalI fragment of 2428 bp. This fragment was ligated to vector pBS-SK+, which had previously been digested with EcoRI and SalI, to give the plasmid pEL027 of 5379 bp (FIG. 12). Plasmid pEL027 was digested with EcoRI, SalI and XmnI in order to isolate the EcoRI/SalI fragment of 2428 bp. This fragment was ligated into plasmid pMB016, which had previously been digested with EcoRI and SalI, to give the plasmid pEL042 of 7110 bp (FIG. 13).

6.2. Isolation and purification of recombinant vHVT4

A cotransfection of CEC II with plasmid pEL042, linearized with KpnI, and HVT viral DNA was carried out as described in Example 5. The conditions for transfection, and for isolating and purifying the recombinant viral plaques which resulted from this cotransfection were those described in Example 5.

A viral plaque which gave plaques all of which were positive by IIF using a monoclonal anti-IBDV VP2 antibody was designated vHVT4. The genomic DNA of this recombinant virus was characterized at the molecular level by the conventional techniques of PCR and Southern blot using the appropriate oligonucleotides and DNA probes.

EXAMPLE 7

Construction of the Donor Plasmid pEL072 and Isolation of vHVT6

Figure 14:
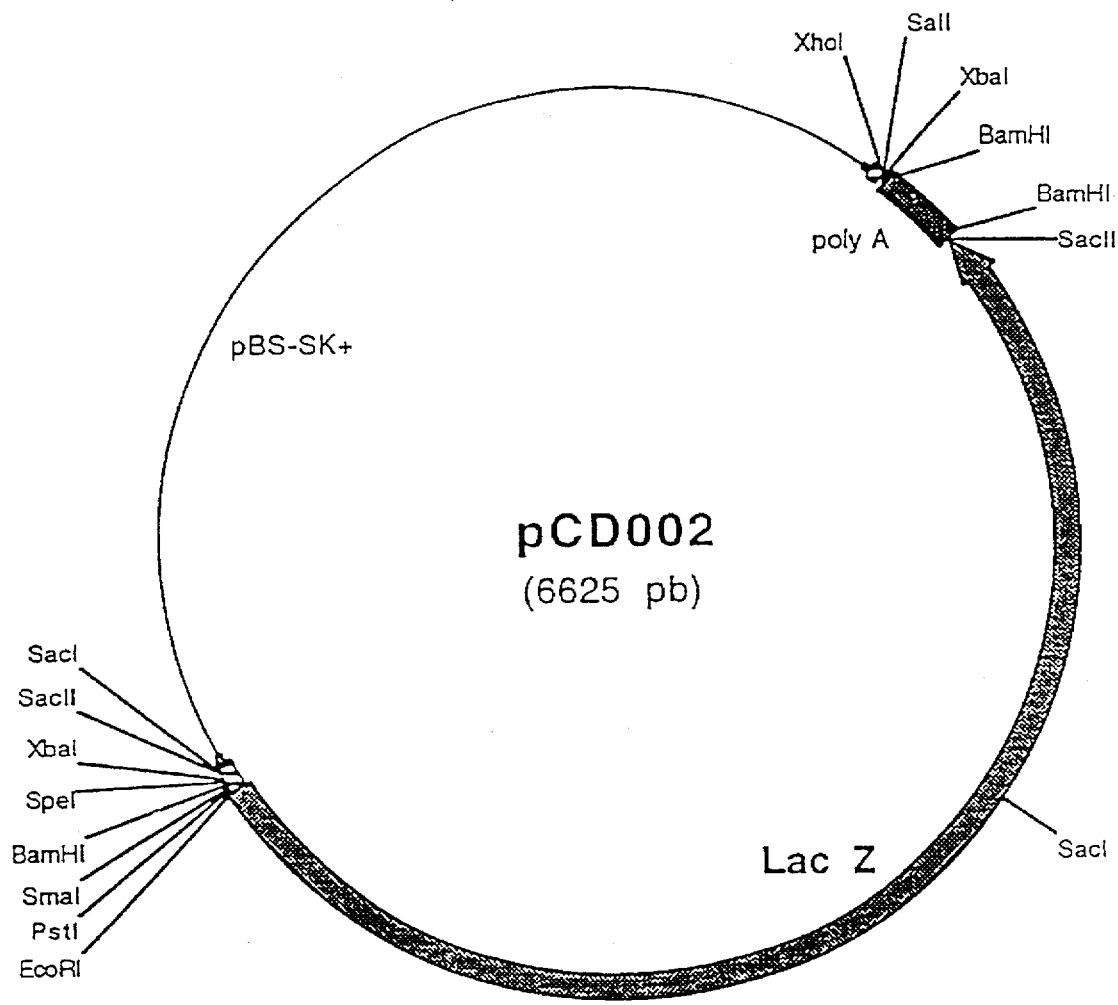
Figure 15:
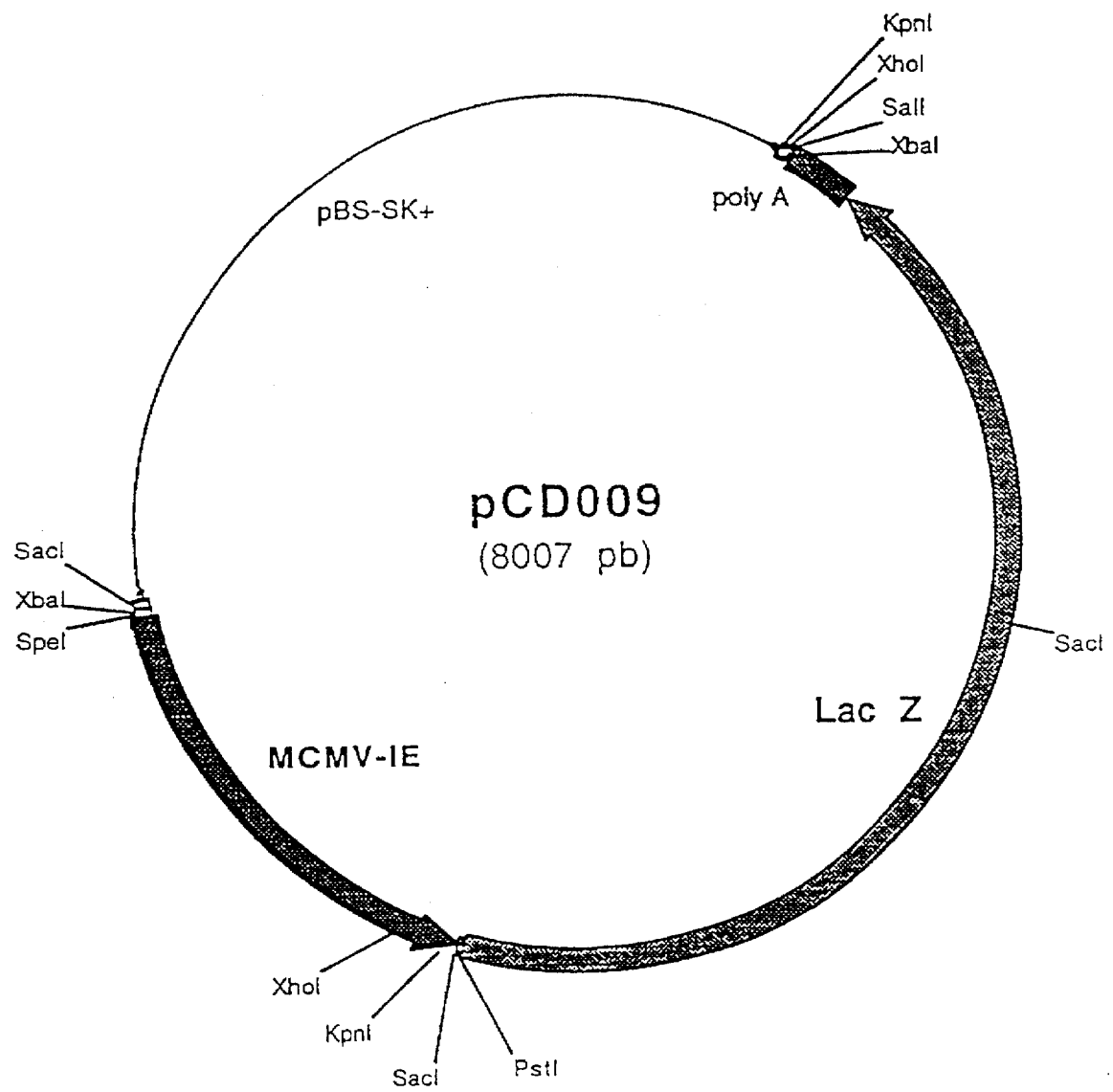

Plasmid pCMVβ (FIG. 4) was digested with SalI and SmaI in order to isolate the SalI/SmaI fragment of 3679 bp, which fragment contained the lacZ gene as well as the polyadenylation signal of the late gene of the SV40 virus. This fragment was inserted into vector pBS-SK+, which had previously been digested with SalI and EcoRV, to give the plasmid pCD002 of 6625 bp (FIG. 14). This plasmid contains the lacZ reporter gene, but no promoter is situated upstream of this gene. The viral genomic DNA of the MCMV virus was prepared as described in Example 2 and digested with PstI in order to isolate the PstI/PstI fragment of 2285 bp. This fragment was cloned into vector pBS-SK+, which had previously been digested with PstI and treated with alkaline phosphatase, to give the plasmid pCD004. Plasmid pCD004 was digested with HpaI and PstI in order to isolate the HpaI/PstI fragment of 1389 bp, which contains the promoter/enhancer region of the immediate early gene of murine cytomegalovirus (MCMV) (Dorsch-Häsler K. et al. Proc. Natl. Acad. Sci. 1985. 82. 8325–8329, and patent application WO-A-87/03905). This fragment was cloned into plasmid pCD002, which had previously been digested with PstI and SmaI, to give the plasmid pCD009 of 8007 bp (FIG. 15).

A double-stranded oligonucleotide was obtained by hybridizing the two following oligonucleotides:

MB070 (SEQ ID NO. 9) 5' CGAATTCACTAGTGTGT-GTCTGCAGGCGGCCGCGTGTGTGTC-GACGGTAC 3'

MB071 (SEQ ID NO. 10) 5' CGTCGACACACACGCG-GCCGCCTGCAGACACACTAGTGAAT-TCGAGCT 3'

This double-stranded oligonucleotide was ligated to vector pBS-SK+, which had previously been digested with KpnI and SacI, to give the plasmid pEL067.

Figure 16:
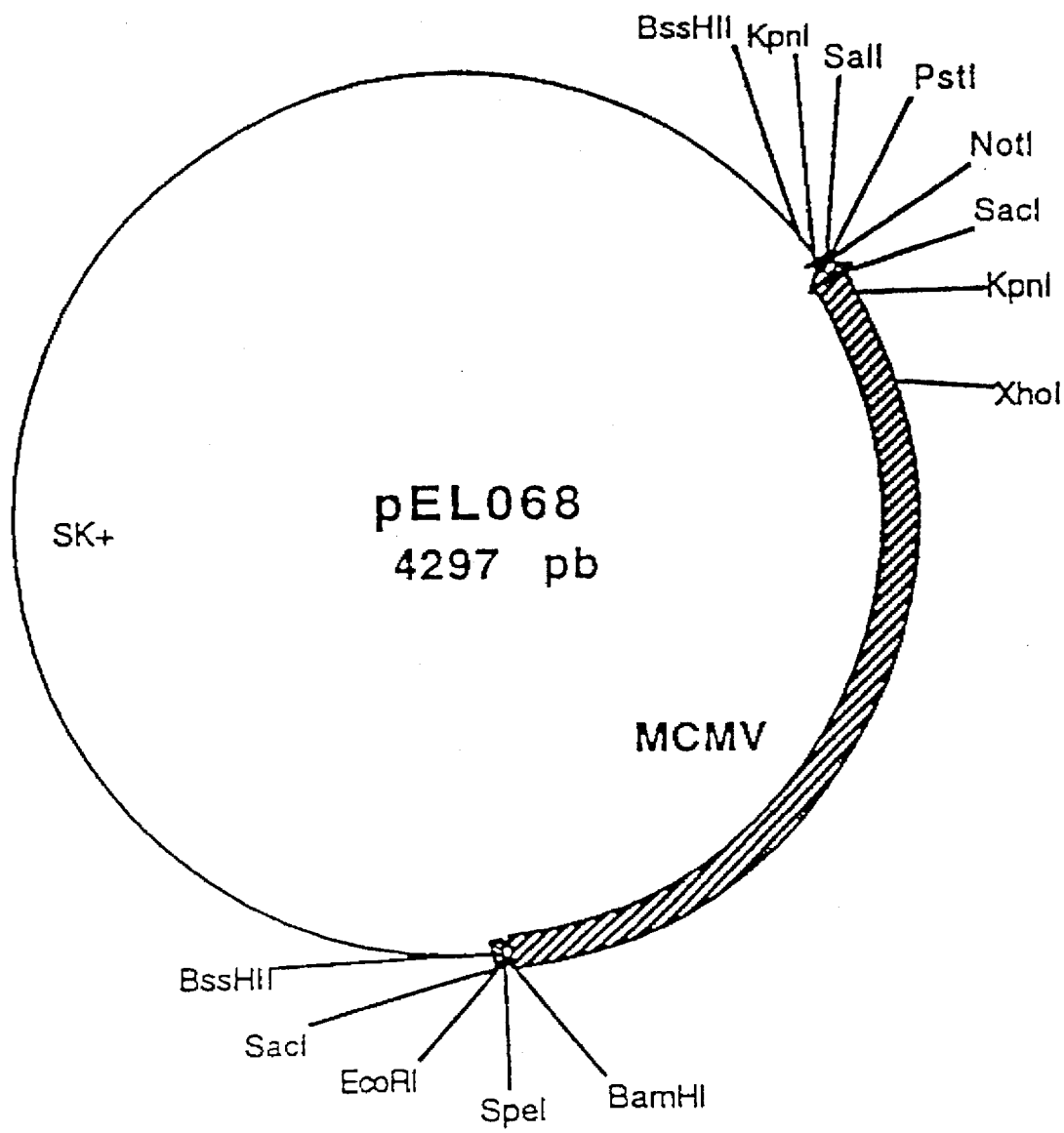
Figure 17:
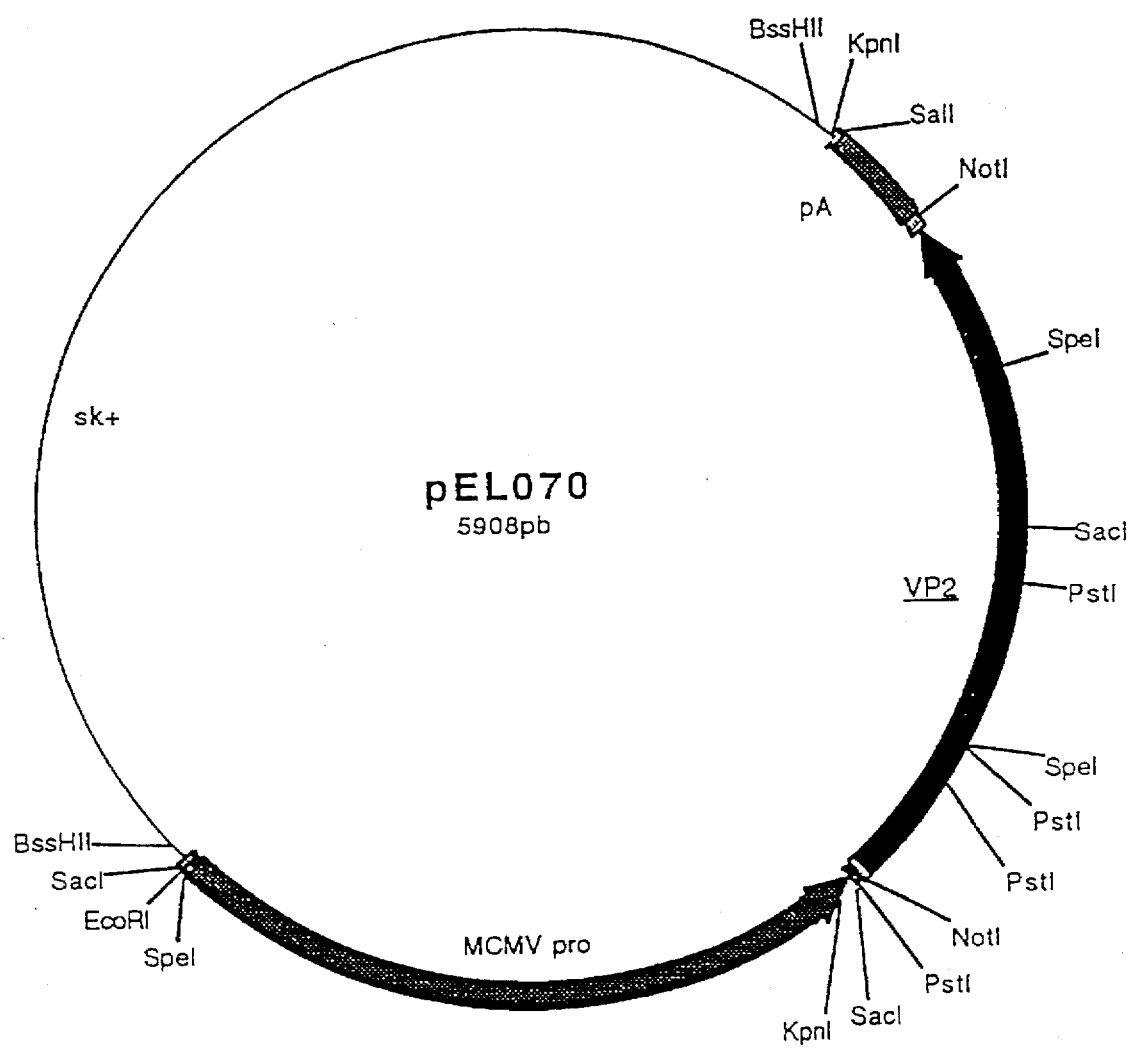
Figure 18:
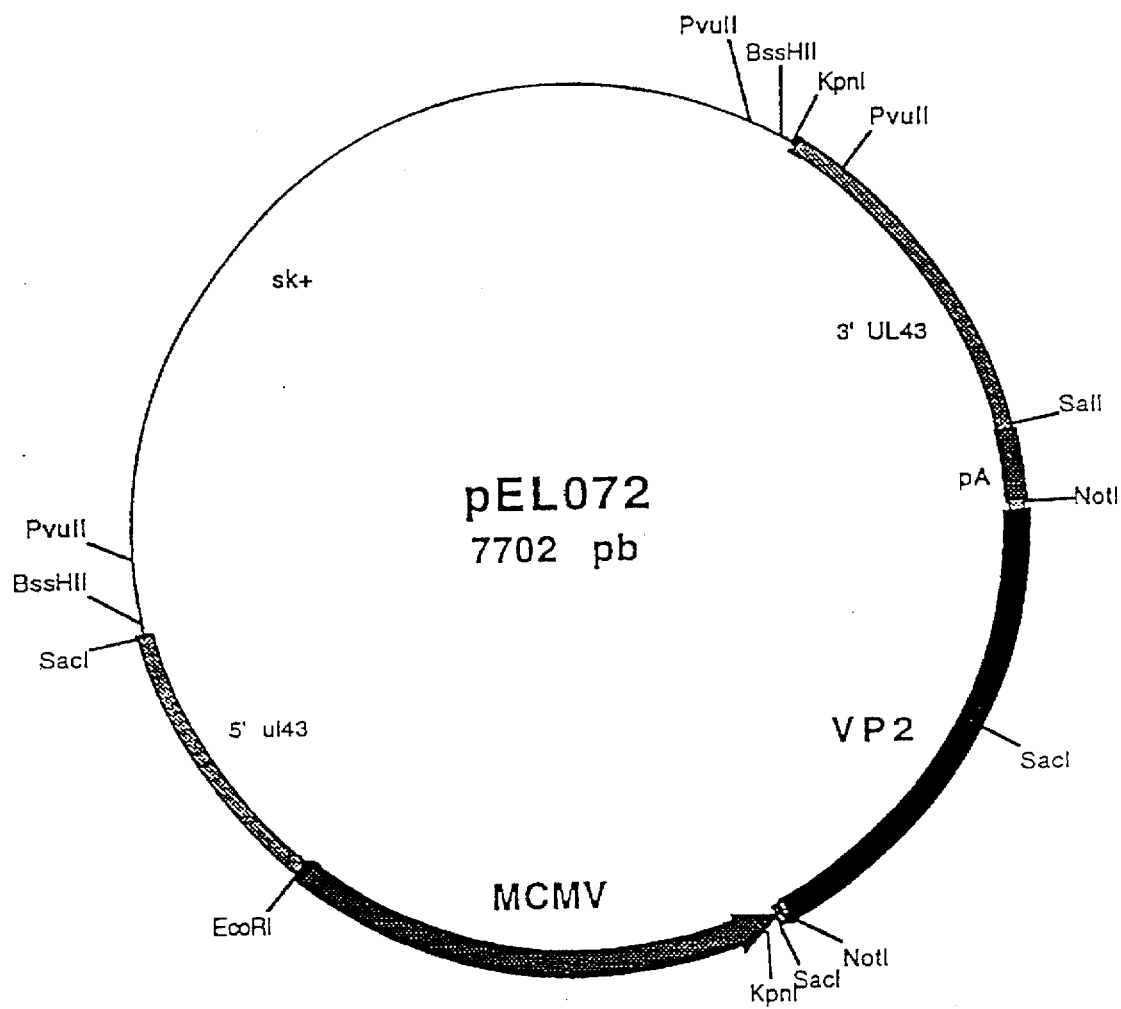

Plasmid pCD009 was digested with PstI and SpeI in order to isolate the PstI/SpeI fragment of 1396 bp. This fragment was ligated to plasmid pEL067, which had previously been digested with PstI and SpeI, to give the plasmid pEL068 of 4297 bp (FIG. 16). Plasmid pEL024 (see Example 5) was digested with HindIII and NotI in order to isolate the HindIII/NotI fragment of 1390 bp (fragment A). Plasmid pEL027 (see Example 6) was digested with HindIII and SalI in order to isolate the HindIII/SalI fragment of 235 bp (fragment B). Fragments A and B were ligated both at once to plasmid pEL068, which had previously been digested with NotI and SalI, to give the plasmid pEL070 of 5908 bp (FIG. 17). Plasmid pEL070 was digested with EcoRI, SalI and XmnI in order to isolate the EcoRI/SalI fragment of 3035 bp. This fragment was ligated to plasmid pMB016 (see Example 6), which had previously been digested with EcoRI and SalI, to give the plasmid pEL072 of 7702 bp (FIG. 18). This plasmid permits the insertion of the MCMV-IE/IBDV VP2 expression cassette into the UL43 locus of the HVT virus.

A cotransfection which was carried out, as described in Example 5, with plasmid pEL072 and genomic DNA of the HVT virus led to the isolation and purification of the vHVT6 recombinant.

EXAMPLE 8

Construction of the Donor Plasmid pCD012 and Isolation of vHVT7

The EcoRI/SalI fragment of 3.9 kbp from the genomic DNA of the MDV virus strain RB1B, which fragment contains the MDV gB gene (sequence published by Ross N. et al. J. Gen. Virol. 1989. 70. 1789–1804), was ligated to the vector pUC13, which had previously been digested with EcoRI and SalI, to give the plasmid pCD007. This plasmid was digested with SacI and XhoI in order to isolate the SacI/XhoI fragment of 2260 bp (central portion of the gB gene=fragment A). A PCR was carried out using the following oligonucleotides:

CD001 (SEQ ID NO. 11) 5' GACTGGTACCGCGGC-CGCATGCACTTTTTAGGCGGAATTG 3'

CD002 (SEQ ID NO. 12) 5' TTCGGGA-CATTTTCGCGG 3' and the pCD007 template in order to produce a PCR fragment of 222 pb. This fragment was digested with KpnI and XbaI in order to isolate a KpnI/XbaI fragment of 190 bp (5' end of the gB gene=fragment B). Another PCR was carried out using the following oligonucleotides:

CD003 (SEQ ID NO. 13) 5' TATATGGCGTTAGTCTCC 3'

Figure 19:
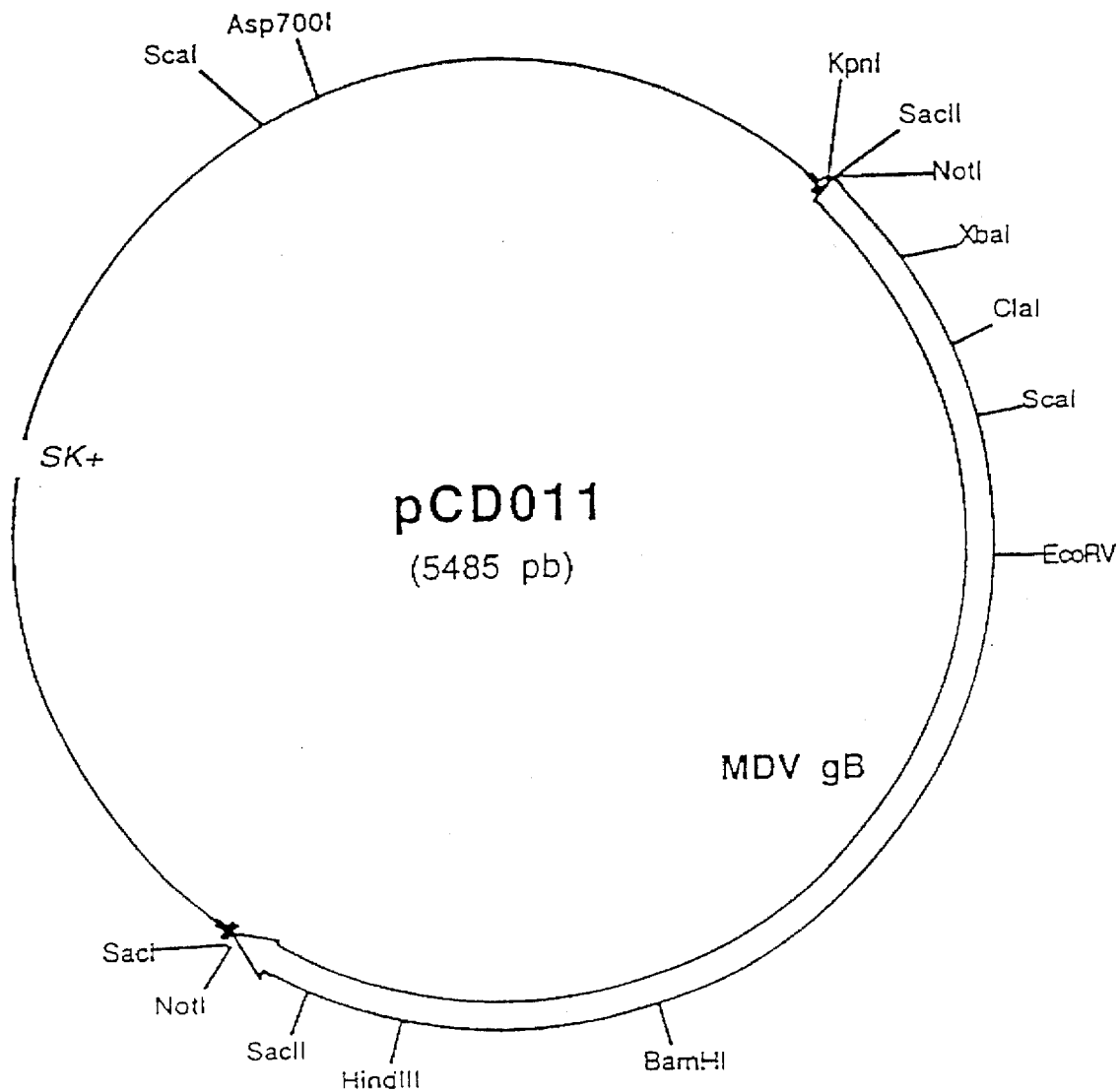
Figure 20:
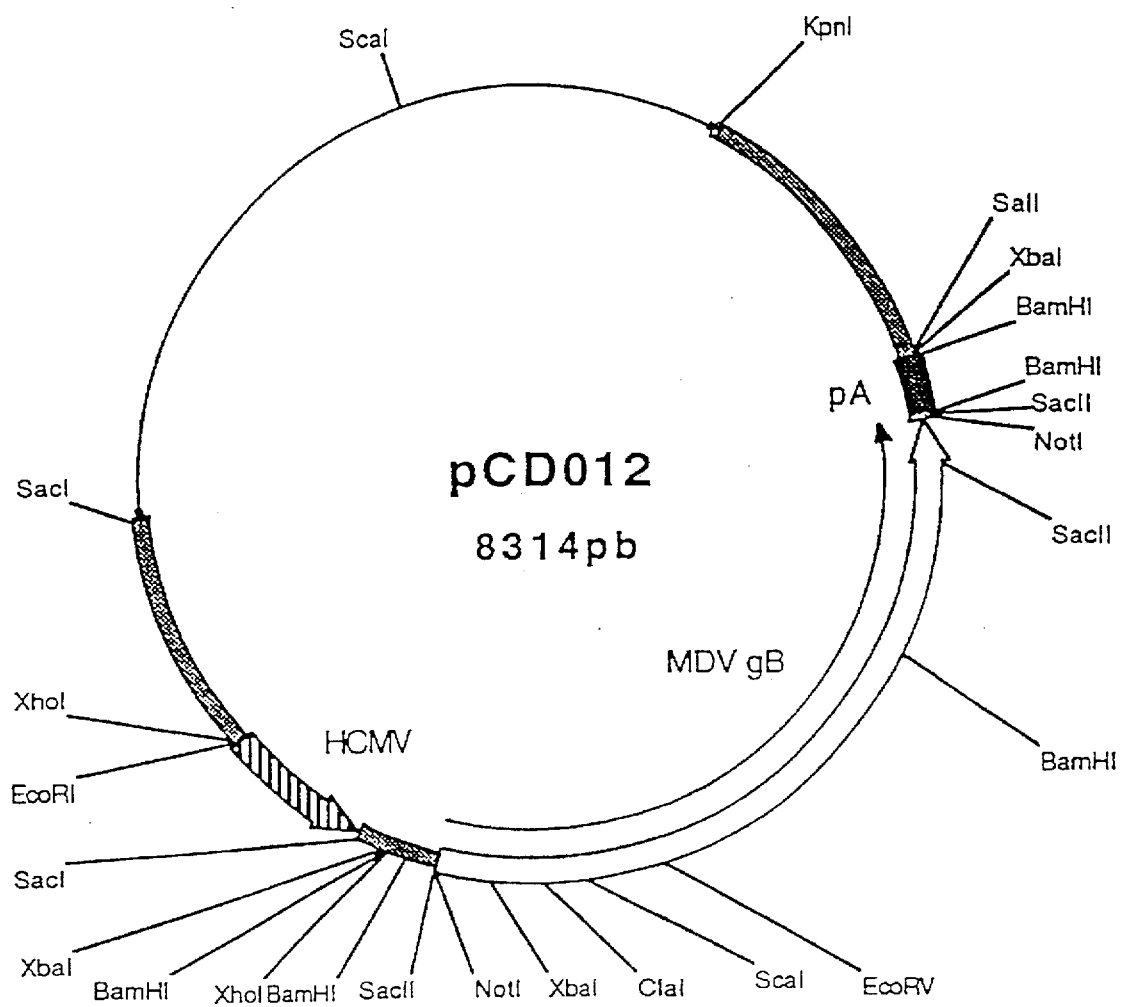

CD004 (SEQ ID NO. 14) 5' TTGCGAGCTCGCGGC-CGCTTATTACACAGCATCATCTTCTG 3' and the pCD007 template in order to produce a PCR fragment of 195 bp. This fragment was digested with SacI and SacII in order to isolate the SacI/SacII fragment of 162 bp (3' end of the gB gene=fragment C). Fragments A, B and C were ligated both at once to vector pBS-SK+, which had previously been digested with KpnI and SacI, to give the plasmid pCD011 of 5485 bp (FIG. 19). Plasmid pCD011 was digested with NotI in order to isolate the NotI/NotI fragment of 2608 bp (entire MDV gB gene=fragment D). Plasmid pEL042 (see Example 6) was digested with NotI and treated with alkaline phosphatase in order to isolate the NotI/NotI fragment of 5706 bp (fragment E). Fragments D and E were then ligated together to give the plasmid pCD012 of 8314 bp (FIG. 20). This plasmid permits insertion of the HCMV-IE/MDV gB cassette into the UL43 locus of the HVT virus.

A cotransfection which was carried out, as described in Example 5, using plasmid pCD012 and genomic DNA of the HVT virus led to the isolation and purification of the vHVT7 recombinant.

EXAMPLE 9

Construction of the Donor Plasmid pEL043 and Isolation of vHVT8

Construction of a complementary DNA library of the genome of Newcastle disease virus (NDV), strain Texas, was carried out as described by Taylor J. et al. (J. Virol. 1990. 64. 1441–1450). A pBR322 clone which contained the end of the fusion (F) gene, the whole of the hemagglutinin neuraminidase (HN) gene and the beginning of the polymerase gene was identified and termed pHN01. The sequence of the NDV EN gene contained in this clone is depicted in FIG. 21 (SEQ ID NO. 15). Plasmid pHN01 was digested with SphI and XbaI in order to isolate the SphI/XbaI fragment of 2520 bp. This fragment was ligated with vector pUC19, which had previously been digested with SphI and XbaI, to give the plasmid pHN02 of 5192 bp. Plasmid pHN02 was digested with ClaI and PstI in order to isolate the ClaI/PstI fragment of 700 bp (fragment A). A PCR was carried out using the following oligonucleotides:

EL071 (SEQ ID NO. 16) 5' CAGACCAAGCTTCT-TAAATCCC 3'

Figure 22:
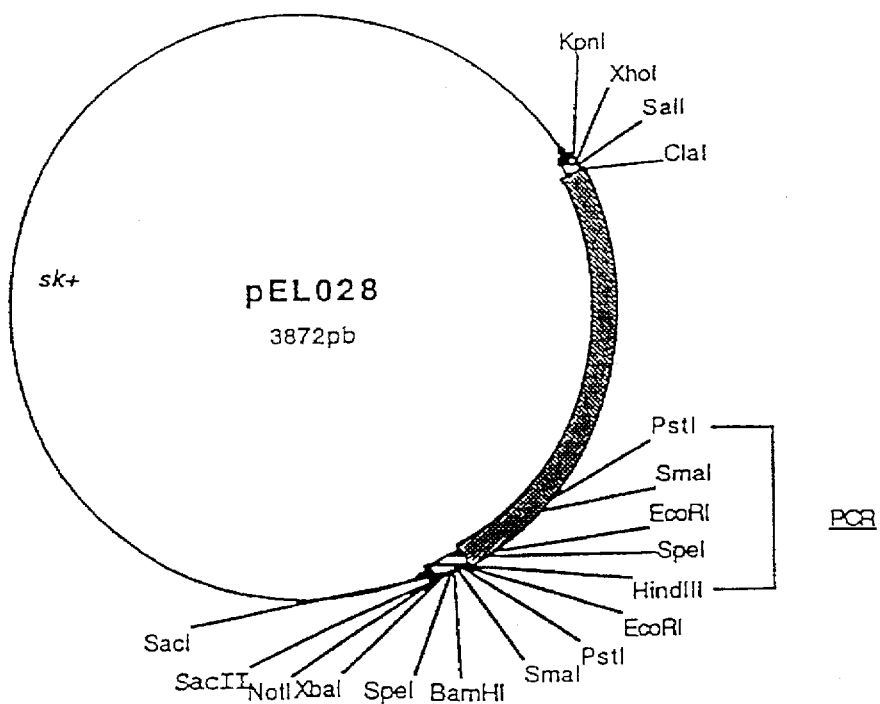

EL073 (SEQ ID NO. 17) 5' GTATTCGGGACAATGC 3' and the pHN02 template in order to produce a PCR fragment of 270 bp. This fragment was digested with HindIII and PstI in order to isolate a HindIII/PstI fragment of 220 bp (fragment B). Fragments A and B were ligated both at once to vector pBS-SK+, which had previously been digested with ClaI and HindIII, to give the plasmid pEL028 of 3872 bp (FIG. 22). Plasmid pHN02 was digested with BsphI and ClaI in order to isolate the BsphI/ClaI fragment of 425 bp (fragment C). A PCR was carried out using the following oligonucleotides:

EL074 (SEQ ID NO. 18) 5' GTGACATCACTAGCGT-CATCC 3'

Figure 23:
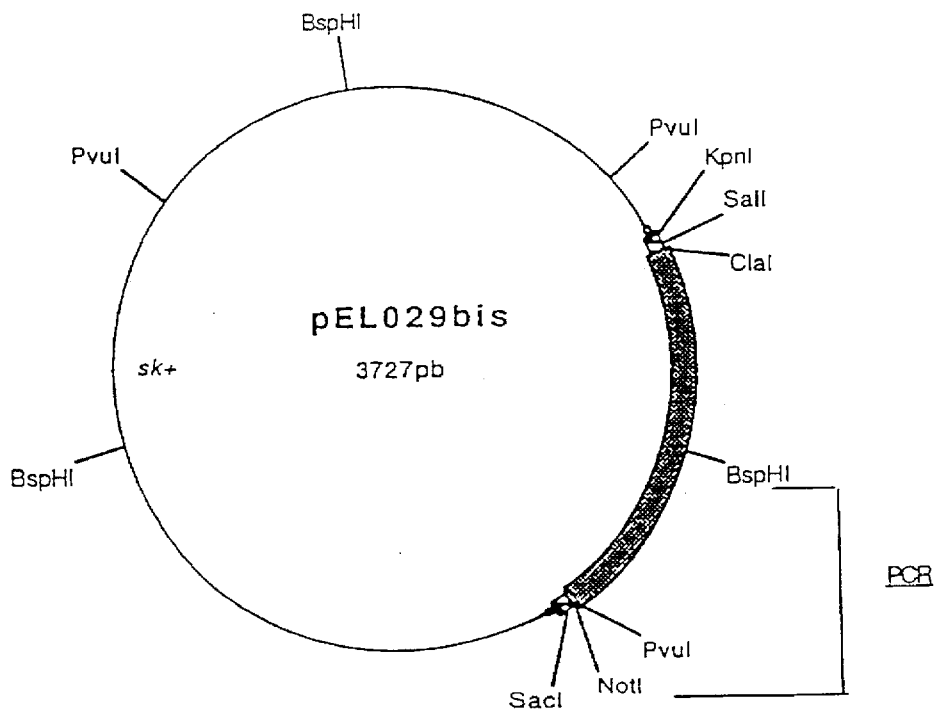
Figure 24:
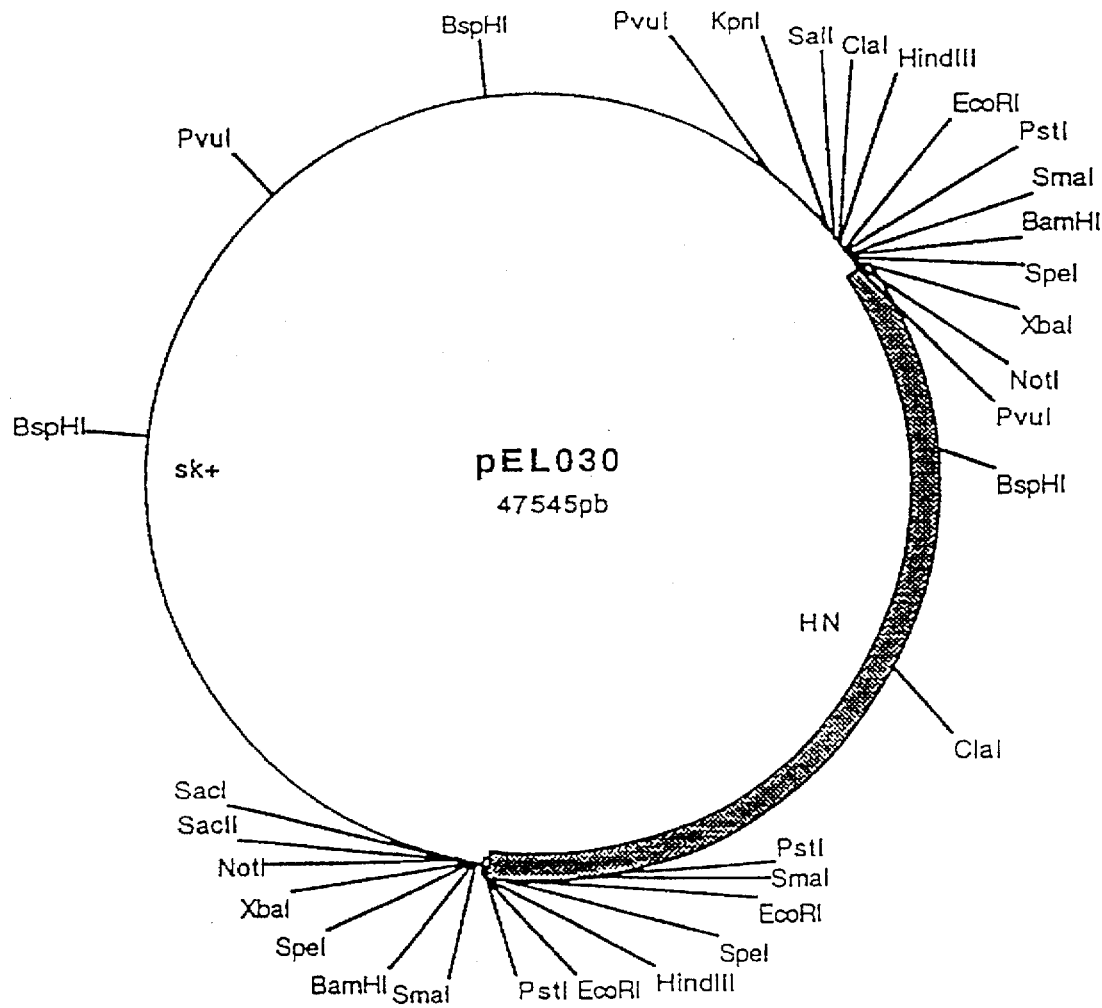
Figure 25:
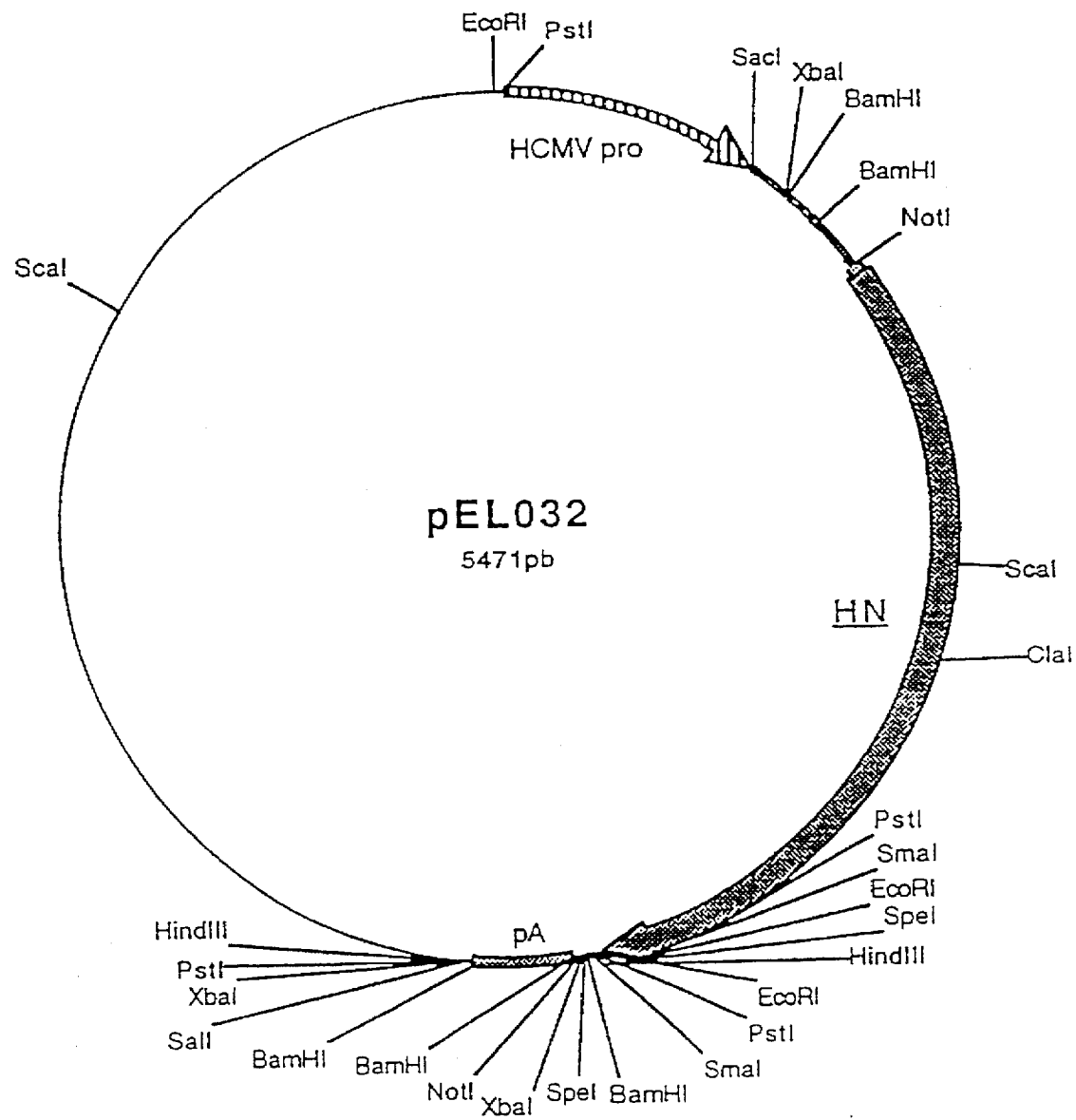
Figure 26:
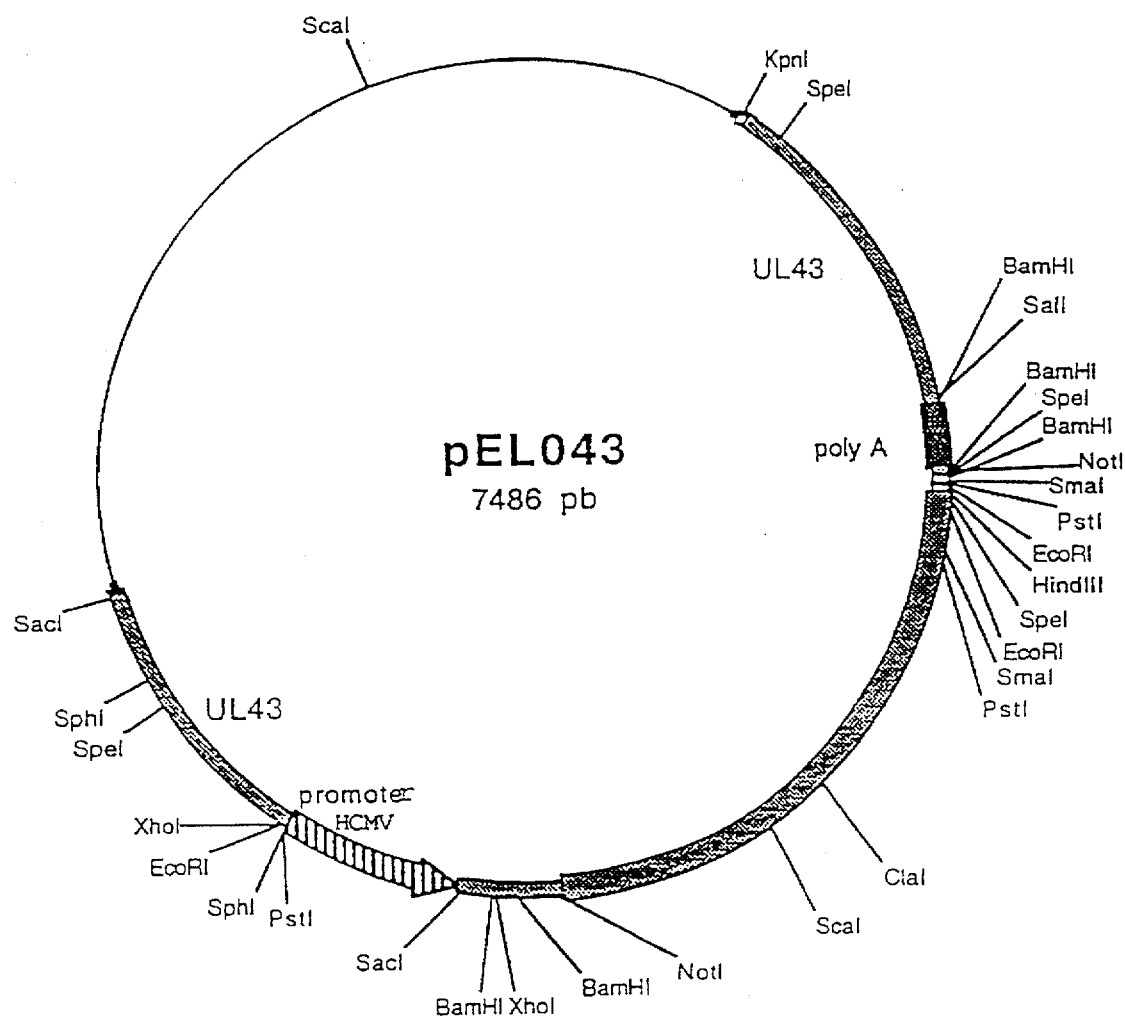

EL075 (SEQ ID NO. 19) 5' CCGCATCATCAGCGGC-CGCGATCGGTCATGGACAGT 3' and the pHN02 template in order to produce a PCR fragment of 465 bp. This fragment was digested with BsphI and NotI in order to isolate the BsphI/NotI fragment of 390 bp (fragment D). Fragments C and D were ligated both at once to vector pBS-SK+, which had previously been digested with ClaI and NotI, to give the plasmid pEL029bis of 3727 bp (FIG. 23). Plasmid pEL028 was digested with ClaI and SacII in order to isolate the ClaI/SacII fragment of 960 bp (fragment E). Plasmid pEL029bis was digested with ClaI and NotI in order to isolate the ClaI/NotI fragment of 820 bp (fragment F). Fragments E and F were ligated both at once to vector pBS-SK+, which had previously been digested with NotI and SacII, to give the plasmid pEL030 of 4745 bp (FIG. 24). Plasmid pEL030 was digested with NotI in order to isolate the NotI/NotI fragment of 1780 bp (entire NDV HN gene). This fragment was ligated, in place of the lacZ gene, to plasmid pCMVβ, which had previously been digested with NotI and treated with alkaline phosphatase, to give the plasmid pEL032 of 5471 bp (FIG. 25). Plasmid pEL032 was digested with EcoRI and ClaI in order to isolate the EcoRI/ClaI fragment of 1636 bp (Fragment G). Plasmid pEL032 was digested with ClaI and SalI in order to isolate the ClaI/SalI fragment of 1182 bp (Fragment H). Fragments G and H were ligated both at once to plasmid pMB016 (see Example 6), which had previously been digested with EcoRI and SalI, to give the plasmid pEL043 of 7486 bp (FIG. 26). This plasmid permits insertion of the HCMV-IE/NDV EN expression cassette into the UL43 locus of the HVT virus.

A cotransfection which was carried out, as described in Example 5, using plasmid pEL043 and genomic DNA of the HVT virus led to the isolation and purification of the vHVT8 recombinant.

EXAMPLE 10

Construction of the Donor Plasmid pEL044 and Isolation of vHVT9

A clone deriving from the complementary DNA library of the genome of Newcastle disease virus (see Example 9), and containing the whole of the fusion (F) gene, was termed pNDV81. This plasmid has been described previously and the sequence of the NDV F gene which is present in this clone has been published (Taylor J. et al. J. Virol. 1990. 64. 1441–1450). Plasmid pNDV81 was digested with NarI and PstI in order to isolate the NarI/PstI fragment of 1870 bp (fragment A). A PCR was carried out using the following oligonucleotides:

EL076 (SEQ ID NO. 20) 5' TGACCCTGTCTGGGATGA 3'

Figure 27:
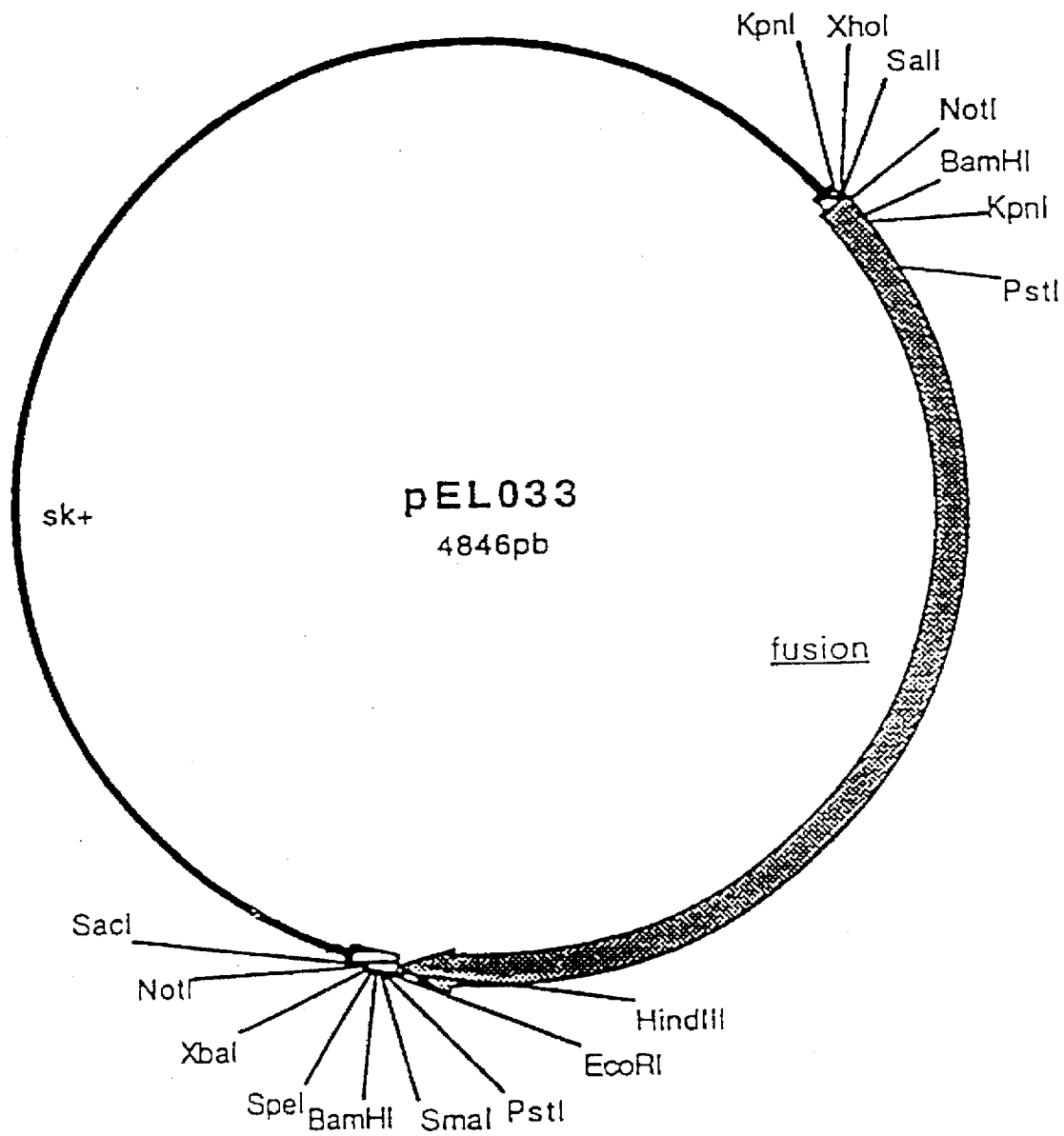
Figure 28:
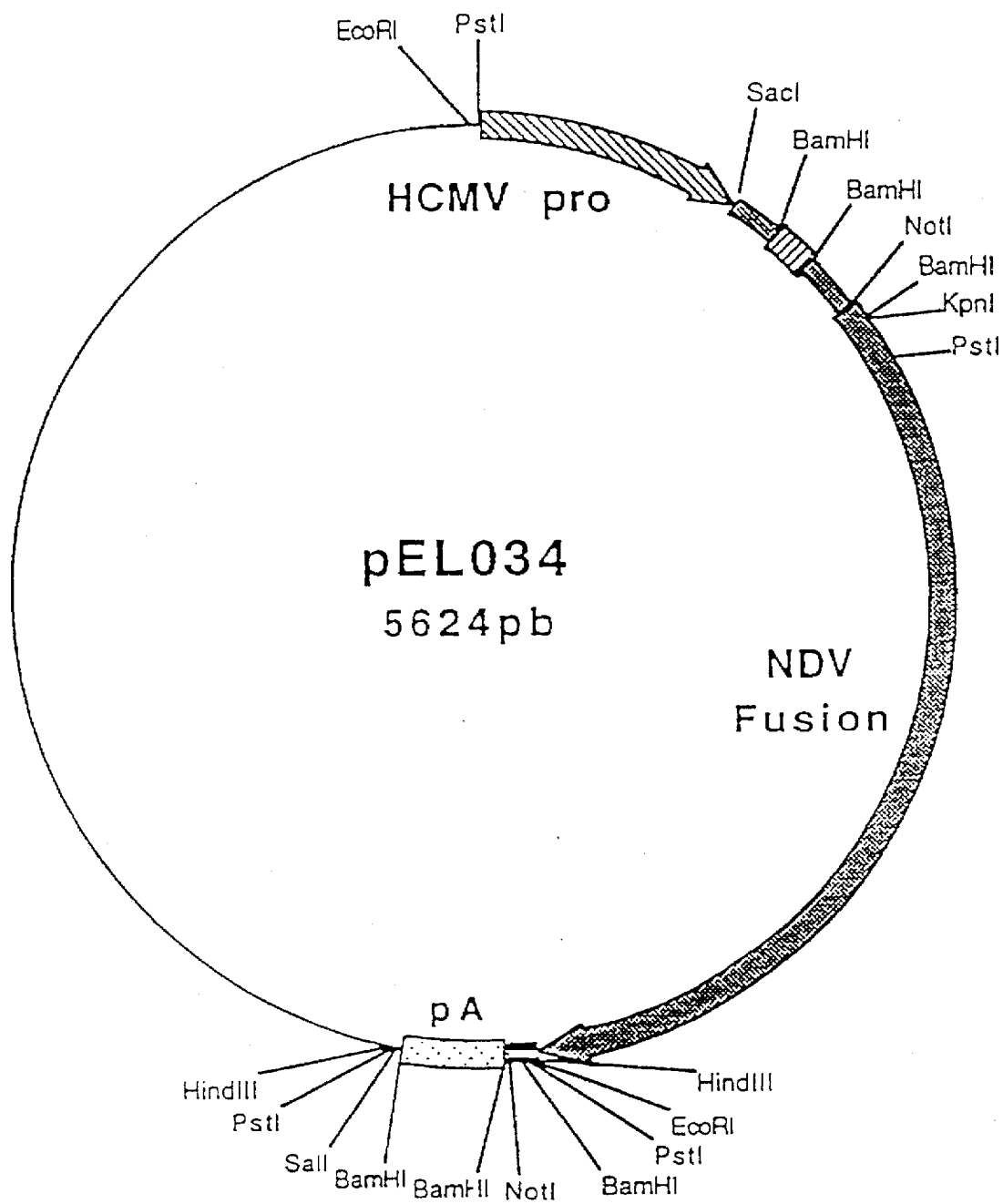
Figure 29:
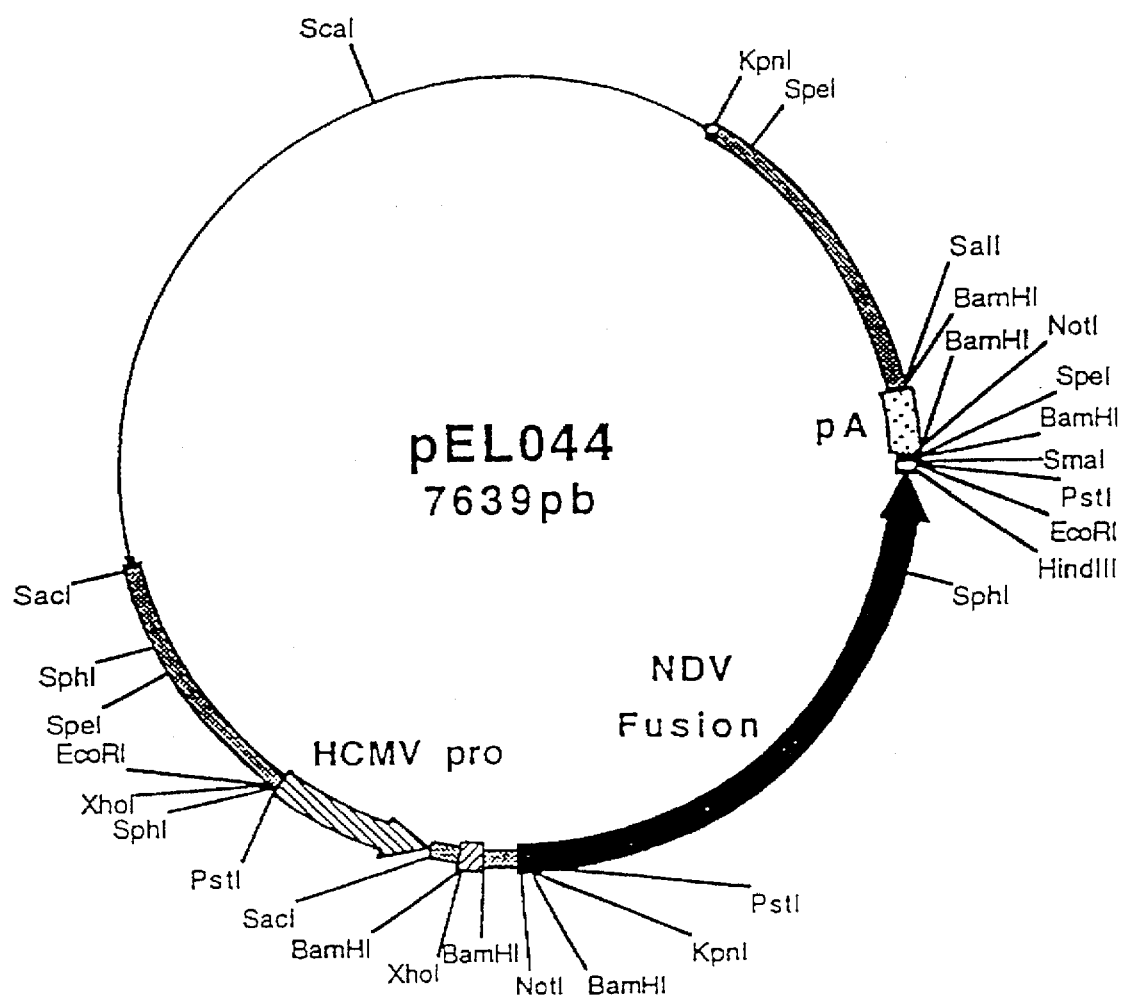

EL077 (SEQ ID NO. 21) 5' GGATCCCGGTCGACA-CATTGCGGCCGCAAGATGGGC 3' and the pNDV81 template in order to produce a fragment of 160 pb. This fragment was digested with PstI and SalI in order to isolate the PstI/SalI fragment of 130 bp (fragment B). Fragments A and B were ligated both at once to vector pBS-SK+, which had previously been digested with ClaI and SalI, to give the plasmid pEL033 of 4846 bp (FIG. 27). Plasmid pEL033 was digested with NotI in order to isolate the NotI/NotI fragment of 1935 bp (entire F gene). This fragment was ligated to plasmid pCMVβ, which had previously been digested with NotI and treated with alkaline phosphatase, to give the plasmid pEL034 of 5624 bp (the NDV F gene has replaced the lacZ gene) (FIG. 28). Plasmid pEL034 was digested with EcoRI and KpnI in order to isolate the EcoRI/KpnI fragment of 866 pb (Fragment C). Plasmid pEL034 was digested with KpnI and SalI in order to isolate the KpnI/SalI fragment of 2114 bp (Fragment D). Fragments C and D were ligated both at once to plasmid pMB016 (see Example 6), which had previously been digested with EcoRI and SalI, to give the plasmid pEL044 of 7639 bp (FIG. 29). This plasmid permits insertion of the HCMV-IE/NDV F expression cassette into the UL43 locus of the HVT virus. A cotransfection which was carried out, as described in Example 5, using plasmid pEL044 and genomic DNA of the HVT virus led to the isolation and purification of the vHVT9 recombinant.

EXAMPLE 11

Construction of the Donor Plasmid pEL082 and Isolation of vHVT10

The sequences situated upstream of the MDV 1.8 kbp RNA gene are described in Bradley G, et al. (J. Virol. 1989. 63. 2534–2542) (FIG. 30 and SEQ ID NO. 22). A PCR amplification was carried out on DNA extracted from lymphocytes which were harvested from chicks infected with the MDV RB1B strain (see Example 1) using the following oligonucleotides:

MB047 (SEQ ID NO. 23) 5' GGTCTACTAGTATTG-GACTCTGGTGCGAACGC 3'

MB048 (SEQ ID NO. 24) 5'GTCCAGAATTCGCGAA-GAGAGAAGGAACCTC 3'

Figure 31:
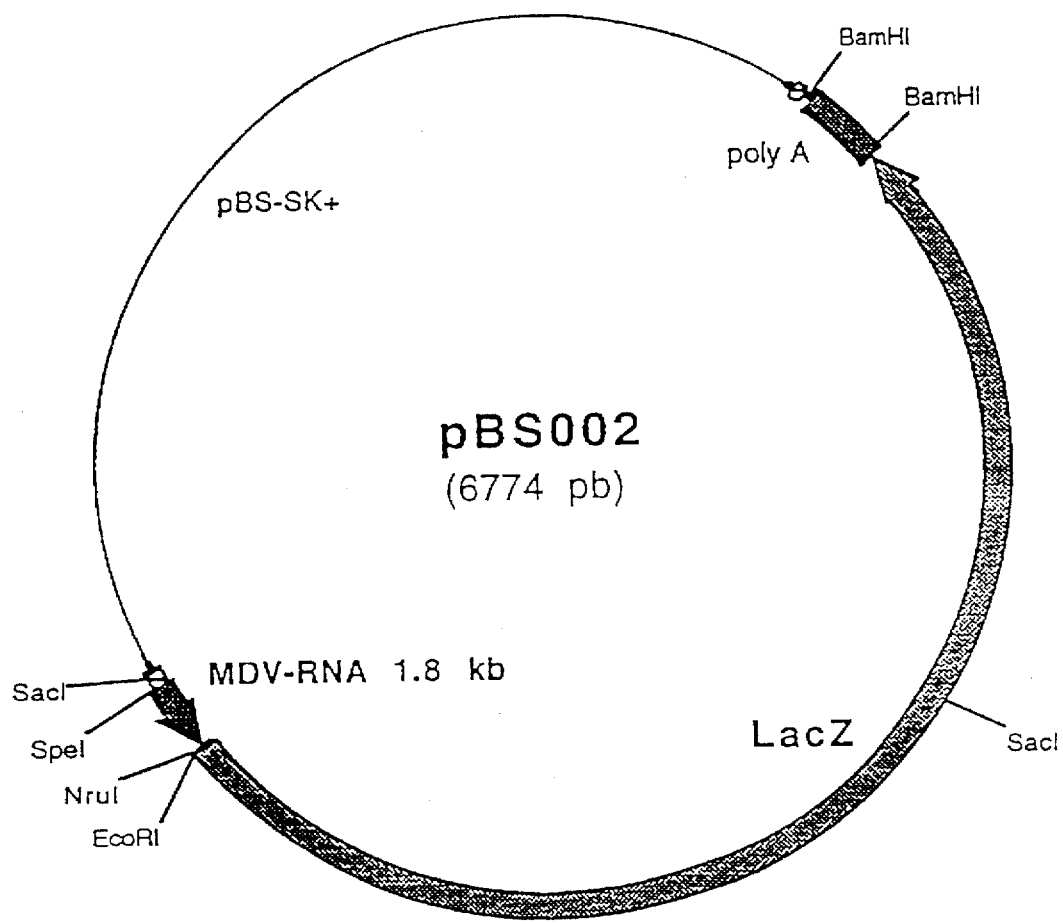

The PCR fragment of 163 bp thus obtained was digested with EcoRI and SpeI and then ligated to plasmid pCD002 (see Example 7), which had previously been digested with EcoRI and SpeI, to give the plasmid pBS002 of 6774 bp (FIG. 31). Plasmid pBS002 contains the promoter of the MDV 1.8 kb RNA gene clone upstream of the lacZ gene. A PCR was carried out using the oligonucleotides:

MB047 (SEQ ID NO. 23) and

Figure 32:
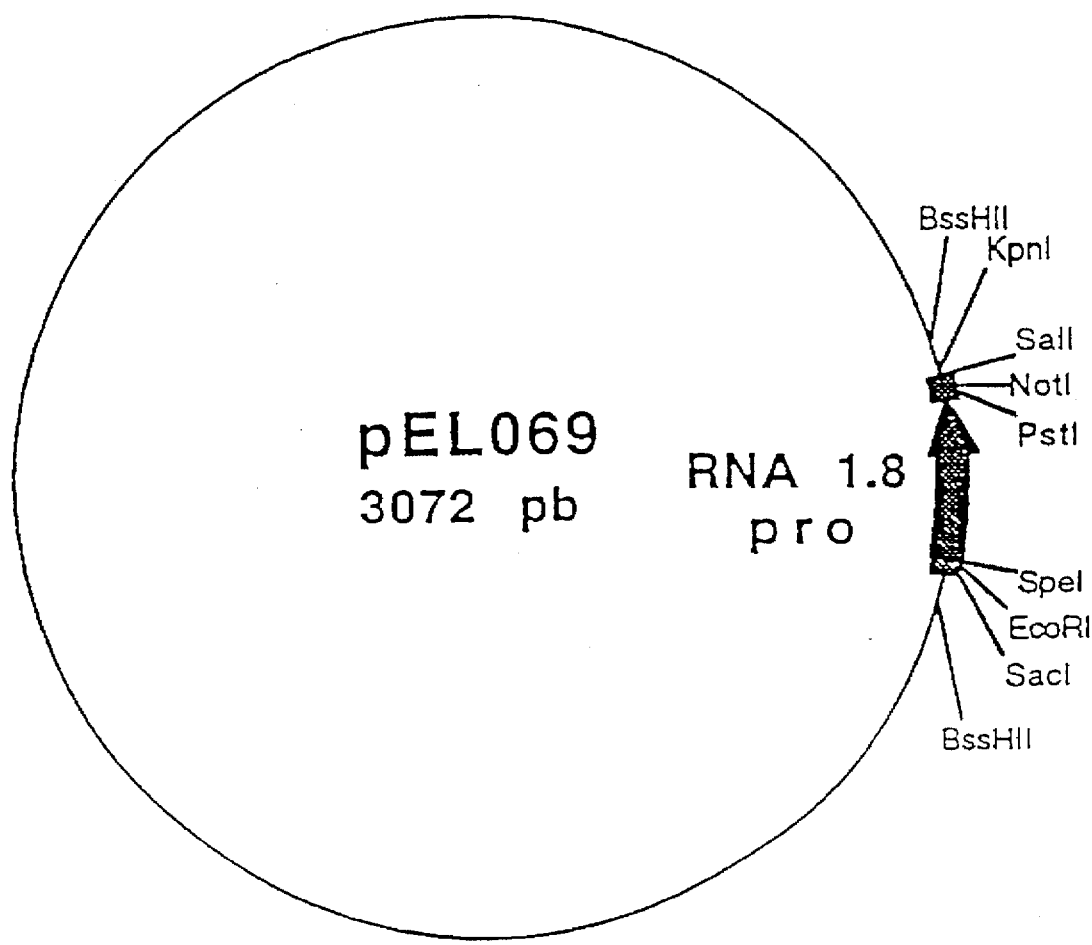
Figure 33:
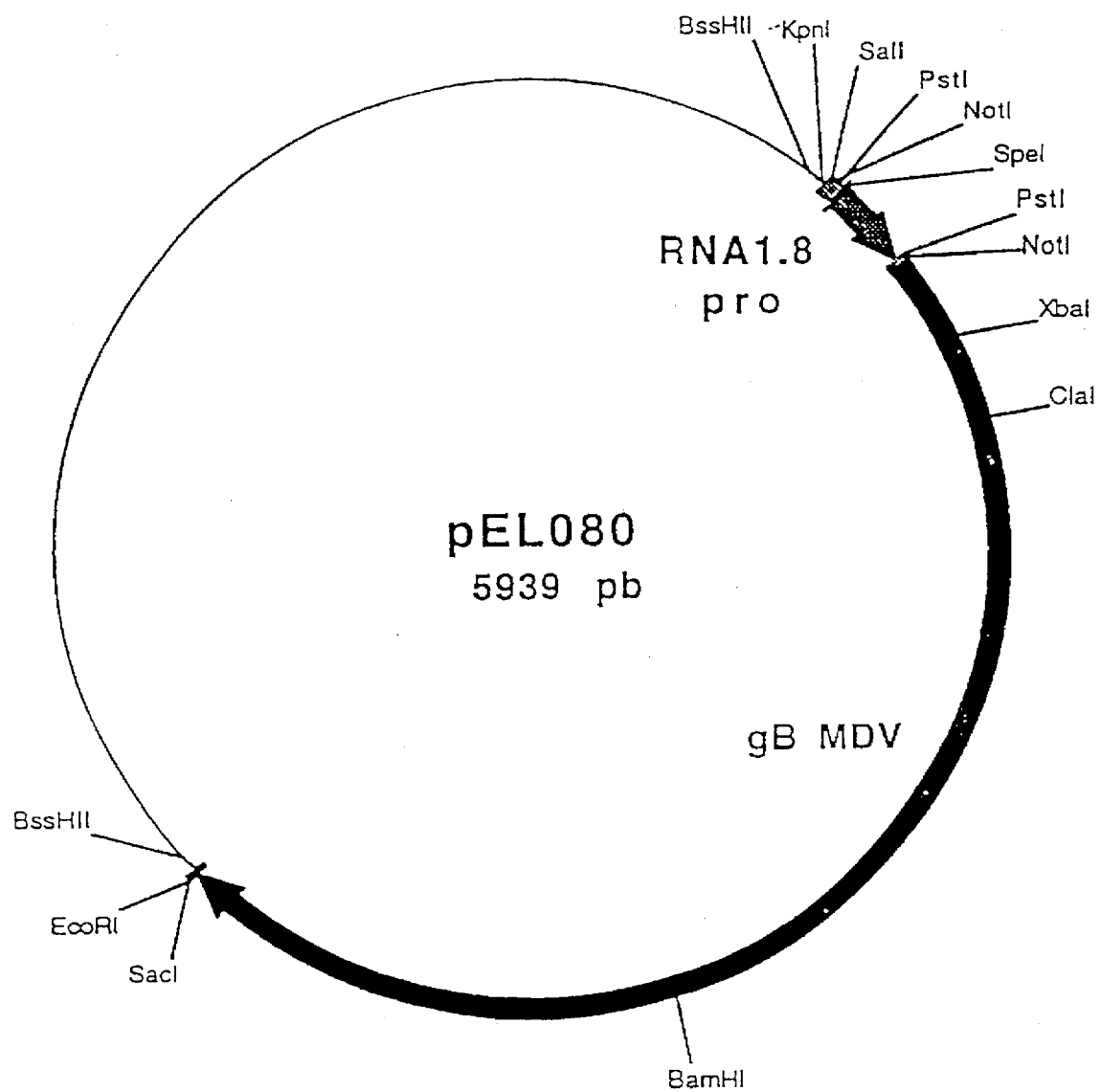
Figure 34:
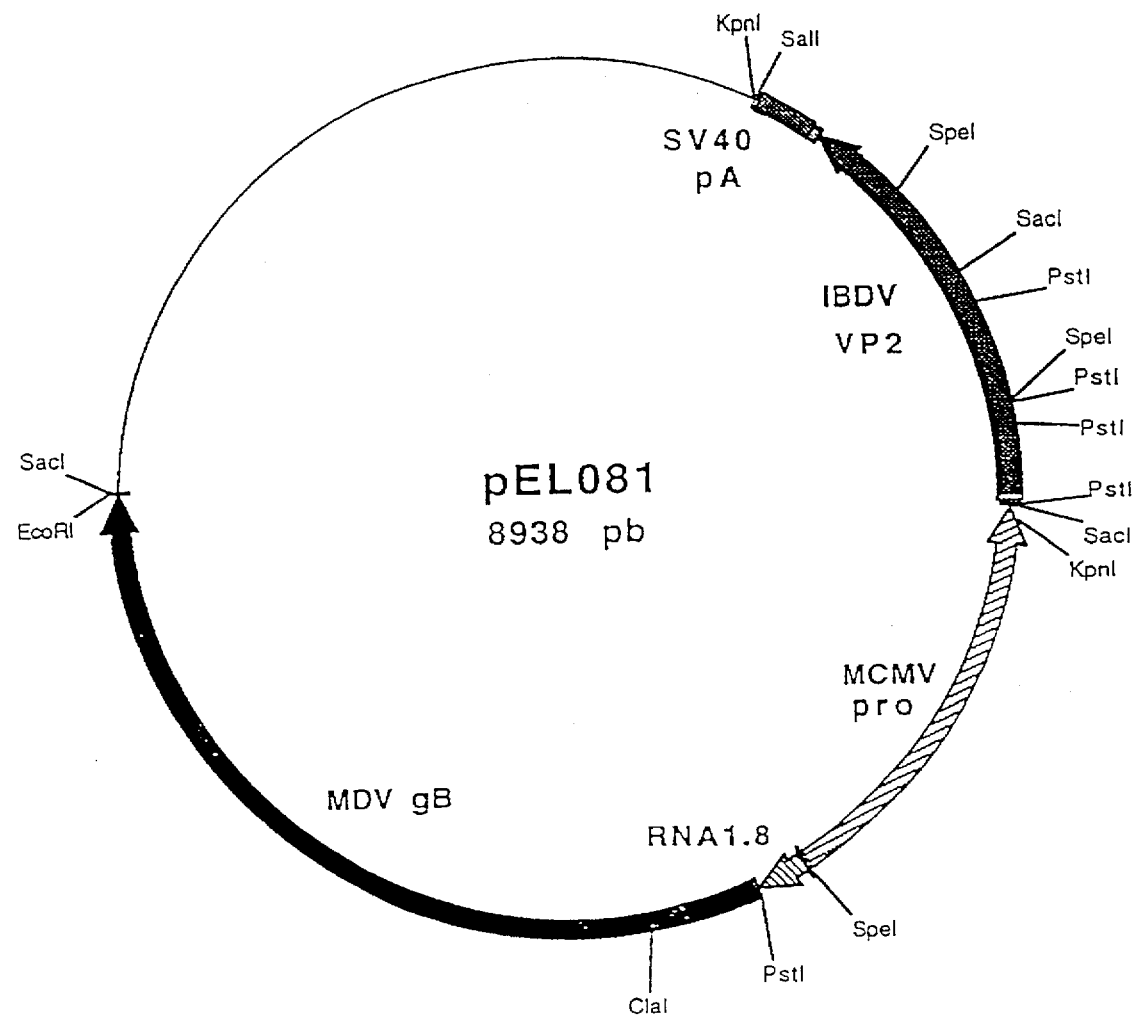
Figure 35:
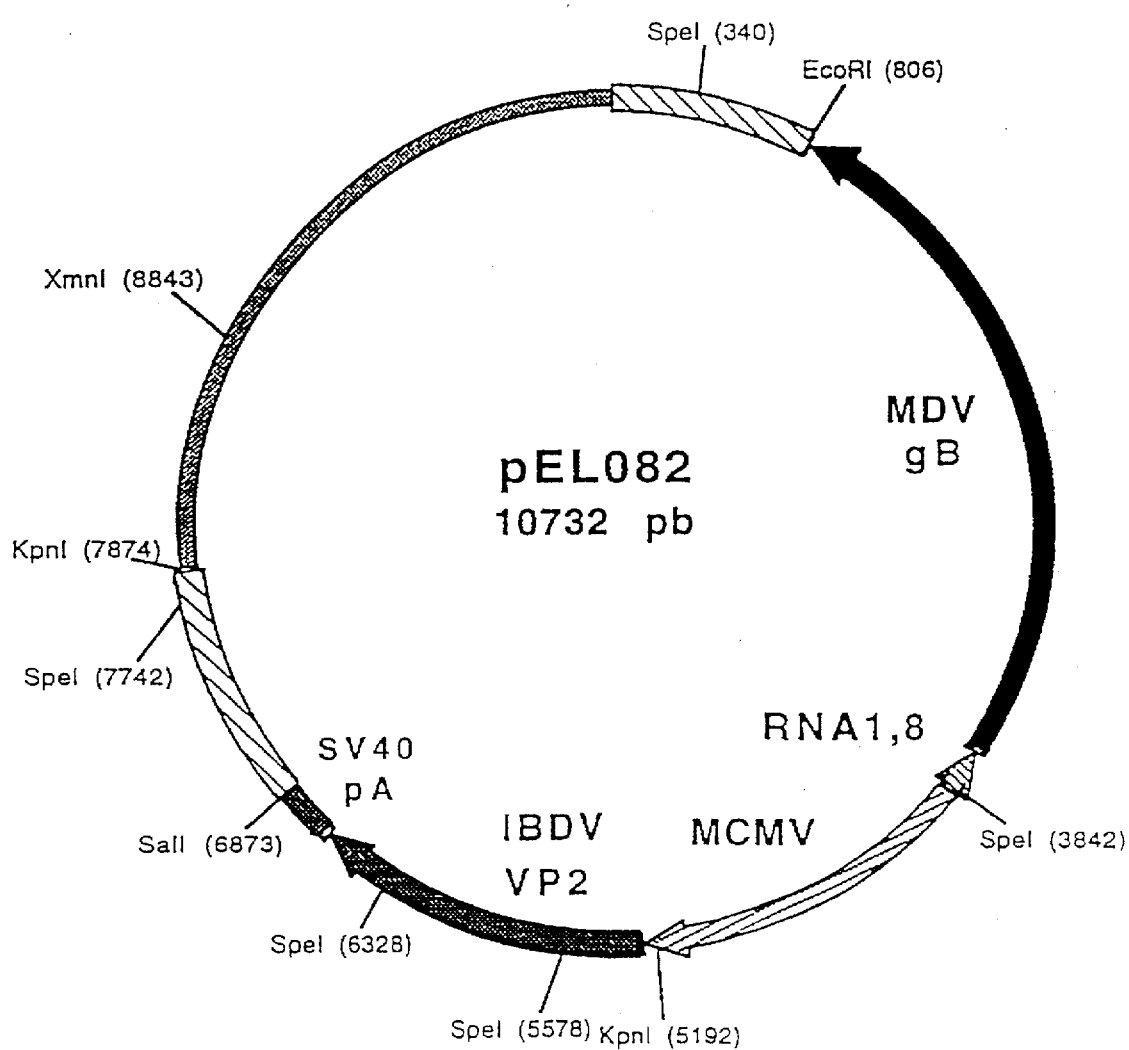

MB072 (SEQ ID NO. 25) 5 ' GTGTCCTGCAGTCGC-GAAGAGAGAAGGAACCTC 3' and the pBS002 template. The PCR fragment thus obtained was digested with PstI and SpeI in order to isolate a PstI/SpeI fragment of 200 bp. This fragment was ligated to plasmid pEL067 (see Example 7), which had previously been digested with PstI and SpeI, to give the plasmid pEL069 (FIG. 32). Plasmid pCD007 (see Example 8) was digested with EcoRI and XbaI in order to isolate the EcoRI/XbaI fragment of 2670 bp (fragment A). Plasmid pCD011 (see Example 8) was digested with NotI and XbaI in order to isolate the NotI/XbaI fragment of 180 bp (fragment B). Plasmid pEL069 was digested with NotI and SpeI in order to isolate the NotI/SpeI fragment of 180 bp (fragment C). Fragments A, B and C were ligated both at once to plasmid pEL067 (see Example 7), which had previously been digested with EcoRI and SpeI, to give the plasmid pEL080 of 5939 bp (FIG. 33). Plasmid pEL070 (see Example 7) was digested with KpnI and SpeI in order to isolate the KpnI/SpeI fragment of 1345 bp (fragment D). Plasmid pEL070 was also digested with KpnI and SalI in order to isolate the KpnI/SalI fragment of 1658 bp (fragment E). Fragments D and E were ligated both at once to plasmid pEL080, which had previously been digested with SalI and SpeI, to give the plasmid pEL081 of 8938 bp (FIG. 34). Plasmid pEL081 was digested with EcoRI and SalI in order to isolate the EcoRI/SalI fragment of 6066 bp. This fragment was ligated to plasmid pMB016 (see Example 6), which had previously been digested with EcoRI and SalI, finally to give the plasmid pEL082 of 10732 bp (FIG. 35). This plasmid makes it possible to insert the double VP2/MCMV-IE//1.8 kbp RNA/MDV gB expression cassette into the UL43 locus of the HVT virus.

A cotransfection which was carried out, as described in Example 5, using plasmid pEL082 and the genomic DNA of the HVT virus led to the isolation and purification of the vHVT10 recombinant.

EXAMPLE 12

Construction of the Donor Plasmid pEL096 and Isolation of vHVT22

Figure 36:
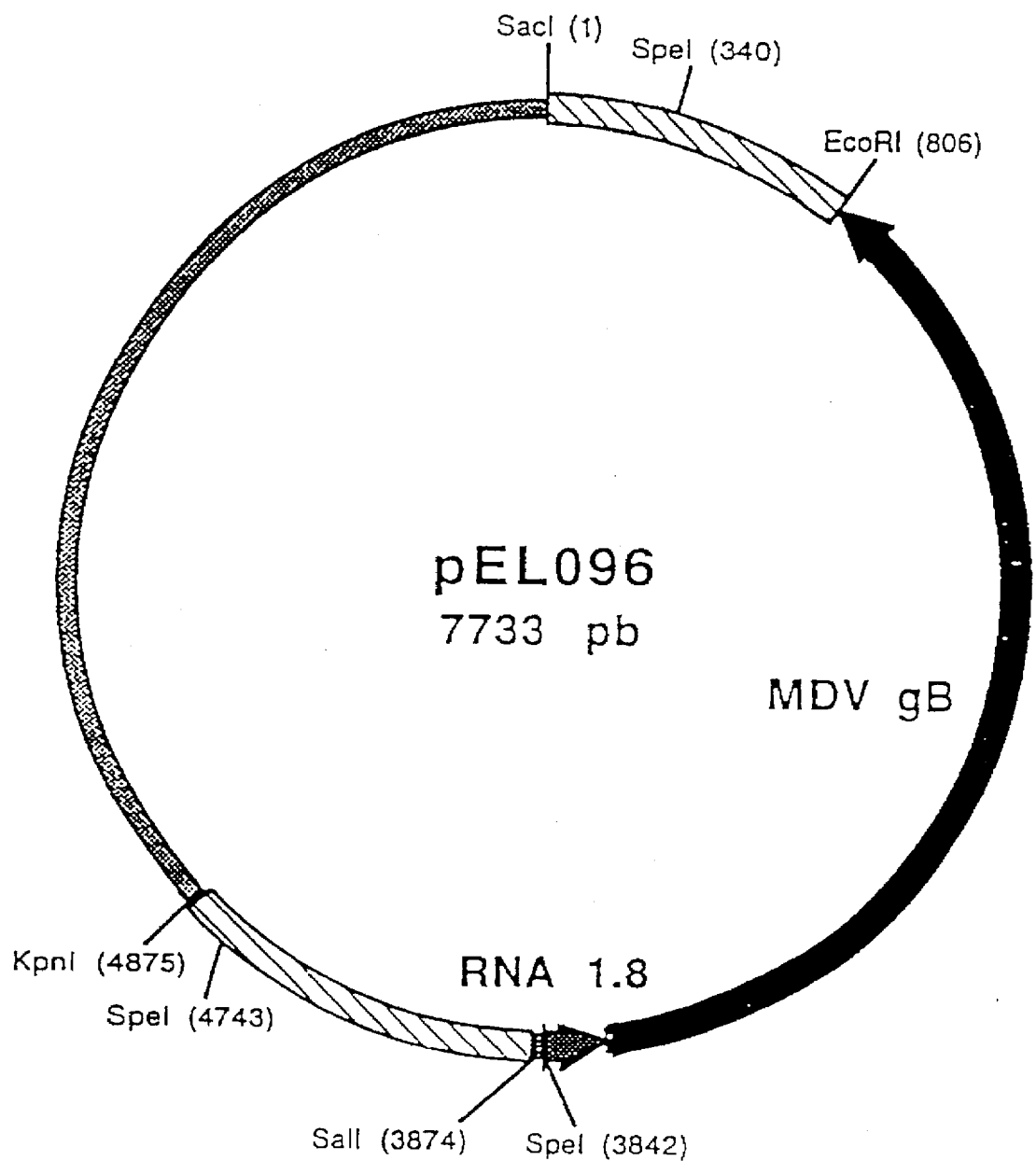

Plasmid pEL080 (see Example 11) was digested with EcoRI and SalI in order to isolate the EcoRI/SalI fragment of 3040 bp (1.8 kbp RNA/MDV gB cassette). This fragment was ligated to plasmid pMB016 (see Example 6), which had previously been digested with EcoRI and SalI, to give the plasmid pEL096 of 7733 bp (FIG. 36). This plasmid makes it possible to insert the 1.8 kbp RNA/MDV gB expression cassette into the UL43 locus of the HVT virus.

A cotransfection which was carried out, as described in Example 5, using plasmid pEL096 and the genomic DNA of the HVT virus led to the isolation and purification of the vHVT22 recombinant.

EXAMPLE 13

Construction of Donor Plasmids for Inserting IBV M and S Expression Cassettes into the UL43 Locus of the HVT Virus Using the same strategy as that which is described above for inserting expression cassettes (genes placed under the control of the HCMV-IE or MCMV-IE promoters or the MCMV-IE//1.8 kbp RNA double promoter) into the UL43 locus, it is possible to produce recombinant HVT viruses which express the membrane (M) or spike (S) proteins of avian infectious bronchitis virus (IBV) at an elevated level. A construct is preferably produced in which the IBV S gene is dependent on the HCMV-IE promoter or the MCMV-IE promoter, or else a construct in which the IBV M and IBV S genes are inserted together with the MCMV-IE/1.8 kbp RNA double promoter in the UL43 locus, the M gene being under the control of the 1.8 kbp RNA promoter and the S gene being under the control of the MCMV-IE promoter. In this configuration, the 1.8 kbp RNA promoter is activated by the enhancer region of the MCMV-IE promoter.

EXAMPLE 14

Study of the Viremia Induced by the vHVT1, vHVT2 and vHVT4 Recombinants (In Vivo Replication)

The viremia which was induced by inoculating the different recombinant viruses was studied in order to evaluate the degree to which the genomic modifications following upon insertion of the expression cassettes brought about an attenuation of replication in vivo.

The recombinant viruses to be tested were diluted in Marek vaccine diluent in order to obtain different inoculums for each recombinant. The viral suspensions produced in this way were administered by the intramuscular route to several groups of 1-day-old SPF chicks at the rate of 0.2 ml per chick. Control chicks were given 0.2 ml of Marek vaccine diluent in the same manner.

The blood of chicks taken at random from each inoculated group was then withdrawn individually by taking terminal blood samples into anticoagulant (heparin solution of 100 IU/ml) at 7, 11 and 21 days after inoculation. In order to isolate the leucocytes, each withdrawn blood sample was transferred into a tube and centrifuged for 15 minutes at 30 g and at ambient temperature. The plasma and the band of leucocytes (buffy coat) were removed and diluted in sterile PBS in order to obtain a final volume of 10 ml. After centrifuging at 150 g for 15 minutes at ambient temperature, the cell pellet was taken up in 2 ml of 199 medium containing 2% FCS. The viable leucocytes were then counted and their concentration calculated. Determination of the number of infected lymphocytes is carried out as follows: $10^6$ or $2.10^6$ viable leucocytes, diluted in 2 ml of 199 medium, are added to a 60 mm-diameter Petri dish which was seeded 24 hours previously with from 1.5 to $2.10^6$ CEC II/dish. After 2 hours of culture, the medium in each dish is removed and replaced with 5 ml of hypotonic 199 medium containing 1% FCS. The dishes are then incubated at 37° C. for 4 days in a 5% $CO_2$ incubator. The plaques which have appeared on the lawn are not read until the end of the 4th day after commencing the coculture.

RESULTS

The viremia induced by the recombinant viruses vHVT1 (RR2 locus), vHVT2 (gI locus) and vHVT4 (UL43 locus) was studied and compared with the viremia induced by the parental HVT virus strain FC126.

The results are summarized in Table 1 (individual values obtained for 4–5 chicks per group and per day of withdrawal). The viremia observed for each of the recombinants is indicative of the in vivo replication.

TABLE 1

Viremias induced by the HVT recombinants

| Vaccine | Dose (PFU) | Number of viremic chicks/ number of chicks in the group | | |
|---|---|---|---|---|
| | | Day 7 | Day 11 | Day 21 |
| vHVT1 | $10^4$ | 5/5 | 1/5 | 0/5 |
| vHVT1 | $10^3$ | 2/5 | 1/5 | 0/5 |
| vHVT2 | $10^4$ | 0/5 | 0/5 | 0/5 |
| vHVT2 | $10^3$ | 0/5 | 0/5 | 0/5 |
| vHVT4 | $10^3$ | 2/4 | 4/4 | 3/4 |
| HVT FC126 | $10^4$ | 4/4 | 4/4 | 4/4 |
| HVT FC126 | $10^3$ | 4/4 | 4/4 | 4/4 |
| Controls | — | 0/2 | 0/2 | 0/2 |

CONCLUSIONS

Insertion of an expression cassette into the RR2 locus results in a certain attenuation of in vivo replication. Insertion into the gI locus causes a considerable decrease in in vivo replication, since no viremia can be measured even after inoculating $10^4$ PFU of recombinant virus/chick. By contrast, insertion into the UL43 locus only brings about weak attenuation of the viremia, making this a good locus for introducing expression cassettes into the genome of the HVT virus.

EXAMPLE 15

Study of Protection against Gumboro

The protection against Gumboro disease which was induced by different recombinant HVT viruses was studied in a chick vaccination/challenge model and compared with that induced by a conventional inactivated vaccine (Gumboriffa, Rhône Mérieux).

Groups of one-day-old SPF chicks were vaccinated by the intramuscular route with the recombinant viruses or with the inactivated vaccine. 21 days after vaccination, all the chicks were challenged by the ocular route with a dose of $10^{2.5}$ $IOD_{50}$ of IBDV virus strain Faragher. 4 days (trial 1) or 10 days (trial 2) after the challenge, the surviving animals are sacrificed, weighed and then dissected in order to recover the bursa of Fabricius. The bursas are weighed and examined for the presence of lesions caused by Gumboro disease. The final protection is evaluated in accordance with two criteria: 1) the presence or absence of lesions in the bursa. 2) the bursa weight/body weight ratio expressed in %. A non-vaccinated and non-challenged control group, and also a non-vaccinated and challenged control group, enable reference values to be obtained for "protected" chicks and non-protected chicks, respectively. The protected chicks must have, in the absence of macroscopic lesions in the bursa, a bursa weight/body weight ratio of >0.4%. Chicks which have a bursa weight/body weight ratio of ≦0.4% are not protected.

The protection results are presented in Tables 2 and 3 below.

TABLE 2

Trial 1: Protection results obtained with vHVT1

| Chick group | Number of chicks | Vaccine | Dose (PFU) | No. of dead/ total No. | Positive chicks/ total | Protection % |
|---|---|---|---|---|---|---|
| 1 | 12 | vHVT1 | $10^5$ | 0/12 | 6/12 | 50% |
| 2 | 12 | vHVT1 | $10^4$ | 2/12 | 8/12 | 33% |
| 3 | 12 | vHVT1 | $10^3$ | 1/12 | 12/12 | 0% |
| 4 | 12 | vHVT1 | $10^2$ | 4/12 | 12/12 | 0% |
| 5 | 12 | challenged controls | — | 7/12 | 12/12 | 0% |

TABLE 3

Protection results obtained with vHVT2 and vHVT4

| Chick group | Number of chicks | Vaccine | Dose (PFU) | No. of dead/ total No. | Positive chicks/ total | Protection % |
|---|---|---|---|---|---|---|
| 1 | 10 | vHVT2 | $10^4$ | 0/10 | 4/10 | 60% |
| 2 | 9 | vHVT2 | $10^3$ | 4/9 | 9/9 | 0% |
| 3 | 11 | vHVT4 | $10^4$ | 0/11 | 0/11 | 100% |
| 4 | 11 | vHVT4 | $10^3$ | 0/11 | 0/11 | 100% |
| 5 | 11 | vHVT4 | $10^2$ | 0/11 | 0/11 | 100% |
| 6 | 10 | parenteral HVT | $10^4$ | 7/10 | 10/10 | 0% |
| 7 | 20 | conventional inactivated | 0.3 ml | 0/20 | 0/20 | 100% |
| 8 | 10 | challenged controls | — | 5/10 | 10/10 | 0% |

For both chicks and adults, the routes of administration which are preferably used for the recombinant vaccines according to the invention are the intramuscular route, the subcutaneous route and the intraperitoneal route. The conventional techniques for injecting embryonated eggs are employed for carrying out in ovo vaccination using the recombinant vaccines according to the invention.

As is conventionally the case for Marek vaccines, the recombinant vaccines according to the invention preferably include, in addition to the virions, cells infected with these virions and/or debris of infected cells.

We claim:

1. A live recombinant Marek's disease virus (MDV) comprising a nucleotide sequence which encodes the VP2 polypeptide of the IBDV virus, and which is inserted in the UL43 gene under the control of a cytomegalovirus (CMV) immediate early (IE) promoter.

2. A live recombinant virus as claimed in claim 1, wherein the virus is herpesvirus of turkey (HVT).

3. A live recombinant virus as claimed in claim 1, characterized in that the nucleotide sequence is inserted into the UL43 gene after total or partial deletion of this gene.

4. A live recombinant virus as claimed in claim 1, characterized in that the CMV immediate early promoter is the human HCMV IE promoter or the murine MCMV IE promoter.

5. A live recombinant virus as claimed in claim 1 wherein it further includes, linked to the CMV immediate early promoter, a second promoter, with a second nucleotide sequence encoding an antigen of another avian disease being inserted in the UL43 gene under the control of the second promoter, and wherein the two promoters are linked such that they transcribe in opposite directions.

6. A live recombinant virus as claimed in claim 5, characterized in that the linked promoter is the Marek 1.8 RNA promoter.

7. A live recombinant virus as claimed in claim 5, characterized in that the nucleotide sequence which encodes an antigen of another avian disease is selected from among the group of the antigens of Marek's disease, Newcastle disease, infectious bronchitis, infectious laryngotracheitis and avian anemia.

8. A live recombinant virus as claimed in claim 5, characterized in that the linked promoter is a CMV immediate early promoter of different origin.

9. A live recombinant virus as claimed in claim 5 wherein the second nucleotide sequence is selected from the group of sequences which encode the genes:

gB, gC, gD and gH+gL of Marek's disease viruses,

VP1(52 kDa)+VP2(24 kDa) of avian anemia virus,

S and M of infectious bronchitis virus, and gB, gC, gD and gH+gL of infectious laryngotracheitis virus.

10. A live recombinant avian vaccine comprising an effective immunizing amount of the virus of claim 1, 2, 3, 4, 5, 6, 7, 8, or 9, and an acceptable vehicle.

11. The vaccine of claim 10, wherein the effective immunizing amount is approximately 10 to $10^4$ pfu per dose.

12. The vaccine of claim 11, wherein the effective immunizing amount is approximately $10^2$ to $10^4$ pfu per dose.

13. A method of immunizing chickens against Gumboro disease, comprising administering the vaccine of claim 10.

* * * * *

SEQUENCE LISTING ( 1 ) GENERAL INFORMATION:

( i i i ) NUMBER OF SEQUENCES: 27

( 2 ) INFORMATION FOR SEQ ID NO:1:

( i ) SEQUENCE CHARACTERISTICS:
        ( A ) LENGTH: 49 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:1:

```
TGCTGGTACC GTCGACAAGC TTGGATCCGT GCAGATAACA CGTACTGGC        49
```

( 2 ) INFORMATION FOR SEQ ID NO:2:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:2:

```
CATGTAACTC GCCTTGATC                                          19
```

( 2 ) INFORMATION FOR SEQ ID NO:3:

( i ) SEQUENCE CHARACTERISTICS:
        ( A ) LENGTH: 2608 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Herpesvirus of turkey
        ( B ) STRAIN: FC126

( x i ) SEQUENCE DESCRIPTION: SEQ ID NO:3:

```
GAGCTCTCCT GGATGGTGGG ACAGGCGCTA CGTCTCAACC AGTTTCATTT CTCGCGACGA    60
ATTACAGCTG GTTTTGCAG CGCCGTCCCG AGAATTAGAT GGTTTATATA CGCGCGTAGT    120
AGTTGTCAAC GGGGACTTTA CTACGGCCGA TATAATGTTT AATGTTAAAG TGGCATGTGC    180
CTTTTCAAAG ACTGGAATAG AAGATGATAC ATTATGCAAA CCCTTTCATT TCTTTGCCAA    240
TGCAACATTG CACAATTTAA CCATGATTAG ATCGGTAACT CTTCGAGCGC ACGAAAGCCA    300
TTTAAAGGAA TGGGTGGCAC GGAGAGGTGG TAACGTCCCT GCAGTGCTAC TTGAGTCTAC    360
```

-continued

```
CATGTATCAT GCATCCAATC TGCCTAGAAA TTTCAGGGAT TTCTACATAA AGTCTCCAGA      420
TGATTATAAG TATAATCACC TAGATGGGCC ATCTGTAATG CTCATCACTG ACAGACCTAG      480
TGAAGATTTG GATGGGAGGC TCGTTCACCA AAGTGACATT TTTACTACTA CAAGTCCTAT      540
AAAACAGGTC CGGTATGAAG AGCATCAGTC ACATACAAAG CAGTATCCTG TAAACAAAAT      600
ACAAGCTATA ATTTTTTTGA TAGGGTTAGG CTCGTTCATT GGAAGCATAT TCGTAGTTTT      660
GGTAGTATGG ATTATACGCA GATATTGCAA TGGAGCGCGG AGTGGGGGAA CGCCCCCCAG      720
TCCTCGCCGG TATGTGTATA CCAGGCTATG ATCACGTGTG AAACTTGGGC GGACCTGTAT      780
CATATGTACA CCGTCCCTAT TCGTTTATAG CCAGTACGTG TTATCTGCAC ATAGAGGAAC      840
ATGTGTCATA CTGGGATCGC ATGCATGGTA TGTGTGACTC TAATATTATT CTGTATCATA      900
ATAAAAACAC AGTGCATGGT ATATAGAGGA TCGCTGGTAA GCACTACGGT AGACCAATCG      960
GCTCAGATTG CATTCTTTGG CATCGATACC GTTGTTAATT TATATGGCAA AGTCTTGTTC     1020
ATGGGAGATC AGTATTTGGA GGAAATATAC TCTGGAACGA TGGAAATACT CAAATGGAAT     1080
CAAGCTAACC GCTGCTATTC TATTGCGCAT GCAACATATT ACGCCGACTG TCCTATAATC     1140
AGTTCTACGG TATTCAGAGG ATGCCGGGAC GCCGTTGTTT ATACTAGGCC CCACAGCAGA     1200
ATTCATCCCC AATATCGAAA CGGGCTGCTT TTGACTATTA TCGAGCCACG GATGGAGGAT     1260
TCTGGTATCT ATTATATACG CACTTCAATA GATGGTTTTA ACAAGAGCGA TTATGCGAGA     1320
ACATCTATTT TTGTATGTAA TGGGTCGTCT GGATCGTGTT CTAACCCCCG CCAAAAAGTT     1380
TCAGATGAAA TGTGCATCCC CCACGTAAAT CGTATTGCAT TGAGCGATA TTTAACCCTA      1440
CATGTTGGAC GGTTGCCCTA CGGAGACTTG ACATTACAGC AGATACGTAA GGACATGACG     1500
ACCACCGCTC CTACATATCG TACCATTCGC AGAACTACAG TTAATGAGGG TTTGTTGACA     1560
GCCAAGACAT CCCTGATAT CGATTTAAAT GCAACAAATT TGCCCCTACC CATTAGTAAC      1620
TACACAGATT ATATGAGTGT TATTTGGAGA CGTGTTGCCT TAAGACGAAT TTATGCTTAT     1680
TTGGTGATCG CTATTATAGC ATTGTTGATA GTAACAGTCT GCTCCGCACA TAAAAGAGGC     1740
AGTTGTAGTC GTCGACGTAG AATCTACATA GGCAATGAAC CTACTACATT GACTTCGATC     1800
ACTAACGGAA ATTTCCAAGA AAAGGAGACC AAGAATGTAC CGTCCGACAT CTCAGACGCT     1860
GAGCTTTTGG AGAGACTCGA GAAGAAGATA GAAATGTTAC GGACTGAATA ATTTCCAAAT     1920
GGCAGTTAGG TACCCAGGAA TGTTGGGATA TGTAGATGTA TTAGCTATAA GTCCGTATTT     1980
AAGGGGAGTG GCCCACCAAT AATAAACTCT GGTATTTTTG TCTGGGAATT CAGTTGTGCT     2040
TTAAGGCGAC CTGCTGTTTC GATATGCGCG CGTGTCGATT ATCCATCCTC ATATTATTAT     2100
TGCAGACGAT CTCGGCGAGT ATGATACAAC ATTTAGATTT ATTAGAGGGG CAATCTGTTG     2160
CAGTCGATAT TCCAAGATAT CCGCCGCTAA CAAACGGTAC TATTTATACT GAAACATGGA     2220
CGTGGATTTC AAGTATTTGC AACGATACAT CGATGGGTTA TATATGTTTG GATCGCGCAA     2280
CGTGTTTTCA GGATTTGCTT TTGGGGACAT CTTGCGTAAG GTATGGTGAA GAAAAGATCT     2340
TGAGGGTGGA TAGATTTGTT GTGAATAGTG GGTCTCTTGA CAGGATAGCG TCTTCTCAGT     2400
TTCATTATAT ACCGAATGTA ATAATAGGCA CTGGACGGGG AAAGGAACTT ACTATCTTCA     2460
ATGCTACATC GCAAATCGCT GGTGTATATA CGCGATATAC CAGGAACGAT AGTAGGCCCG     2520
CTGTAATGGA TGTCCTTTTA GTGTGGGTTT CGGTGCATGG GCAAGCTCCA GATCGTACTA     2580
TGAACATATA TATCACCCCC CCGTCGAC                                        2608
```

( 2 ) INFORMATION FOR SEQ ID NO:4:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:4:

GATCCAGCTG AATTCAGCTA                    20

(2) INFORMATION FOR SEQ ID NO:5:

(i) SEQUENCE CHARACTERISTICS:
    (A) LENGTH: 21 base pairs
    (B) TYPE: nucleic acid
    (C) STRANDEDNESS: single
    (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:5:

AGCTTAAGCT GAATTCAGCT G                  21

(2) INFORMATION FOR SEQ ID NO:6:

(i) SEQUENCE CHARACTERISTICS:
    (A) LENGTH: 3336 base pairs
    (B) TYPE: nucleic acid
    (C) STRANDEDNESS: double
    (D) TOPOLOGY: linear (ii) MOLECULE TYPE: DNA (genomic)

(iii) HYPOTHETICAL: NO (iv) ANTI-SENSE: NO (vi) ORIGINAL SOURCE:
    (A) ORGANISM: Herpesvirus of turkey
    (B) STRAIN: FC126

(ix) FEATURE:
    (A) NAME/KEY: CDS
    (B) LOCATION: 1306..2508
    (D) OTHER INFORMATION: /function="unknown"
        / product="HVT UL43 (HSV-1 UL43 homolog)"
        / gene="UL43"
        / standard_name="UL43"

(xi) SEQUENCE DESCRIPTION: SEQ ID NO:6:

```
GGATCCGAGC TTCTACTATA CAACGCGGAC GATAATTTTG TCCACCCCAT CGGTGTTCGA      60
GAAAGGGTTT TTATGATGGC AGGAATAACT GTCGCATGTG ACCACACTGC AGGAGAGGCT     120
CATACACCCG AGGATATGCA AAAGAAATGG AGGATTATAT TGGCAGGGGA AAAATTCATG     180
ACTATATCGG CATCGTTGAA ATCGATCGTC AGTTGTGTGA AAAACCCCCT TCTCACGTTT     240
GGCGCAGATG GGCTCATTGT ACAAGGTACT GTCTGCGGAC AGCGCATTTT TGTTCCAATC     300
GACCGTGATT CCTTCAGCGA ATATGAATGG CATGGGCCAA CTGCGATGTT TCTAGCATTA     360
ACTGATTCCA GACGCACTCT TTTAGATGCA TTCAAATGTG AAAAGAGAAG GGCAATTGAC     420
GTCTCCTTTA CCTTCGCGGG AGAGCCTCCA TGTAGGCATT TAATCCAAGC CGTCACATAC     480
```

-continued

| | |
|---|---|
| ATGACCGACG GTGGTTCAGT ATCGAATACA ATCATTAAAT ATGAGCTCTG GAATGCGTCT | 540 |
| ACAATTTTCC CCCAAAAAAC TCCCGATGTT ACCTTTTCTC TAAACAAACA ACAATTGAAC | 600 |
| AAAATATTGG CCGTCGCTTC AAAACTGCAA CACGAAGAAC TTGTATTCTC TTTAAAACCT | 660 |
| GAAGGAGGGT TCTACGTAGG AACGGTTTGT ACTGTTATAA GTTTCGAAGT AGATGGGACT | 720 |
| GCCATGACTC AGTATCCTTA CAACCCTCCA ACCTCGGCTA CCCTAGCTCT CGTAGTAGCA | 780 |
| TGCAGAAAGA AGAAGGCGAA TAAAAACACT ATTTTAACGG CCTATGGAAG TGGTAAACCC | 840 |
| TTTTGTGTTG CATTGGAAGA TACTAGTGCA TTTAGAAATA TCGTCAATAA AATCAAGGCG | 900 |
| GGTACGTCGG GAGTTGATCT GGGGTTTTAT ACAACTTGCG ATCCGCCGAT GCTATGTATT | 960 |
| CGCCCACACG CATTTGGAAG TCCTACCGCA TTCCTGTTTT GTAACACAGA CTGTATGACA | 1020 |
| ATATATGAAC TGGAAGAAGT AAGCGCCGTT GATGGTGCAA TCCGAGCAAA ACGCATCAAC | 1080 |
| GAATATTTCC CAACAGTATC GCAGGCTACT TCCAAGAAGA GAAAACAGTC GCCGCCCCT | 1140 |
| ATCGAAAGAG AAAGGAAAAC CACCAGAGCG GATACCCAAT AAAATGCCAG ACAAACCCGG | 1200 |
| CATCCTGGTT AGAGGGCAGG TGGGCTGGGC CAACCTTCAC GGGCGTCCGA CAGATCGGTG | 1260 |
| ACACTCATAC GTTAACTAAA CGCCGGCAGC TTTGCAGAAG AAAAT ATG CCT TCC | 1314 |
| | Met Pro Ser |
| | 1 |

| | | | | | | | | | | | | | | | | |
|---|---|---|---|---|---|---|---|---|---|---|---|---|---|---|---|---|
| GGA | GCC | AGC | TCG | AGT | CCT | CCA | CCA | GCT | TAT | ACA | TCT | GCA | GCT | CCG | CTT | 1362 |
| Gly | Ala | Ser | Ser | Ser | Pro | Pro | Pro | Ala | Tyr | Thr | Ser | Ala | Ala | Pro | Leu | |
| | 5 | | | | | 10 | | | | | 15 | | | | | |
| GAG | ACT | TAT | AAC | AGC | TGG | CTA | AGT | GCC | TTT | TCA | TGC | GCA | TAT | CCC | CAA | 1410 |
| Glu | Thr | Tyr | Asn | Ser | Trp | Leu | Ser | Ala | Phe | Ser | Cys | Ala | Tyr | Pro | Gln | |
| 20 | | | | | 25 | | | | | 30 | | | | | 35 | |
| TGC | ACT | GCG | GGA | AGA | GGA | CAT | CGA | CAA | AAT | GGC | AAG | AAG | TGT | ATA | CGG | 1458 |
| Cys | Thr | Ala | Gly | Arg | Gly | His | Arg | Gln | Asn | Gly | Lys | Lys | Cys | Ile | Arg | |
| | | | | 40 | | | | | 45 | | | | | 50 | | |
| TGT | ATA | GTG | ATC | AGT | GTA | TGT | TCC | TTA | GTG | TGC | ATC | GCT | GCA | CAT | TTA | 1506 |
| Cys | Ile | Val | Ile | Ser | Val | Cys | Ser | Leu | Val | Cys | Ile | Ala | Ala | His | Leu | |
| | | | | 55 | | | | | 60 | | | | | 65 | | |
| GCT | GTT | ACC | GTG | TCG | GGA | GTG | GCA | TTA | ATT | CCG | CTT | ATC | GAT | CAA | AAC | 1554 |
| Ala | Val | Thr | Val | Ser | Gly | Val | Ala | Leu | Ile | Pro | Leu | Ile | Asp | Gln | Asn | |
| | | 70 | | | | | 75 | | | | | 80 | | | | |
| AGA | GCT | TAC | GGA | AAC | TGT | ACG | GTA | TGT | GTA | ATT | GCC | GGA | TTC | ATC | GCT | 1602 |
| Arg | Ala | Tyr | Gly | Asn | Cys | Thr | Val | Cys | Val | Ile | Ala | Gly | Phe | Ile | Ala | |
| | 85 | | | | | 90 | | | | | 95 | | | | | |
| ACG | TTT | GCT | GCA | CGA | CTT | ACG | ATA | AGA | CTT | TCG | GAA | ACG | CTT | ATG | CTA | 1650 |
| Thr | Phe | Ala | Ala | Arg | Leu | Thr | Ile | Arg | Leu | Ser | Glu | Thr | Leu | Met | Leu | |
| 100 | | | | | 105 | | | | | 110 | | | | | 115 | |
| GTG | GGC | AAG | CCG | GCG | CAG | TTT | ATA | TTT | GCT | ATA | ATC | GCT | TCC | GTT | GCG | 1698 |
| Val | Gly | Lys | Pro | Ala | Gln | Phe | Ile | Phe | Ala | Ile | Ile | Ala | Ser | Val | Ala | |
| | | | 120 | | | | | 125 | | | | | 130 | | | |
| GAA | ACA | CTG | ATC | AAT | AAC | GAG | GCG | CTT | GCC | ATC | AGT | AAT | ACT | ACT | TAC | 1746 |
| Glu | Thr | Leu | Ile | Asn | Asn | Glu | Ala | Leu | Ala | Ile | Ser | Asn | Thr | Thr | Tyr | |
| | | | 135 | | | | | 140 | | | | | 145 | | | |
| AAA | ACT | GCA | TTG | CGA | ATA | ATC | GAA | GTA | ACA | TCT | TTG | GCG | TGT | TTT | GTT | 1794 |
| Lys | Thr | Ala | Leu | Arg | Ile | Ile | Glu | Val | Thr | Ser | Leu | Ala | Cys | Phe | Val | |
| | | 150 | | | | | 155 | | | | | 160 | | | | |
| ATG | CTC | GGG | GCA | ATA | ATT | ACA | TCC | CAC | AAC | TAT | GTC | TGC | ATT | TCA | ACG | 1842 |
| Met | Leu | Gly | Ala | Ile | Ile | Thr | Ser | His | Asn | Tyr | Val | Cys | Ile | Ser | Thr | |
| | 165 | | | | | 170 | | | | | 175 | | | | | |
| GCA | GGG | GAC | TTG | ACT | TGG | AAG | GCG | GGA | TTT | TTC | ATG | CTT | ACC | ACC | GGA | 1890 |
| Ala | Gly | Asp | Leu | Thr | Trp | Lys | Ala | Gly | Phe | Phe | Met | Leu | Thr | Thr | Gly | |
| 180 | | | | | 185 | | | | | 190 | | | | | 195 | |
| ACA | TTA | CTC | GGT | ATA | ACA | ATA | CCA | AAC | ATA | CAC | CCA | ATC | CCT | CTC | GCG | 1938 |
| Thr | Leu | Leu | Gly | Ile | Thr | Ile | Pro | Asn | Ile | His | Pro | Ile | Pro | Leu | Ala | |

```
                    200                         205                         210
GGG TTT CTT GCA GTC TAT ACA ATA TTG GCT ATA AAT ATC GCT AGA GAT          1986
Gly Phe Leu Ala Val Tyr Thr Ile Leu Ala Ile Asn Ile Ala Arg Asp
            215                 220                 225

GCA AGC GCT ACA TTA TTA TCC ACT TGC TAT TAT CGC AAT TGC CGC GAG          2034
Ala Ser Ala Thr Leu Leu Ser Thr Cys Tyr Tyr Arg Asn Cys Arg Glu
            230                 235                 240

AGG ACT ATA CTT CGC CCT TCT CGT CTC GGA CAT GGT TAC ACA ATC CCT          2082
Arg Thr Ile Leu Arg Pro Ser Arg Leu Gly His Gly Tyr Thr Ile Pro
    245                 250                 255

TCT CCC GGT GCC GAT ATG CTT TAT GAA GAA GAC GTA TAT AGT TTT GAC          2130
Ser Pro Gly Ala Asp Met Leu Tyr Glu Glu Asp Val Tyr Ser Phe Asp
260                 265                 270                 275

GCA GCT AAA GGC CAT TAT TCG TCA ATA TTT CTA TGT TAT GCC ATG GGG          2178
Ala Ala Lys Gly His Tyr Ser Ser Ile Phe Leu Cys Tyr Ala Met Gly
                280                 285                 290

CTT ACA ACA CCG CTG ATT ATT GCG CTC CAT AAA TAT ATG GCG GGC ATT          2226
Leu Thr Thr Pro Leu Ile Ile Ala Leu His Lys Tyr Met Ala Gly Ile
                295                 300                 305

AAA AAT TCG TCA GAT TGG ACT GCT ACA TTA CAA GGC ATG TAC GGG CTT          2274
Lys Asn Ser Ser Asp Trp Thr Ala Thr Leu Gln Gly Met Tyr Gly Leu
            310                 315                 320

GTC TTG GGA TCG CTA TCG TCA CTA TGT ATT CCA TCC AGC AAC AAC GAT          2322
Val Leu Gly Ser Leu Ser Ser Leu Cys Ile Pro Ser Ser Asn Asn Asp
    325                 330                 335

GCC CTA ATT CGT CCC ATT CAA ATT TTG ATA TTG ATA ATC GGT GCA CTG          2370
Ala Leu Ile Arg Pro Ile Gln Ile Leu Ile Leu Ile Ile Gly Ala Leu
340                 345                 350                 355

GCC ATT GCA TTG GCT GGA TGT GGT CAA ATT ATA GGG CCT ACA TTA TTT          2418
Ala Ile Ala Leu Ala Gly Cys Gly Gln Ile Ile Gly Pro Thr Leu Phe
                360                 365                 370

GCC GCG AGT TCG GCT GCG ATG TCA TGT TTT ACA TGT ATC AAT ATT CGC          2466
Ala Ala Ser Ser Ala Ala Met Ser Cys Phe Thr Cys Ile Asn Ile Arg
                375                 380                 385

GCT ACT AAT AAG GGT GTC AAC AAA TTG GCA GCA GCA GTG TCG                  2508
Ala Thr Asn Lys Gly Val Asn Lys Leu Ala Ala Ala Val Ser
            390                 395                 400

TGAAATCTGT ACTGGGCTTC ATTATTTCCG GGATGCTTAC TTGCGTGCTA TTACCACTAT        2568
CGTGATAGAT CGTCGGTCTG CGCATCGCCC ATGCTGGCGG AACGCTCTTT CGAACCGTGA        2628
ATAAAACTTT GTATCTACTA AACAATAACT TTGTGTTTTA TTGAGCGGTC GAAAACAATG        2688
AGGAGCTGCA ATTTAAAGCT AACCGCATAC GCCGGGCGGG TAAAGACCAT TTTATACCAT        2748
ATTACGCATC TATCGAAACT TGTTCGAGAA CCGCAAGTAT ATGGTTTCCA ACATGCGTTC        2808
TACGCGTACT GCGCTGACGG GATGGGTGGG CATATTTCTA GTTCTGTCTT TACAGCAAAC        2868
CTCTTGTGCC GGATTGCCCC ATAACGTCGA TACCCATCAT ATCCTAACTT TCAACCCTTC        2928
TCCCATTTCG GCCGATGGCG TTCCTTTGTC AGAGGTGCCC AATTCGCCTA CGACCGAATT        2988
ATCTACAACT GTCGCCACCA AGACAGCTGT ACCGACGACT GAAAGCACTA GTTCCTCCGA        3048
AGCGCACCGC AACTCTTCTC ACAAAATACC TGATATAATC TGCGACCGAG AAGAAGTATT        3108
CGTATTCCTT AACAATACAG GAAGAATTTT GTGTGACCTT ATAGTCGACC CCCCTTCAGA        3168
CGATGAATGG TCCAACTTCG CTCTTGACGT CACGTTCAAT CCAATCGAAT ACCACGCCAA        3228
CGAAAAGAAT GTAGAGGTTG CCCGAGTGGC CGGTCTATAC GGAGTACCGG GTCGGATTA        3288
TGCATACCCT AGGAAATCGG AATTAATATC CTCCATTCGA CGGGATCC                     3336
```

( 2 ) INFORMATION FOR SEQ ID NO:7:

( i ) SEQUENCE CHARACTERISTICS:
    ( A ) LENGTH: 401 amino acids
    ( B ) TYPE: amino acid
    ( D ) TOPOLOGY: linear ( i i ) MOLECULE TYPE: protein ( x i ) SEQUENCE DESCRIPTION: SEQ ID NO:7:

```
Met Pro Ser Gly Ala Ser Ser Ser Pro Pro Pro Ala Tyr Thr Ser Ala
 1               5                  10                  15
Ala Pro Leu Glu Thr Tyr Asn Ser Trp Leu Ser Ala Phe Ser Cys Ala
            20                  25                  30
Tyr Pro Gln Cys Thr Ala Gly Arg Gly His Arg Gln Asn Gly Lys Lys
        35                  40                  45
Cys Ile Arg Cys Ile Val Ile Ser Val Cys Ser Leu Val Cys Ile Ala
    50                  55                  60
Ala His Leu Ala Val Thr Val Ser Gly Val Ala Leu Ile Pro Leu Ile
 65                  70                  75                  80
Asp Gln Asn Arg Ala Tyr Gly Asn Cys Thr Val Cys Val Ile Ala Gly
                85                  90                  95
Phe Ile Ala Thr Phe Ala Ala Arg Leu Thr Ile Arg Leu Ser Glu Thr
            100                 105                 110
Leu Met Leu Val Gly Lys Pro Ala Gln Phe Ile Phe Ala Ile Ile Ala
        115                 120                 125
Ser Val Ala Glu Thr Leu Ile Asn Asn Glu Ala Leu Ala Ile Ser Asn
    130                 135                 140
Thr Thr Tyr Lys Thr Ala Leu Arg Ile Ile Glu Val Thr Ser Leu Ala
145                 150                 155                 160
Cys Phe Val Met Leu Gly Ala Ile Ile Thr Ser His Asn Tyr Val Cys
                165                 170                 175
Ile Ser Thr Ala Gly Asp Leu Thr Trp Lys Ala Gly Phe Phe Met Leu
            180                 185                 190
Thr Thr Gly Thr Leu Leu Gly Ile Thr Ile Pro Asn Ile His Pro Ile
        195                 200                 205
Pro Leu Ala Gly Phe Leu Ala Val Tyr Thr Ile Leu Ala Ile Asn Ile
    210                 215                 220
Ala Arg Asp Ala Ser Ala Thr Leu Leu Ser Thr Cys Tyr Tyr Arg Asn
225                 230                 235                 240
Cys Arg Glu Arg Thr Ile Leu Arg Pro Ser Arg Leu Gly His Gly Tyr
                245                 250                 255
Thr Ile Pro Ser Pro Gly Ala Asp Met Leu Tyr Glu Glu Asp Val Tyr
            260                 265                 270
Ser Phe Asp Ala Ala Lys Gly His Tyr Ser Ser Ile Phe Leu Cys Tyr
        275                 280                 285
Ala Met Gly Leu Thr Thr Pro Leu Ile Ile Ala Leu His Lys Tyr Met
290                 295                 300
Ala Gly Ile Lys Asn Ser Ser Asp Trp Thr Ala Thr Leu Gln Gly Met
305                 310                 315                 320
Tyr Gly Leu Val Leu Gly Ser Leu Ser Ser Leu Cys Ile Pro Ser Ser
                325                 330                 335
Asn Asn Asp Ala Leu Ile Arg Pro Ile Gln Ile Leu Ile Leu Ile Ile
            340                 345                 350
Gly Ala Leu Ala Ile Ala Leu Ala Gly Cys Gly Gln Ile Ile Gly Pro
        355                 360                 365
Thr Leu Phe Ala Ala Ser Ser Ala Ala Met Ser Cys Phe Thr Cys Ile
```

|     |     |     | 370 |     |     |     | 375 |     |     |     | 380 |     |     |
| --- | --- | --- | --- | --- | --- | --- | --- | --- | --- | --- | --- | --- | --- |
| Asn | Ile | Arg | Ala | Thr | Asn | Lys | Gly | Val | Asn | Lys | Leu | Ala | Ala | Ala | Val |
| 385 |     |     |     |     | 390 |     |     |     |     | 395 |     |     |     |     | 400 |

Ser ( 2 ) INFORMATION FOR SEQ ID NO:8:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

TCGAGAATTC AGATCTGATA TCAAGCTTGG TACCGTCGAC        40

( 2 ) INFORMATION FOR SEQ ID NO:9:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

CATGGTCGAC GGTACCAAGC TTGATATCAG ATCTGAATTC        40

( 2 ) INFORMATION FOR SEQ ID NO:10:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

CGAATTCACT AGTGTGTGTC TGCAGGCGGC CGCGTGTGTG TCGACGGTAC        50

( 2 ) INFORMATION FOR SEQ ID NO:11:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

CGTCGACACA CACGCGGCCG CCTGCAGACA CACACTAGTG AATTCGAGCT        50

( 2 ) INFORMATION FOR SEQ ID NO:12:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

```
GACTGGTACC  GCGGCCGCAT  GCACTTTTTA  GGCGGAATTG                                    40
```

( 2 ) INFORMATION FOR SEQ ID NO:13:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

```
TTCGGGACAT  TTTCGCGG                                                              18
```

( 2 ) INFORMATION FOR SEQ ID NO:14:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

```
TATATGGCGT  TAGTCTCC                                                              18
```

( 2 ) INFORMATION FOR SEQ ID NO:15:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

```
TTGCGAGCTC  GCGGCCGCTT  ATTACACAGC  ATCATCTTCT  G                                 41
```

( 2 ) INFORMATION FOR SEQ ID NO:16:

( i ) SEQUENCE CHARACTERISTICS:
        ( A ) LENGTH: 2521 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Newcastle disease virus
        ( B ) STRAIN: Texas ( i x ) FEATURE:
        ( A ) NAME/KEY: CDS
        ( B ) LOCATION: 303..2015
        ( D ) OTHER INFORMATION: /codon_start=303
            / function="neuraminidase"
            / product="hemagglutinin neuraminidase"
            / gene="HN"
            / standard_name="hemagglutinin neuraminidase"
            / label=HN ( x i ) SEQUENCE DESCRIPTION: SEQ ID NO:16:

```
TGCTACCTGA  TGTACAAGCA  AAAGGCACAA  CAAAAGACCT  TGTTATGGCT  TGGGAATAAT            60
```

-continued

```
ACCCTTGATC AGATGAGAGC CACTACAAAA ATATGAATAC AAACGAGAGG CGGAGGTATC      120

CCCAATAGCA ATTTGCGTGT AAATTCTGGC AACCTGTTAA TTAGAAGAAT TAAGAAAAAA      180

CCACTGGATG TAAGTGACAA ACAAGCAATA CACGGGTAGA ACGGTCGGAG AAGCCACCCC      240

TCAATCGGGA ATCAGGCCTC ACAACGTCCT TTCTACCGCA TCATCAATAG CAGACTTCGG      300
```

| | | | | | | | | | | | | | | | | |
|---|---|---|---|---|---|---|---|---|---|---|---|---|---|---|---|---|
| TC ATG | GAC | CGT | GCA | GTT | AGC | AGA | GTT | GCG | CTA | GAG | AAT | GAA | GAA | AGA | | 347 |
| Met | Asp | Arg | Ala | Val | Ser | Arg | Val | Ala | Leu | Glu | Asn | Glu | Glu | Arg | | |
| 1 | | | | 5 | | | | | 10 | | | | | 15 | | |
| GAA | GCA | AAG | AAT | ACA | TGG | CGC | TTT | GTA | TTC | CGG | ATT | GCA | ATC | TTA | CTT | 395 |
| Glu | Ala | Lys | Asn | Thr | Trp | Arg | Phe | Val | Phe | Arg | Ile | Ala | Ile | Leu | Leu | |
| | | | | 20 | | | | | 25 | | | | | 30 | | |
| TTA | ATA | GTA | ACA | ACC | TTA | GCC | ATC | TCT | GCA | ACC | GCC | CTG | GTA | TAT | AGC | 443 |
| Leu | Ile | Val | Thr | Thr | Leu | Ala | Ile | Ser | Ala | Thr | Ala | Leu | Val | Tyr | Ser | |
| | | | 35 | | | | | 40 | | | | | 45 | | | |
| ATG | GAG | GCT | AGC | ACG | CCT | GGC | GAC | CTT | GTT | GGC | ATA | CCG | ACT | ATG | ATC | 491 |
| Met | Glu | Ala | Ser | Thr | Pro | Gly | Asp | Leu | Val | Gly | Ile | Pro | Thr | Met | Ile | |
| | | 50 | | | | | 55 | | | | | 60 | | | | |
| TCT | AAG | GCA | GAA | GAA | AAG | ATT | ACA | TCT | GCA | CTC | AGT | TCT | AAT | CAA | GAT | 539 |
| Ser | Lys | Ala | Glu | Glu | Lys | Ile | Thr | Ser | Ala | Leu | Ser | Ser | Asn | Gln | Asp | |
| | 65 | | | | | 70 | | | | | 75 | | | | | |
| GTA | GTA | GAT | AGG | ATA | TAT | AAG | CAG | GTG | GCC | CTT | GAG | TCT | CCA | TTG | GCG | 587 |
| Val | Val | Asp | Arg | Ile | Tyr | Lys | Gln | Val | Ala | Leu | Glu | Ser | Pro | Leu | Ala | |
| 80 | | | | | 85 | | | | | 90 | | | | | 95 | |
| TTG | CTA | AAC | ACT | GAA | TCT | GTA | ATT | ATG | AAT | GCA | ATA | ACG | TCT | CTC | TCT | 635 |
| Leu | Leu | Asn | Thr | Glu | Ser | Val | Ile | Met | Asn | Ala | Ile | Thr | Ser | Leu | Ser | |
| | | | | 100 | | | | | 105 | | | | | 110 | | |
| TAT | CAA | ATC | AAT | GGA | GCT | GCA | AAT | AAT | AGC | GGG | TGT | GGG | GCA | CCT | GTT | 683 |
| Tyr | Gln | Ile | Asn | Gly | Ala | Ala | Asn | Asn | Ser | Gly | Cys | Gly | Ala | Pro | Val | |
| | | | 115 | | | | | 120 | | | | | 125 | | | |
| CAT | GAC | CCA | GAT | TAT | ATC | GGG | GGG | ATA | GGC | AAA | GAA | CTT | ATT | GTG | GAT | 731 |
| His | Asp | Pro | Asp | Tyr | Ile | Gly | Gly | Ile | Gly | Lys | Glu | Leu | Ile | Val | Asp | |
| | | 130 | | | | | 135 | | | | | 140 | | | | |
| GAC | GCT | AGT | GAT | GTC | ACA | TCA | TTC | TAT | CCC | TCT | GCG | TTC | CAA | GAA | CAC | 779 |
| Asp | Ala | Ser | Asp | Val | Thr | Ser | Phe | Tyr | Pro | Ser | Ala | Phe | Gln | Glu | His | |
| | 145 | | | | | 150 | | | | | 155 | | | | | |
| CTG | AAC | TTT | ATC | CCG | GCA | CCT | ACT | ACA | GGA | TCA | GGT | TGC | ACT | CGG | ATA | 827 |
| Leu | Asn | Phe | Ile | Pro | Ala | Pro | Thr | Thr | Gly | Ser | Gly | Cys | Thr | Arg | Ile | |
| 160 | | | | | 165 | | | | | 170 | | | | | 175 | |
| CCC | TCA | TTC | GAC | ATA | AGC | GCT | ACC | CAC | TAC | TGT | TAC | ACT | CAC | AAT | GTG | 875 |
| Pro | Ser | Phe | Asp | Ile | Ser | Ala | Thr | His | Tyr | Cys | Tyr | Thr | His | Asn | Val | |
| | | | | 180 | | | | | 185 | | | | | 190 | | |
| ATA | TTA | TCT | GGT | TGC | AGA | GAT | CAC | TCA | CAC | TCA | TAT | CAG | TAC | TTA | GCA | 923 |
| Ile | Leu | Ser | Gly | Cys | Arg | Asp | His | Ser | His | Ser | Tyr | Gln | Tyr | Leu | Ala | |
| | | | 195 | | | | | 200 | | | | | 205 | | | |
| CTT | GGC | GTG | CTT | CGG | ACA | TCT | GCA | ACA | GGG | AGG | GTA | TTC | TTT | TCT | ACT | 971 |
| Leu | Gly | Val | Leu | Arg | Thr | Ser | Ala | Thr | Gly | Arg | Val | Phe | Phe | Ser | Thr | |
| | | 210 | | | | | 215 | | | | | 220 | | | | |
| CTG | CGT | TCC | ATC | AAT | TTG | GAT | GAC | AGC | CAA | AAT | CGG | AAG | TCT | TGC | AGT | 1019 |
| Leu | Arg | Ser | Ile | Asn | Leu | Asp | Asp | Ser | Gln | Asn | Arg | Lys | Ser | Cys | Ser | |
| | 225 | | | | | 230 | | | | | 235 | | | | | |
| GTG | AGT | GCA | ACT | CCC | TTA | GGT | TGT | GAT | ATG | CTG | TGC | TCT | AAA | ATC | ACA | 1067 |
| Val | Ser | Ala | Thr | Pro | Leu | Gly | Cys | Asp | Met | Leu | Cys | Ser | Lys | Ile | Thr | |
| 240 | | | | | 245 | | | | | 250 | | | | | 255 | |
| GAG | ACT | GAG | GAA | GAG | GAT | TAT | AGT | TCA | ATT | ACG | CCT | ACA | TCG | ATG | GTG | 1115 |
| Glu | Thr | Glu | Glu | Glu | Asp | Tyr | Ser | Ser | Ile | Thr | Pro | Thr | Ser | Met | Val | |
| | | | | 260 | | | | | 265 | | | | | 270 | | |
| CAC | GGA | AGG | TTA | GGG | TTT | GAC | GGT | CAA | TAC | CAT | GAG | AAG | GAC | TTA | GAC | 1163 |
| His | Gly | Arg | Leu | Gly | Phe | Asp | Gly | Gln | Tyr | His | Glu | Lys | Asp | Leu | Asp |  |
| | | | 275 | | | | | 280 | | | | | 285 | | | |

```
GTC ATA ACT TTA TTT AAG GAT TGG GTG GCA AAT TAC CCA GGA GTG GGG    1211
Val Ile Thr Leu Phe Lys Asp Trp Val Ala Asn Tyr Pro Gly Val Gly
        290                 295                 300

GGT GGG TCT TTT ATT AAC AAC CGC GTA TGG TTC CCA GTC TAC GGA GGG    1259
Gly Gly Ser Phe Ile Asn Asn Arg Val Trp Phe Pro Val Tyr Gly Gly
    305                 310                 315

CTA AAA CCC AAT TCG CCT AGT GAC ACC GCA CAA GAA GGG AGA TAT GTA    1307
Leu Lys Pro Asn Ser Pro Ser Asp Thr Ala Gln Glu Gly Arg Tyr Val
320                 325                 330                 335

ATA TAC AAG CGC TAC AAT GAC ACA TGC CCA GAT GAA CAA GAT TAC CAG    1355
Ile Tyr Lys Arg Tyr Asn Asp Thr Cys Pro Asp Glu Gln Asp Tyr Gln
                340                 345                 350

ATT CGG ATG GCT AAG TCT TCA TAT AAG CCT GGG CGG TTT GGT GGA AAA    1403
Ile Arg Met Ala Lys Ser Ser Tyr Lys Pro Gly Arg Phe Gly Gly Lys
            355                 360                 365

CGC GTA CAG CAG GCC ATC TTA TCT ATC AAG GTG TCA ACA TCT TTG GGC    1451
Arg Val Gln Gln Ala Ile Leu Ser Ile Lys Val Ser Thr Ser Leu Gly
        370                 375                 380

GAG GAC CCG GTG CTG ACT GTA CCG CCT AAT ACA ATC ACA CTC ATG GGG    1499
Glu Asp Pro Val Leu Thr Val Pro Pro Asn Thr Ile Thr Leu Met Gly
    385                 390                 395

GCC GAA GGC AGA GTT CTC ACA GTA GGG ACA TCT CAT TTC TTG TAC CAG    1547
Ala Glu Gly Arg Val Leu Thr Val Gly Thr Ser His Phe Leu Tyr Gln
400                 405                 410                 415

CGA GGG TCT TCA TAC TTC TCT CCT GCT TTA TTA TAC CCT ATG ACA GTC    1595
Arg Gly Ser Ser Tyr Phe Ser Pro Ala Leu Leu Tyr Pro Met Thr Val
                420                 425                 430

AAC AAC AAA ACG GCT ACT CTT CAT AGT CCT TAC ACA TTC AAT GCT TTC    1643
Asn Asn Lys Thr Ala Thr Leu His Ser Pro Tyr Thr Phe Asn Ala Phe
            435                 440                 445

ACT AGG CCA GGT AGT GTC CCT TGT CAG GCA TCA GCA AGA TGC CCC AAC    1691
Thr Arg Pro Gly Ser Val Pro Cys Gln Ala Ser Ala Arg Cys Pro Asn
        450                 455                 460

TCA TGT GTC ACT GGA GTT TAT ACT GAT CCG TAT CCC TTA GTC TTC CAT    1739
Ser Cys Val Thr Gly Val Tyr Thr Asp Pro Tyr Pro Leu Val Phe His
    465                 470                 475

AGG AAC CAT ACC TTG CGG GGG GTA TTC GGG ACA ATG CTT GAT GAT GAA    1787
Arg Asn His Thr Leu Arg Gly Val Phe Gly Thr Met Leu Asp Asp Glu
480                 485                 490                 495

CAA GCA AGA CTT AAC CCT GTA TCT GCA GTA TTT GAT AAC ATA TCC CGC    1835
Gln Ala Arg Leu Asn Pro Val Ser Ala Val Phe Asp Asn Ile Ser Arg
                500                 505                 510

AGT CGC ATA ACC CGG GTA AGT TCA AGC CGT ACT AAG GCA GCA TAC ACG    1883
Ser Arg Ile Thr Arg Val Ser Ser Ser Arg Thr Lys Ala Ala Tyr Thr
            515                 520                 525

ACA TCG ACA TGT TTT AAA GTT GTC AAG ACC AAT AAA ACA TAT TGC CTC    1931
Thr Ser Thr Cys Phe Lys Val Val Lys Thr Asn Lys Thr Tyr Cys Leu
        530                 535                 540

AGC ATT GCA GAA ATA TCC AAT ACC CTC TTC GGG GAA TTC AGG ATC GTT    1979
Ser Ile Ala Glu Ile Ser Asn Thr Leu Phe Gly Glu Phe Arg Ile Val
    545                 550                 555

CCT TTA CTA GTT GAG ATT CTC AAG GAT GAT GGG ATT TAAGAAGCTT         2025
Pro Leu Leu Val Glu Ile Leu Lys Asp Asp Gly Ile
560                 565                 570

GGTCTGGCCA GTTGAGTCAA CTGCGAGAGG GTCGGAAAGA TGACATTGTG TCACCTTTTT   2085

TTTGTAATGC CAAGGATCAA ACTGGATACC GGCGCGAGCC CGAATCCTAT GCTGCCAGTC   2145

AGCCATAATC AGATAGTACT AATATGATTA GTCTTAATCT TGTCGATAGT AACTTGGTTA   2205

AGAAAAAATA TGAGTGGTAG TGAGATACAC AGCTAAACAA CTCACGAGAG ATAGCACGGG   2265
```

```
TAGGACATGG CGAGCTCCGG TCCCGAAAGG GCAGAGCATC AGATTATCCT ACCAGAGTCA    2325

CATCTGTCCT CACCATTGGT CAAGCACAAA CTGCTCTATT ACTGGAAATT AACTGGCGTA    2385

CCGCTTCCTG ACGAATGTGA CTTCGACCAC CTCATTATCA GCCGACAATG GAAGAAAATA    2445

CTTGAATCGG CCACTCCTGA CACTGAGAGG ATGATAAAGC TCGGGCGGGC AGTACACCAG    2505

ACTCTCGACC ACCGCC                                                    2521
```

( 2 ) INFORMATION FOR SEQ ID NO:17:

( i ) SEQUENCE CHARACTERISTICS:
        ( A ) LENGTH: 571 amino acids
        ( B ) TYPE: amino acid
        ( D ) TOPOLOGY: linear ( i i ) MOLECULE TYPE: protein ( x i ) SEQUENCE DESCRIPTION: SEQ ID NO:17:

```
Met Asp Arg Ala Val Ser Arg Val Ala Leu Glu Asn Glu Arg Glu
 1               5                  10                  15

Ala Lys Asn Thr Trp Arg Phe Val Phe Arg Ile Ala Ile Leu Leu Leu
                20                  25                  30

Ile Val Thr Thr Leu Ala Ile Ser Ala Thr Ala Leu Val Tyr Ser Met
                35                  40                  45

Glu Ala Ser Thr Pro Gly Asp Leu Val Gly Ile Pro Thr Met Ile Ser
        50                  55                  60

Lys Ala Glu Glu Lys Ile Thr Ser Ala Leu Ser Ser Asn Gln Asp Val
65                  70                  75                  80

Val Asp Arg Ile Tyr Lys Gln Val Ala Leu Glu Ser Pro Leu Ala Leu
                85                  90                  95

Leu Asn Thr Glu Ser Val Ile Met Asn Ala Ile Thr Ser Leu Ser Tyr
                100                 105                 110

Gln Ile Asn Gly Ala Ala Asn Asn Ser Gly Cys Gly Ala Pro Val His
                115                 120                 125

Asp Pro Asp Tyr Ile Gly Gly Ile Gly Lys Glu Leu Ile Val Asp Asp
        130                 135                 140

Ala Ser Asp Val Thr Ser Phe Tyr Pro Ser Ala Phe Gln Glu His Leu
145                 150                 155                 160

Asn Phe Ile Pro Ala Pro Thr Thr Gly Ser Gly Cys Thr Arg Ile Pro
                165                 170                 175

Ser Phe Asp Ile Ser Ala Thr His Tyr Cys Tyr Thr His Asn Val Ile
                180                 185                 190

Leu Ser Gly Cys Arg Asp His Ser His Ser Tyr Gln Tyr Leu Ala Leu
                195                 200                 205

Gly Val Leu Arg Thr Ser Ala Thr Gly Arg Val Phe Phe Ser Thr Leu
        210                 215                 220

Arg Ser Ile Asn Leu Asp Asp Ser Gln Asn Arg Lys Ser Cys Ser Val
225                 230                 235                 240

Ser Ala Thr Pro Leu Gly Cys Asp Met Leu Cys Ser Lys Ile Thr Glu
                245                 250                 255

Thr Glu Glu Glu Asp Tyr Ser Ser Ile Thr Pro Thr Ser Met Val His
                260                 265                 270

Gly Arg Leu Gly Phe Asp Gly Gln Tyr His Glu Lys Asp Leu Asp Val
                275                 280                 285

Ile Thr Leu Phe Lys Asp Trp Val Ala Asn Tyr Pro Gly Val Gly Gly
        290                 295                 300

Gly Ser Phe Ile Asn Asn Arg Val Trp Phe Pro Val Tyr Gly Gly Leu
```

|         |     |     |     |     |     |     |     |     |     |     |     |     |     |     |     |
|---------|-----|-----|-----|-----|-----|-----|-----|-----|-----|-----|-----|-----|-----|-----|-----|
| 305 |  |  |  |  | 310 |  |  |  |  | 315 |  |  |  |  | 320 |

Lys Pro Asn Ser Pro Ser Asp Thr Ala Gln Glu Gly Arg Tyr Val Ile
                    325                 330                 335

Tyr Lys Arg Tyr Asn Asp Thr Cys Pro Asp Glu Gln Asp Tyr Gln Ile
                340                 345                 350

Arg Met Ala Lys Ser Ser Tyr Lys Pro Gly Arg Phe Gly Gly Lys Arg
            355                 360                 365

Val Gln Gln Ala Ile Leu Ser Ile Lys Val Ser Thr Ser Leu Gly Glu
        370                 375                 380

Asp Pro Val Leu Thr Val Pro Pro Asn Thr Ile Thr Leu Met Gly Ala
385                     390                 395                 400

Glu Gly Arg Val Leu Thr Val Gly Thr Ser His Phe Leu Tyr Gln Arg
                405                 410                 415

Gly Ser Ser Tyr Phe Ser Pro Ala Leu Leu Tyr Pro Met Thr Val Asn
            420                 425                 430

Asn Lys Thr Ala Thr Leu His Ser Pro Tyr Thr Phe Asn Ala Phe Thr
        435                 440                 445

Arg Pro Gly Ser Val Pro Cys Gln Ala Ser Ala Arg Cys Pro Asn Ser
    450                 455                 460

Cys Val Thr Gly Val Tyr Thr Asp Pro Tyr Pro Leu Val Phe His Arg
465                 470                 475                     480

Asn His Thr Leu Arg Gly Val Phe Gly Thr Met Leu Asp Asp Glu Gln
                485                 490                 495

Ala Arg Leu Asn Pro Val Ser Ala Val Phe Asp Asn Ile Ser Arg Ser
            500                 505                 510

Arg Ile Thr Arg Val Ser Ser Ser Arg Thr Lys Ala Ala Tyr Thr Thr
        515                 520                 525

Ser Thr Cys Phe Lys Val Val Lys Thr Asn Lys Thr Tyr Cys Leu Ser
    530                 535                 540

Ile Ala Glu Ile Ser Asn Thr Leu Phe Gly Glu Phe Arg Ile Val Pro
545                 550                 555                     560

Leu Leu Val Glu Ile Leu Lys Asp Asp Gly Ile
                565                 570

( 2 ) INFORMATION FOR SEQ ID NO:18:

( i ) SEQUENCE CHARACTERISTICS:
       ( A ) LENGTH: 22 base pairs
       ( B ) TYPE: nucleic acid
       ( C ) STRANDEDNESS: single
       ( D ) TOPOLOGY: linear ( i i ) MOLECULE TYPE: DNA (genomic)

( x i ) SEQUENCE DESCRIPTION: SEQ ID NO:18:

CAGACCAAGC TTCTTAAATC CC                                            22

( 2 ) INFORMATION FOR SEQ ID NO:19:

( i ) SEQUENCE CHARACTERISTICS:
       ( A ) LENGTH: 16 base pairs
       ( B ) TYPE: nucleic acid
       ( C ) STRANDEDNESS: single
       ( D ) TOPOLOGY: linear ( i i ) MOLECULE TYPE: DNA (genomic)

( x i ) SEQUENCE DESCRIPTION: SEQ ID NO:19:

GTATTCGGGA CAATGC                                                   16

( 2 ) INFORMATION FOR SEQ ID NO:20:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:20:

GTGACATCAC TAGCGTCATC C                                      21

( 2 ) INFORMATION FOR SEQ ID NO:21:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:21:

CCGCATCATC AGCGGCCGCG ATCGGTCATG GACAGT                36

( 2 ) INFORMATION FOR SEQ ID NO:22:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:22:

TGACCCTGTC TGGGATGA                                          18

( 2 ) INFORMATION FOR SEQ ID NO:23:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:23:

GGATCCCGGT CGACACATTG CGGCCGCAAG ATGGGC                36

( 2 ) INFORMATION FOR SEQ ID NO:24:

( i ) SEQUENCE CHARACTERISTICS:
        ( A ) LENGTH: 800 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Marek's disease gammaherpesvirus
        ( B ) STRAIN: RB1B ( x i ) SEQUENCE DESCRIPTION: SEQ ID NO:24:

| | | | | | |
|---|---|---|---|---|---|
|GAATTCCATC|ACCCCCTGCC|GATCTTGCAC|GCGGGGACGA|GCAAAGCGTG|CGGTGCGGGC 60|
|AGAAAGACAA|GGATGGCTGT|GGGTTGAAAG|ATGAAAAACA|AATCGCGGTT|GTGGGTCATG 120|
|AGTGGAGGGA|GGGTGCCATC|TGTGATGCCG|AGAGGTCAAA|CTATGTTATA|AAGAAAAACG 180|
|ATGGGTGGGA|AATATAATAA|AGCAACCGAA|ATGGTACATA|AAAACTAAAA|ATACCTACAC 240|
|GGTTACACCA|CCGATCAGGC|GAAGAAGTTC|CAAACGATTA|ACAACGGGA|CGAGACGTTG 300|
|CCGTTCGATC|CAGGTCTCTG|CTTTTTTGTA|TCTCTTATCC|TATACCGCCG|CCTCCCGTCC 360|
|GACGAGAGCA|AGTCGCACCG|CCACTCGAGG|CCACAAGAAA|TTACGATTCT|TATACGGGTG 420|
|GGCGTACCGC|CTACTCGAAC|TATCACGTGA|TGTGTATGCA|AATGAGCAGT|GCGAACGCGT 480|
|CAGCGTTCGC|ACTGCGAACC|AATAATATAT|TATATTATAT|TATATTATTG|GACTCTGGTG 540|
|CGAACGCCGA|GGTGAGCCAA|TCGGATATGG|CGATATGTTA|TCACGTGACA|TGTACCGCCC 600|
|CAAATTCGCA|CTTGAGTGTT|GGGGTACAT|GTGGGGGCGG|CTCGGCTCTT|GTGTATAAAA 660|
|GAGCGGCGGT|TGCGAGGTTC|CTTCTCTCTT|CGCGATGCTC|TCTCAGAATG|GCACGGCCGA 720|
|TCCCCCATAT|ATTTCCTGAA|GGAACGCATA|GCTAGGCGAC|GAACGAGCTG|AATTTCTCCC 780|
|TTCATCAAAT|AAGTAATAAA| | | |800|

( 2 ) INFORMATION FOR SEQ ID NO:25:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:25:

GGTCTACTAG TATTGGACTC TGGTGCGAAC GC      32

( 2 ) INFORMATION FOR SEQ ID NO:26:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:26:

GTCCAGAATT CGCGAAGAGA GAAGGAACCT C      31

( 2 ) INFORMATION FOR SEQ ID NO:27:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO

```
( i v ) ANTI-SENSE: NO ( x i ) SEQUENCE DESCRIPTION: SEQ ID NO:27:

GTGTCCTGCA  GTCGCGAAGA  GAGAAGGAAC  CTC                                    33
```